(12) United States Patent
MacLeod et al.

(10) Patent No.: US 8,362,018 B2
(45) Date of Patent: Jan. 29, 2013

(54) SUBSTITUTED IMIDAZO[1,2-A]PYRAZINE COMPOUNDS USEFUL FOR THE TREATMENT OF VIRAL INFECTIONS

(75) Inventors: Angus MacLeod, Saffron Walden (GB); Dale Robert Mitchell, Saffron Walden (GB); Nicholas John Palmer, Saffron Walden (GB); Michael Daniel Goldsmith, Saffron Walden (GB); Clifford John Harris, High Street Eynsford (GB); Christophe Claude Parsy, Jacou (FR)

(73) Assignee: Biofocus DPI, Ltd., Essex (GB)

( * ) Notice: Subject to any disclaimer, the term of this patent is extended or adjusted under 35 U.S.C. 154(b) by 103 days.

(21) Appl. No.: 12/674,525

(22) PCT Filed: Aug. 20, 2008

(86) PCT No.: PCT/EP2008/060896
§ 371 (c)(1),
(2), (4) Date: Apr. 15, 2010

(87) PCT Pub. No.: WO2009/024585
PCT Pub. Date: Feb. 26, 2009

(65) Prior Publication Data
US 2011/0166147 A1 Jul. 7, 2011

(30) Foreign Application Priority Data
Aug. 21, 2007 (GB) .................................. 0716292.8

(51) Int. Cl.
*A61K 31/495* (2006.01)
(52) U.S. Cl. ........................................ 514/249; 544/350
(58) Field of Classification Search .................. 514/249; 544/350
See application file for complete search history.

(56) References Cited

U.S. PATENT DOCUMENTS
2004/0063715 A1  4/2004  Paruch et al.
2004/0220189 A1  11/2004  Sun et al.
2005/0009832 A1  1/2005  Sun et al.
2007/0105864 A1  5/2007  Guiz et al.

FOREIGN PATENT DOCUMENTS
| WO | 02060492 | 8/2002 |
| WO | 2007058942 | 5/2007 |
| WO | 2008030795 | 3/2008 |
| WO | 2008079640 | 7/2008 |
| WO | WO2008079460 | 7/2008 |
| WO | WO 2009/024585 | * 2/2009 |

OTHER PUBLICATIONS

Jordan, V. C. Nature Reviews: Drug Discovery, 2, 2003, 205.*
Hackam, et al. JAMA, 296(14), 2006, 1731-1732.*
Bonnet, P.A., et al., "Synthesis and Antibronchospastic Activity of 8-Alkoxy- and 8-(Alkylamino)imidazo[1,2-a]pyrazines", Journal of Medicinal Chemistry, American Chemical Society, Washington, vol. 35, No. 18, Jan. 1, 1992, pp. 3353-3358.

* cited by examiner

*Primary Examiner* — Douglas M Willis
(74) *Attorney, Agent, or Firm* — Klauber & Jackson LLC

(57) ABSTRACT

Novel imidazopyrazine compounds are disclosed that have a formula represented by the following:

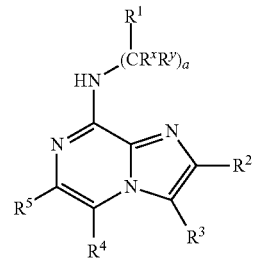

(I)

The compounds may be prepared as pharmaceutical compositions, and may be used for the prevention and treatment of a viral infection, in particular a HCV, HRV, Sb and/or CVB in a patient in need thereof.

17 Claims, No Drawings

SUBSTITUTED IMIDAZO[1,2-A]PYRAZINE COMPOUNDS USEFUL FOR THE TREATMENT OF VIRAL INFECTIONS

CROSS REFERENCE TO RELATED APPLICATIONS

The present application is a National Stage Application claiming the priority of co-pending PCT Application No. PCT/EP2008/060896 filed Aug. 20, 2008, which in turn, claims priority from United Kingdom Application No. GB 0716292.8 filed Aug. 21, 2007. Applicants claim the benefits of 35 U.S.C. §120 as to the PCT application and priority under 35 U.S.C. §119 as to the said United Kingdom application, and the entire disclosures of both applications are incorporated herein by reference in their entireties.

FIELD OF THE INVENTION

The invention is directed to imidazopyrazine compounds and pharmaceutical compositions containing such compounds that are useful in treating infections by hepatitis C virus and other viruses.

BACKGROUND TO THE INVENTION

The hepatitis C virus (HCV) is estimated to infect 170 million people worldwide and in many countries is the leading cause of chronic liver disease. Infection frequently leads to cirrhosis and hepatocellular carcinoma in long-term chronically infected patients. In most cases, clinical symptoms post-infection are mild or even subacute. Hence, many patients do not realize that they are infected until there is chronic liver damage 10-30 years after the initial infection. There are no vaccines or selective drugs currently available to treat HCV and the current standard therapies for HCV treatment are based on antiviral therapies that are not effective for a large number of patients, and are also poorly tolerated. The current best standard of care utilizes pegylated alpha-interferon and ribavirin. In the most common genotypes, this therapy is effective in less than 50% of cases and is associated with side effects and relapse after treatment cessation. Thus, there is a clear unmet need for effective therapies for the treatment of HCV infection.

HCV is an enveloped, positive-sense single-stranded RNA virus belonging to the Flaviviridae family. The 9.6 kb genome encodes for a single open reading frame, resulting in the translation of a single polyprotein of approximately 3,010 amino acids. In infected cells, this polyprotein is cleaved at multiple sites by cellular and viral proteases to produce the structural and non-structural (NS) proteins. The flanking 5' and 3' untranslated regions of the viral RNA genome contain important cis-acting signals for the initiation of viral RNA replication and protein translation. The HCV life-cycle can be separated into the following phases: 1) attachment to the cell membrane and entry into the cytoplasm; 2) cytoplasmic release and uncoating of the viral genome; 3) IRES-mediated translation; 4) polyprotein processing by cellular and viral proteases; 5) RNA replication; 6) packaging and assembly; 7) release from the host cell. As the HCV life cycle depends on the activity of numerous viral enzymes, engineering of specific enzyme inhibitors is being pursued in a number of laboratories to block HCV replication. Current research is mainly directed towards inhibiting HCV by targeting the non-structural proteins NS3 (protease and helicase) and NS5B (polymerase). Without wishing to be bound by any particular mechanism, it is believed that the compounds of the present invention target a host cell mechanism.

Picornaviruses are responsible for a large number of human viral diseases. The genus enterovirus, cardiovirus, rhinovirus, aphtovirus and hepatovirus especially the polioviruses (Sb), coxsackieviruses (CV), human echoviruses, human enteroviruses, human rhinoviruses (HRV) and hanks viruses all belong to the picornaviridae family. The disease syndromes range from mild upper respiratory disease to fatal neurological or cardiac-based illnesses. Rhinoviruses are estimated to cause approximately one-third of all upper respiratory tract viral infections. Examples of diseases caused by picornaviridae viral infections include, but are not limited to e.g. in humans aseptic meningitis, poliomyelitis, herpangina, pleurodynia (Bornholm disease), myositis, rhabdomyolysis, diabetes type 1, summer fever, encephalitis, febrile illness and myocarditis. In animals rhinoviruses and the foot and mouth disease viruses can be caused by such infections.

Picornaviruses are non-enveloped single-stranded positive-sense RNA viruses. The viral RNA genome is packaged in a capsid consisting of 60 repeating protomeric units, each one containing a copy of the four viral proteins VP1, VP2, VP3 and VP4. The structural organization of the viral capsid of several picornaviruses e.g. human rhinovirus 14 (HRV-14), poliovirus and coxsackievirus B3 has been elucidated by crystallization and resolution of the three-dimensional structure.

Imidazopyrazines are known in the literature and have been reported to be effective treatments for various disorders (e.g. WO 2008/059373 (acid pump antagonists), WO 2008/057512 (kinase inhibitors), WO 2004/074289 (gastric secretion inhibitors)). In particular, there are several reports of imidazopyrazines having a use in oncology by inhibiting cyclin-dependent kinases (e.g. WO 2007/058942, WO 2007/056468 and WO 2004/026877).

Surprisingly, the imidazopyrazines disclosed here have little or no effect on cyclin-dependent kinases and more surprisingly are effective as antiviral agents against a number of different viruses that include but are not limited to HCV, HRV, Sb and CVB.

SUMMARY OF THE INVENTION

The present invention describes novel imidazopyrazine compounds, pharmaceutically acceptable prodrugs, pharmaceutically active metabolites, pharmaceutically acceptable salts, and pharmaceutically acceptable solvates thereof, which are useful in treating or preventing a viral infection, in particular a hepatitis C virus (HCV) infection, in a patient in need thereof.

In a particular embodiment the present invention provides a method for treating a viral infection, said method comprising administering to the patient a therapeutically or prophylatically effective amount of an imidazopyrazine compound of the invention.

In a general aspect, the invention relates to compounds of Formula I

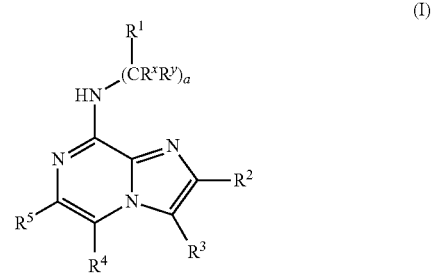

Wherein
- $R^1$ is selected from alkyl, substituted alkyl, aryl, substituted aryl, heteroaryl, substituted heteroaryl, cycloheteroalkyl and substituted cycloheteroalkyl;
- $R^2$ and $R^4$ may be the same or different and are each independently selected from H, alkyl and halo;
- $R^3$ is selected from halo, aryl, substituted aryl, heteroaryl and substituted heteroaryl;
- $R^5$ is selected from H, halo, alkyl, aryl and substituted aryl;
- Each Rx and $R^y$ may be the same or different and are each independently selected from H and alkyl;
- a is selected from 0, 1 or 2;
- or a pharmaceutically acceptable salt, solvate or prodrug thereof;
- and stereoisomers, isotopic variants and tautomers thereof.

In a further aspect, the present invention provides pharmaceutical compositions comprising an imidazopyrazine compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with a viral infection, particularly HCV and/or a picornavirus, which method comprises administering an effective amount of one or more of the pharmaceutical compositions just described.

In yet another method of treatment aspect, this invention provides a method for treating a mammal susceptible to or afflicted with a viral infection, and comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Accordingly, it is a principal object of this invention to provide a novel series of compounds, which can treat or prevent a viral infection. A still further object of this invention is to provide pharmaceutical compositions that are effective in the treatment or prevention of a viral infection.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)$R^{20}$, where $R^{20}$ is hydrogen, $C_1$-$C_8$ alkyl, $C_3$-$C_{10}$ cycloalkyl, $C_3$-$C_{10}$ cycloalkylmethyl, 4-10 membered cycloheteroalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered cycloheteroalkyl), wherein t is an integer from 0 to 4.

'Substituted Acyl' or 'Substituted Alkanoyl' refers to a radical —C(O)$R^{21}$, wherein $R^{21}$ is independently
- $C_1$-$C_8$ alkyl, substituted with halo or hydroxy; or
- $C_3$-$C_{10}$ cycloalkyl, 4-10 membered cycloheteroalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —NR$^{22}$C(O)R$^{23}$, where $R^{22}$ is hydrogen, $C_1$-$C_8$ alkyl, $C_3$-$C_{10}$ cycloalkyl, 4-10 membered cycloheteroalkyl, $C_6$-$C_{10}$ aryl, arylalkyl, 5-10 memberd heteroaryl or heteroarylalkyl and $R^{23}$ is hydrogen, $C_1$-$C_8$ alkyl, $C_3$-$C_{10}$ cycloalkyl, 4-10 membered cycloheteroalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Exemplary 'acylamino' groups are —NR$^{21'}$C(O)—$C_1$-$C_8$ alkyl, —NR$^{21'}$C(O)—(CH$_2$)$_t$($C_6$-$C_{10}$ aryl), —NR$^{21'}$C(O)—(CH$_2$)$_t$(5-10 membered heteroaryl), —NR$^{21'}$C(O)—(CH$_2$)$_t$($C_3$-$C_{10}$ cycloalkyl), and —NR$^{21'}$C(O)—(CH$_2$)$_t$(4-10 membered cycloheteroalkyl), wherein t is an integer from 0 to 4, each $R^{21'}$ independently represents H or $C_1$-$C_8$ alkyl.

'Substituted Acylamino' refers to a radical —NR$^{24}$C(O)R$^{25}$, wherein:
- $R^{24}$ is independently
  - H, $C_1$-$C_8$ alkyl, substituted with halo or hydroxy; or
  - $C_3$-$C_{10}$ cycloalkyl, 4-10 membered cycloheteroalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and
- $R^{25}$ is independently
  - H, $C_1$-$C_8$ alkyl, substituted with halo or hydroxy; or
  - $C_3$-$C_{10}$ cycloalkyl, 4-10 membered cycloheteroalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl;

provided at least one of $R^{24}$ and $R^{25}$ is other than H.

'Alkoxy' refers to the group —OR$^{26}$ where R$^{26}$ is C$_1$-C$_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, C$_6$-C$_{10}$ aryl, —O-aryl, carboxyl, cyano, C$_3$-C$_{10}$ cycloalkyl, 4-10 membered cycloheteroalkyl, halogen, 5-10 membered heteroaryl, hydroxyl, nitro, thioalkyl, thio-O-aryl, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered cycloheteroalkyl), wherein t is an integer from 0 to 4 and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, OCH$_2$CH$_2$NMe$_2$.

'Alkoxycarbonyl' refers to a radical —C(O)—OR$^{27}$ where R$^{27}$ represents an C$_1$-C$_8$ alkyl, C$_3$-C$_{10}$ cycloalkyl, C$_3$-C$_{10}$ cycloalkylalkyl, 4-10 membered cycloheteroalkyl, aralkyl, or 5-10 membered heteroarylalkyl as defined herein. Exemplary "alkoxycarbonyl" groups are C(O)O—C$_1$-C$_8$ alkyl, —C(O)O—(CH$_2$)$_t$(C$_6$-C$_{10}$ aryl), —C(O)O—(CH$_2$)$_t$(5-10 membered heteroaryl), —C(O)O—(CH$_2$)$_t$(C$_3$-C$_{10}$ cycloalkyl), and —C(O)O—(CH$_2$)$_t$(4-10 membered cycloheteroalkyl), wherein t is an integer from 1 to 4.

'Substituted Alkoxycarbonyl' refers to a radical —C(O)—OR$^{28}$ where R$^{28}$ represents:
  C$_1$-C$_8$ alkyl, C$_3$-C$_{10}$ cycloalkyl, C$_3$-C$_{10}$ cycloalkylalkyl, or 4-10 membered cycloheteroalkylalkyl, each of which is substituted with halo, substituted or unsubstituted amino, or hydroxy; or
  C$_6$-C$_{10}$ aralkyl, or 5-10 membered heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'-O-arylcarbonyl' refers to a radical —C(O)—OR$^{29}$ where R$^{29}$ represents an C$_6$-C$_{10}$ aryl, as defined herein. Exemplary "–O-arylcarbonyl" groups is —C(O)O—(C$_6$-C$_{10}$ aryl).

'Substituted —O-arylcarbonyl' refers to a radical —C(O)—OR$^{30}$ where R$^{30}$ represents a C$_6$-C$_{10}$ aryl, substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'Hetero-O-arylcarbonyl' refers to a radical —C(O)—OR$^{31}$ where R$^{31}$ represents a 5-10 membered heteroaryl, as defined herein.

'Substituted Hetero-O-arylcarbonyl' refers to a radical —C(O)—OR$^{32}$ where R$^{32}$ represents a 5-10 membered heteroaryl, substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'Alkyl' means straight or branched aliphatic hydrocarbon having 1 to 20 carbon atoms. Particular alkyl has 1 to 12 carbon atoms. A further particular group has 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{22}$), amino, substituted amino, aminocarbonyl (carbamoyl or amido or —C(O)—NR"$_2$), aminocarbonylamino (—NR"-C(O)—NR"$_2$), aminocarbonyloxy (—O—C(O)—NR"$_2$), aminosulfonyl, sulfonylamino, aryl, —O-aryl, azido, carboxyl, cyano, cycloalkyl, halogen, hydroxy, heteroaryl, nitro, thiol, —S-alkyl, —S-aryl, —S(O)-alkyl,S(O)-aryl, —S(O)$_2$-alkyl, and —S(O)$_2$-aryl. In a particular embodiment 'substituted alkyl' refers to a C$_1$-C$_8$ alkyl group substituted with halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', or —(CR'''R'''')$_m$ OR'''; wherein each R'' is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered cycloheteroalkyl), wherein t is an integer from 0 to 4 and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each of R''' and R'''' independently represents H or C$_1$-C$_8$ alkyl.

'Amino' refers to the radical —NH$_2$.

'Substituted amino' refers to an amino group substituted with one or more of those groups recited in the definition of 'substituted' herein, and particularly refers to the group —N(R$^{33}$)$_2$ where each R$^{33}$ is independently selected from:
  hydrogen, C$_1$-C$_8$ alkyl, C$_6$-C$_{10}$ aryl, 5-10 membered heteroaryl, 4-10 membered cycloheteroalkyl, or C$_3$-C$_{10}$ cycloalkyl; or
  C$_1$-C$_8$ alkyl, substituted with halo or hydroxy; or
  —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl) or —(CH$_2$)$_t$(4-10 membered cycloheteroalkyl) wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or
  both R$^{33}$ groups are joined to form an alkylene group.

When both R$^{33}$ groups are hydrogen, —N(R$^{33}$)$_2$ is an amino group. Exemplary 'substituted amino' groups are —NR$^{33'}$—C$_1$-C$_8$ alkyl, —NR$^{33'}$—(CH$_2$)$_t$(C$_6$-C$_{10}$ aryl), —NR$^{33'}$—(CH$_2$)$_t$(5-10 membered heteroaryl), —NR$^{33'}$—(CH$_2$)$_t$(C$_3$-C$_{10}$ cycloalkyl), and —NR$^{33'}$—(CH$_2$)$_t$(4-10 membered cycloheteroalkyl), wherein t is an integer from 0 to 4, each R$^{33'}$ independently represents H or C$_1$-C$_8$ alkyl; and any alkyl groups present, may themselves be substituted by halo, substituted or unsubstituted amino, or hydroxy; and any aryl, heteroaryl, cycloalkyl or cycloheteroalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{34}$, wherein R$^{34}$ is $C_1$-$C_8$ alkyl.

'Substituted Alkylamino' refers to the group —NHR$^{35}$, wherein R$^{35}$ is $C_1$-$C_8$ alkyl; and the alkyl group is substituted with halo, substituted or unsubstituted amino, hydroxy, $C_3$-$C_{10}$ cycloalkyl, 4-10 membered cycloheteroalkyl, $C_6$-$C_{10}$ aryl, 5-10 membered heteroaryl, aralkyl or heteroaralkyl; and any aryl, heteroaryl, cycloalkyl or cycloheteroalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkylarylamino' refers to the group —NR$^{36}$R$^{37}$, wherein R$^{36}$ is $C_6$-$C_{10}$ aryl and R$^{37}$ is $C_1$-$C_8$ alkyl.

'Substituted Alkylarylamino' refers to the group —NR$^{38}$R$^{39}$, wherein R$^{38}$ is $C_6$-$C_{10}$ aryl and R$^{39}$ is $C_1$-$C_8$ alkyl; and the alkyl group is substituted with halo, substituted or unsubstituted amino, hydroxy, $C_3$-$C_{10}$ cycloalkyl, 4-10 membered cycloheteroalkyl, $C_6$-$C_{10}$ aryl, 5-10 membered heteroaryl, aralkyl or heteroaralkyl; and any aryl, heteroaryl, cycloalkyl or cycloheteroalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —NHR$^{40}$ where R$^{40}$ is selected from $C_6$-$C_{10}$ aryl and 5-10 membered heteroaryl as defined herein.

'Substituted Arylamino' refers to the group —NHR$^{41}$, wherein R$^{41}$ is independently selected from $C_6$-$C_{10}$ aryl and 5-10 membered heteroaryl; and any aryl or heteroaryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Dialkylamino' refers to the group —NR$^{42}$R$^{43}$, wherein each of R$^{42}$ and R$^{43}$ are independently selected from $C_1$-$C_8$ alkyl.

'Substituted Dialkylamino' refers to the group —NR$^{44}$R$^{45}$, wherein each of R$^{44}$ and R$^{45}$ are independently selected from $C_1$-$C_8$ alkyl; and the alkyl group is independently substituted with halo, hydroxy, $C_3$-$C_{10}$ cycloalkyl, 4-10 membered cycloheteroalkyl, $C_6$-$C_{10}$ aryl, 5-10 membered heteroaryl, aralkyl or heteroaralkyl; and any aryl, heteroaryl, cycloalkyl or cycloheteroalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Diarylamino' refers to the group —NR$^{46}$R$^{47}$, wherein each of R$^{46}$ and R$^{42}$ are independently selected from $C_6$-$C_{10}$ aryl.

"Aminosulfonyl" or "Sulfonamide" refers to the radical —S(O$_2$)NH$_2$.

"Substituted aminosulfonyl" or "substituted sulfonamide" refers to a radical such as —S(O$_2$)N(R$^{48}$)$_2$ wherein each R$^{48}$ is independently selected from:

H, $C_1$-$C_8$ alkyl, $C_3$-$C_{10}$ cycloalkyl, 4-10 membered cycloheteroalkyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered cycloheteroalkyl, $C_6$-$C_{10}$ aryl, aralkyl, 5-10 membered heteroaryl, or heteroaralkyl, substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one R$^{48}$ is other than H.

Exemplary 'substituted aminosulfonyl' or 'substituted sulfonamide' groups are—S(O$_2$)N(R$^{48'}$)—$C_1$-$C_8$ alkyl, —S(O$_2$)N(R$^{48'}$)—(CH$_2$)$_t$(C$_6$-$C_{10}$ aryl), —S(O$_2$)N(R$^{48'}$)—(CH$_2$)$_t$(5-10 membered heteroaryl), —S(O$_2$)N(R$^{48'}$)—(CH$_2$)$_t$(C$_3$-$C_{10}$ cycloalkyl), and —S(O$_2$)N(R$^{48'}$)—(CH$_2$)$_t$(4-10 membered cycloheteroalkyl), wherein t is an integer from 0 to 4; each R$^{48'}$ independently represents H or $C_1$-$C_8$ alkyl; and any aryl, heteroaryl, cycloalkyl or cycloheteroalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of any aryl group present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, $C_1$-$C_8$ haloalkoxy, cyano, hydroxy, $C_1$-$C_8$ alkoxy, and amino.

Examples of representative substituted aryls include the following

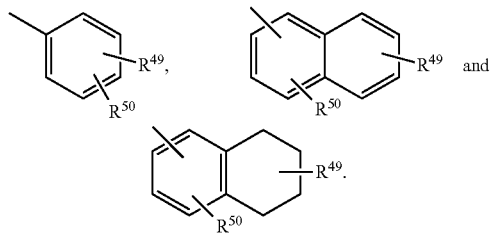

In these formulae one of $R^{49}$ and $R^{50}$ may be hydrogen and at least one of $R^{49}$ and $R^{50}$ is each independently selected from $C_1$-$C_8$ alkyl, 4-10 membered cycloheteroalkyl, alkanoyl, $C_1$-$C_8$ alkoxy, hetero-O-aryl, alkylamino, arylamino, heteroarylamino, $NR^{51}COR^{52}$, $NR^{51}SOR^{52}NR^{51}SO_2R^{52}$, COOalkyl, COOaryl, $CONR^{51}R^{52}$, $CONR^{51}OR^{52}$, $NR^{51}R^{52}$, $SO_2NR^{51}R^{52}$, S-alkyl, SOalkyl, $SO_2$alkyl, Saryl, SOaryl, $SO_2$aryl; or $R^{49}$ and $R^{50}$ may be joined to form a cyclic ring (saturated or unsaturated) from 5 to 8 atoms, optionally containing one or more heteroatoms selected from the group N, O or S. $R^{51}$, and $R^{52}$ are independently hydrogen, $C_1$-$C_8$ alkyl, $C_1$-$C_4$ haloalkyl, $C_3$-$C_{10}$ cycloalkyl, 4-10 membered cycloheteroalkyl, $C_6$-$C_{10}$ aryl, substituted aryl, 5-10 membered heteroaryl.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Azido' refers to the radical —$N_3$.

'Carbamoyl or amido' refers to the radical —$C(O)NH_2$.

'Substituted Carbamoyl or substituted amido' refers to the radical —$C(O)N(R^{53})_2$ wherein each $R^{53}$ is independently H, $C_1$-$C_8$ alkyl, $C_3$-$C_{10}$ cycloalkyl, 4-10 membered cycloheteroalkyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered cycloheteroalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{53}$ is other than H.

Exemplary 'Substituted Amido/Carbamoyl' groups are —$C(O)NR^{53'}$—$C_1$-$C_8$ alkyl, —$C(O)NR^{53'}$—$(CH_2)_t(C_6$-$C_{10}$ aryl), —$C(O)N^{53'}$—$(CH_2)_t$(5-10 membered heteroaryl), —$C(O)NR^{53'}$—$(CH_2)_t(C_3$-$C_{10}$ cycloalkyl), and —$C(O)NR^{53'}$—$(CH_2)_t$(4-10 membered cycloheteroalkyl), wherein t is an integer from 0 to 4, each $R^{53'}$ independently represents H or $C_1$-$C_8$ alkyl and any aryl, heteroaryl, cycloalkyl or cycloheteroalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —$C(O)OH$.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, cyclohexyl, cycloheptyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative aryl having hetero atoms containing substitution include the following:

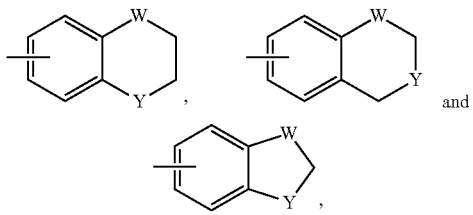

wherein each W is selected from C(R⁵⁴)₂, NR⁵⁴, O and S; and each Y is selected from carbonyl, NR⁵⁴, O and S; and R⁵⁴ is independently hydrogen, $C_1$-$C_8$ alkyl, $C_3$-$C_{10}$ cycloalkyl, 4-10 membered cycloheteroalkyl, $C_6$-$C_{10}$ aryl, and 5-10 membered heteroaryl.

Examples of representative heteroaryls include the following:

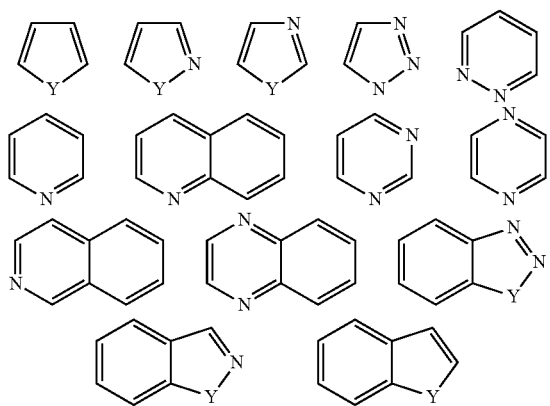

wherein each Y is selected from carbonyl, N, NR⁵⁵, O and S; and R⁵⁵ is independently hydrogen, $C_1$-$C_8$ alkyl, $C_3$-$C_{10}$ cycloalkyl, 4-10 membered cycloheteroalkyl, $C_6$-$C_{10}$ aryl, and 5-10 membered heteroaryl.

As used herein, the term 'cycloheteroalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of cycloheteroalkyl groups are shown in the following illustrative examples:

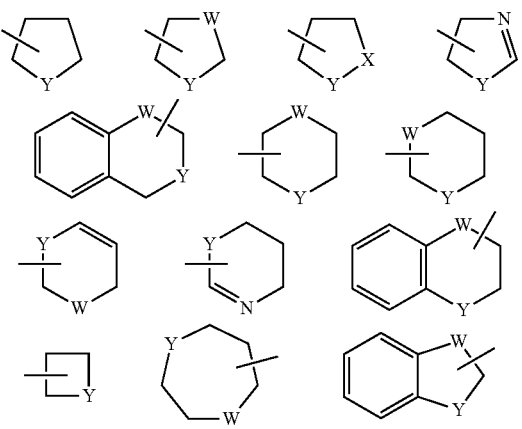

wherein each W is selected from CR⁵⁶, C(R⁵⁶)₂, NR⁵⁶, O and S; and each Y is selected from NR⁵⁶, O and S; and R⁵⁶ is independently hydrogen, $C_1$-$C_8$ alkyl, $C_3$-$C_{10}$ cycloalkyl, 4-10 membered cycloheteroalkyl, $C_6$-$C_{10}$ aryl, 5-10 membered heteroaryl, These cycloheteroalkyl rings may be optionally substituted with one or more groups selected from the group consisting of acyl, acylamino, acyloxy (—O-acyl or —OC(O)R²⁰), alkoxy, alkoxycarbonyl, alkoxycarbonylamino (—NR″-alkoxycarbonyl or —NH—C(O)—OR²⁷), amino, substituted amino, aminocarbonyl (amido or —C(O)—NR″₂), aminocarbonylamino (—NR″-C(O)—NR″₂), aminocarbonyloxy (—O—C(O)—NR″₂), aminosulfonyl, sulfonylamino, aryl, —O-aryl, azido, carboxyl, cyano, cycloalkyl, halogen, hydroxy, nitro, thiol, —S-alkyl, —S-aryl, —S(O)-alkyl, —S(O)-aryl, —S(O)₂-alkyl, and —S(O)₂-aryl. Substituting groups include carbonyl or thiocarbonyl which provide, for example, lactam and urea derivatives.

'Hydroxy' refers to the radical —OH.

'Nitro' refers to the radical —NO₂.

'Substituted' refers to a group in which one or more hydrogen atoms are each independently replaced with the same or different substituent(s). Typical substituents may be selected from the group consisting of:

halogen, —R⁵⁷, —O⁻, =O, —OR⁵⁷, —SR⁵⁷, —S⁻, =S, —NR⁵⁷R⁵⁸, =NR⁵⁷, —CCl₃, —CF₃, —CN, —OCN, —SCN, —NO, —NO₂, =N₂, —N₃, —S(O)₂O⁻, —S(O)₂OH, —S(O)₂R⁵⁷, —OS(O₂)O⁻, —OS(O)₂R⁵⁷, —P(O)(O⁻)₂, —P(O)(OR⁵⁷)(O⁻), —OP(O)(OR⁵⁷)(OR⁵⁸), —C(O)R⁵⁷, —C(S)R⁵⁷, —C(O)OR⁵⁷, —C(O)NR⁵⁷R⁵⁸, —C(O)O⁻, —C(S)OR⁵⁷, —NR⁵⁹C(O)NR⁵⁷R⁵⁸, —NR⁵⁹C(S)NR⁵⁷R⁵⁸, —NR⁶⁰C(NR⁵⁹)NR⁵⁷R⁵⁸ and —C(NR⁵⁹)NR⁵⁷R⁵⁸;

wherein each R⁵⁷, R⁵⁸, R⁵⁹ and R⁶⁰ are independently:

hydrogen, $C_1$-$C_8$ alkyl, $C_6$-$C_{10}$ aryl, arylalkyl, $C_3$-$C_{10}$ cycloalkyl, 4-10 membered cycloheteroalkyl, 5-10 membered heteroaryl, heteroarylalkyl; or $C_1$-$C_8$ alkyl substituted with halo or hydroxy; or $C_6$-$C_{10}$ aryl, 5-10 membered heteroaryl, $C_6$-$C_{10}$ cycloalkyl or 4-10 membered cycloheteroalkyl substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from: halo, cyano, nitro, trifluoromethyl, trifluoromethoxy, azido, —NR'''SO$_2$R''', —SO$_2$NR''R''', —C(O)R'', —C(O)OR'', —OC(O)R'', —NR'''C(O)R'', —C(O)NR''R''', —NR''R''', —(CR'''R''', wherein, each R'' is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$ (C$_3$-C$_{10}$ cycloalkyl), and —(CH$_2$)$_t$(4-10 membered cycloheteroalkyl), wherein t is an integer from 0 to 4; and any alkyl groups present, may themselves be substituted by halo or hydroxy; and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each R'' independently represents H or C$_1$-C$_6$alkyl.

'Substituted sulfanyl' refers to the group —SR$^{61}$, wherein R$^{61}$ is selected from:

C$_1$-C$_8$ alkyl, C$_3$-C$_{10}$ cycloalkyl, 4-10 membered cycloheteroalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered cycloheteroalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfanyl' groups are —S—(C$_1$-C$_8$ alkyl) and —S—(C$_3$-C$_{10}$ cycloalkyl), —S—(CH$_2$)$_t$(C$_6$-C$_{10}$ aryl), —S—(CH$_2$)$_t$(5-10 membered heteroaryl), —S—(CH$_2$)$_t$ (C$_3$-C$_{10}$ cycloalkyl), and —S—(CH$_2$)$_t$(4-10 membered cycloheteroalkyl), wherein t is an integer from 0 to 4 and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloallthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —SR$^{62}$ where R$^{62}$ is a C$_1$-C$_8$ alkyl or group as defined herein. Representative examples include, but are not limited to, methylthio, ethylthio, propylthio and butylthio.

'Substituted Alkylthio' or 'substituted alkylsulfanyl' refers to the group —SR$^{63}$ where R$^{63}$ is a C$_1$-C$_8$ alkyl, substituted with halo, substituted or unsubstituted amino, or hydroxy.

'Cycloalkylthio' or 'Cycloalkylsulfanyl' refers to a radical —SR$^{64}$ where R$^{64}$ is a C$_3$-C$_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —SR$^{65}$ where R$^{65}$ is a C$_3$-C$_{10}$ cycloalkyl, substituted with halo, substituted or unsubstituted amino, or hydroxy.

'Arylthio' or 'Arylsulfanyl' refers to a radical —SR$^{66}$ where R$^{66}$ is a C$_6$-C$_{10}$ aryl group as defined herein.

'Heteroarylthio' or 'Heteroarylsulfanyl' refers to a radical —SR$^{67}$ where R$^{67}$ is a 5-10 membered heteroaryl group as defined herein.

'Substituted sulfinyl' refers to the group —S(O)R$^{68}$, wherein R$^{68}$ is selected from:

C$_1$-C$_8$ alkyl, C$_3$-C$_{10}$ cycloalkyl, 4-10 membered cycloheteroalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered cycloheteroalkyl, C$_6$-C$_{10}$ aryl, aralkyl, 5-10 membered heteroaryl, or heteroaralkyl, substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfinyl' groups are —S(O)—(C$_1$-C$_8$ alkyl) and —S(O)—(C$_3$-C$_{10}$ cycloalkyl), —S(O)—(CH$_2$)$_t$(C$_6$-C$_{10}$ aryl), —S(O)—(CH$_2$)$_t$(5-10 membered heteroaryl), —S(O)—(CH$_2$)$_t$(C$_3$-C$_{10}$ cycloalkyl), and —S(O)—(CH$_2$)$_t$(4-10 membered cycloheteroalkyl), wherein t is an integer from 0 to 4 and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —S(O)R$^{69}$ where R$^{69}$ is a C$_1$-C$_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —S(O)R$^{70}$ where R$^{70}$ is a C$_1$-C$_8$ alkyl group as defined herein. substituted with halo, substituted or unsubstituted amino, or hydroxy.

'Cycloalkylsulfinyl' refers to a radical —S(O)R$^{71}$ where R$^{71}$ is a C$_3$-C$_{10}$ cycloalkyl or group as defined herein. Representative examples include, but are not limited to, cyclopropylsulfinyl, cyclohexylsulfinyl, and cyclopentylsulfinyl.

'Substituted cycloalkylsulfinyl' refers to the group —S(O) R$^{72}$ where R$^{72}$ is a C$_3$-C$_{10}$ cycloalkyl, substituted with halo, substituted or unsubstituted amino, or hydroxy.

'Arylsulfinyl' refers to a radical —S(O)R$^{73}$ where R$^{73}$ is a C$_6$-C$_{10}$ aryl group as defined herein.

'Heteroarylsulfinyl' refers to a radical —S(O)R$^{74}$ where R$^{74}$ is a 5-10 membered heteroaryl group as defined herein.

'Substituted sulfonyl' refers to the group —S(O)$_2$R$^{75}$, wherein R$^{75}$ is selected from:

C$_1$-C$_8$ alkyl, C$_3$-C$_{10}$ cycloalkyl, 4-10 membered cycloheteroalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered cycloheteroalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfonyl' groups are —S(O)$_2$—(C$_1$-C$_8$ alkyl) and —S(O)$_2$—(C$_3$-C$_{10}$ cycloalkyl), —S(O)$_2$—(CH$_2$)$_t$(C$_6$-C$_{10}$ aryl), —S(O)$_2$—(CH$_2$)$_t$(5-10 membered heteroaryl), —S(O)$_2$—(CH$_2$)$_t$(C$_3$-C$_{10}$ cycloalkyl), and —S(O)$_2$—(CH$_2$)$_t$(4-10 membered cycloheteroalkyl), wherein t is an integer from 0 to 4 and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —S(O)$_2$R$^{76}$ where R$^{76}$ is an C$_1$-C$_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —S(O)$_2$R$^{76}$ where R$^{76}$ is an C$_1$-C$_8$ alkyl group as defined herein, substituted with halo, substituted or unsubstituted amino, or hydroxy.

'Cycloalkylsulfonyl' refers to a radical —S(O)$_2$R$^{78}$ where R$^{78}$ is a C$_3$-C$_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —S(O)$_2$ R$^{79}$ where R$^{79}$ is a C$_3$-C$_{10}$ cycloalkyl, substituted with halo, substituted or unsubstituted amino, or hydroxy.

'Arylsulfonyl' refers to a radical —S(O)$_2$R$^{80}$ where R$^{80}$ is an C$_6$-C$_{10}$ aryl group as defined herein.

'Heteroarylsulfonyl' refers to a radical —S(O)$_2$R$^{81}$ where R$^{81}$ is an 5-10 membered heteroaryl group as defined herein.

'Sulfo' or 'sulfonic acid' refers to a radical such as —SO$_3$H.

'Substituted sulfo' or 'sulfonic acid ester' refers to the group —S(O)$_2$OR$^{82}$, wherein R$^{82}$ is selected from:

C$_1$-C$_8$ alkyl, C$_3$-C$_{10}$ cycloalkyl, 4-10 membered cycloheteroalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered cycloheteroalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'Substituted sulfo' or 'sulfonic acid ester' groups are —S(O)$_2$—O—(C$_1$-C$_8$ alkyl) and —S(O)$_2$—O—(C$_3$-C$_{10}$ cycloalkyl), —S(O)$_2$—O—(CH$_2$)$_t$(C$_6$-C$_{10}$ aryl), —S(O)$_2$—O—(CH$_2$)$_t$(5-10 membered heteroaryl), —S(O)$_2$—O—(CH$_2$)$_t$(C$_3$-C$_{10}$ cycloalkyl), and —S(O)$_2$—O—(CH$_2$)$_t$(4-10 membered cycloheteroalkyl), wherein t is an integer from 0 to 4 and any aryl, heteroaryl, cycloalkyl or cycloheteroalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_2$-$C_{12}$ substituted aryl, and $C_2$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of n electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R) — or (S)— stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

The present invention is based on the discovery that the imidazopyrazine compounds of the invention are useful for the treatment of viral infection, in particular HCV, HRV, Sb, and/or CVB. The present invention also provides methods for the production of these compounds, pharmaceutical compositions comprising these compounds and methods for treating a viral infection by administering a compound of the invention.

In a general aspect, the invention relates to compounds of Formula (I)

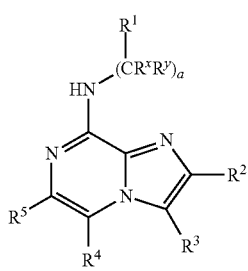

(I)

Wherein
- $R^1$ is selected from alkyl, substituted alkyl, aryl, substituted aryl, heteroaryl, substituted heteroaryl, cycloheteroalkyl and substituted cycloheteroalkyl;
- $R^2$ and $R^4$ may be the same or different and are each independently selected from H, alkyl and halo;
- $R^3$ is selected from halo, aryl, substituted aryl, heteroaryl and substituted heteroaryl;
- $R^5$ is selected from H, halo, alkyl, aryl and substituted aryl;
- Each $R^x$ and $R^y$ may be the same or different and are each independently selected from H and alkyl; and
- a is selected from 0, 1 or 2;
- or a pharmaceutically acceptable salt, solvate or prodrug thereof;
- or stereoisomers, isotopic variants and tautomers thereof.

In a particular embodiment, with respect to compounds according to Formula (I):
- $R^1$ is selected from $C_1$-$C_6$ alkyl, substituted $C_1$-$C_6$ alkyl, $C_6$-$C_{10}$ aryl, substituted $C_6$-$C_{10}$ aryl, 5-10 membered heteroaryl, substituted 5-10 membered heteroaryl, 4-10 membered cycloheteroalkyl and substituted 4-10 membered cycloheteroalkyl;
- $R^2$ and $R^4$ may be the same or different and are each independently selected from H, $C_1$-$C_6$ alkyl and halo;
- $R^3$ is selected from halo, $C_6$-$C_{10}$ aryl, substituted $C_6$-$C_{10}$ aryl, 5-10 membered heteroaryl and substituted 5-10 membered heteroaryl;
- $R^5$ is selected from H, halo, $C_1$-$C_6$ alkyl, $C_6$-$C_{10}$ aryl and substituted $C_6$-$C_{10}$ aryl;
- Each $R^x$ and $R^y$ may be the same or different and are each independently selected from H and $C_1$-$C_6$ alkyl; and
- a is selected from 0, 1 or 2;
- or a pharmaceutically acceptable salt thereof.

In a particular embodiment, the invention relates to compounds according to Formulae (IIA)-(IIC) below:

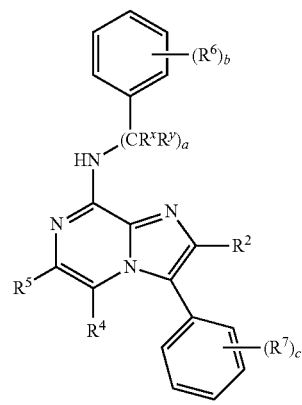

(IIA)

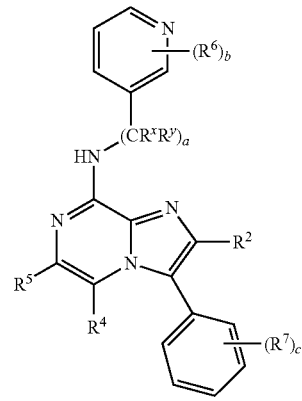

(IIB)

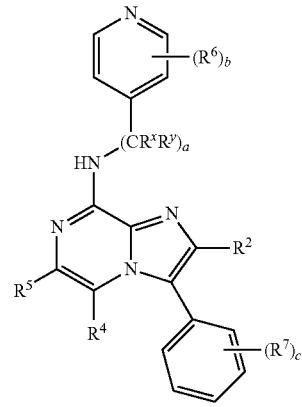

(IIC)

Wherein
- $R^x$, $R^y$, $R^2$, $R^4$, $R^5$ and a are as defined for Formula (I) above; Each $R^6$ may be the same or different and is selected from halo, OH, $C_1$-$C_6$ alkyl, substituted $C_1$-$C_6$ alkyl, $C_1$-$C_6$ haloalkyl, $C_1$-$C_6$ alkoxy, substituted $C_1$-$C_6$ alkoxy, CN, $C_1$-$C_6$ alkyl-OH, $SO_2R_8$, $CO_2R_8$, $COR_8$, and $NHSO_2R_8$;
- Each $R^7$ may be the same or different and is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $CF_3$, $OCF_3$, $C_1$-$C_6$ alkyl-OH, $NHSO_2R^9$, $COR^8$, $NHCOR^8$, and $NR^9R^{10}$;
- $R^8$ is selected from H, $C_1$-$C_6$ alkyl, substituted $C_1$-$C_6$ alkyl, and $NR^9R^{10}$;
- $R^9$ and $R^{10}$ may be the same or different and are selected from H, $C_1$-$C_6$ alkyl, and substituted $C_1$-$C_6$ alkyl; and
- b and c are each selected from 0, 1, 2 or 3.

In a particular embodiment, with respect to compounds according to any one of Formulae (IIA)-(IIC):

$R^x$, $R^y$, $R^2$, $R^4$, $R^5$ and a are as defined for Formula (I) above;

Each $R^6$ may be the same or different and is selected from halo, OH, $C_1$-$C_6$ alkyl, substituted $C_1$-$C_6$ alkyl, $C_1$-$C_6$ haloalkyl, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

Each R' may be the same or different and is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $CF_3$, $OCF_3$, $C_1$-$C_6$ alkyl-OH, $NHSO_2R^9$, $NHCOR^8$, and $NR^9R^{10}$;

$R^8$ is selected from H, $C_1$-$C_6$ alkyl, substituted $C_1$-$C_6$ alkyl, and $NR^9R^{10}$, $R^9$ and $R^{10}$ may be the same or different and are selected from H, $C_1$-$C_6$ alkyl, and substituted $C_1$-$C_6$ alkyl; and b and c are selected from 0, 1, 2 or 3.

In a particular embodiment, with respect to compounds according to any one of Formulae (IIA)-(IIC), $R^2$, $R^4$ and $R^5$ are selected from H, Me, and Et.

In a particular embodiment, with respect to compounds according to any one of Formulae (IIA)-(IIC), $R^2$, $R^4$ and $R^5$ are selected from H and Me.

In a particular embodiment, with respect to compounds according to any one of Formulae (IIA)-(IIC) Rx and $R^y$ are both H.

In a particular embodiment, with respect to compounds according to any one of Formulae (IIA)-(IIC), $R^6$ is selected from halogen, $CF_3$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkyl-OH, $SO_2R^8$, and $COR^8$.

In a particular embodiment, with respect to compounds according to any one of Formulae (IIA)-(IIC), $R^6$ is selected from halogen, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkyl-OH, and $SO_2R^8$.

In a particular embodiment, with respect to compounds according to any one of Formulae (IIA)-(IIC), $R^6$ is selected from halogen, $C_1$-$C_6$ alkyl, $C_1$-$C_6$ alkoxy, $C_1$-$C_6$ alkyl-OH $COR^8$, and $SO_2R^8$.

In a particular embodiment, with respect to compounds according to any one of Formulae (IIA)-(IIC), $R^6$ is selected from halogen, $C_1$-$C_6$ alkyl, $C_1$-$C_6$ alkoxy, $C_1$-$C_6$ alkyl-OH and $SO_2R^8$.

In a particular embodiment, with respect to compounds according to any one of Formulae (IIA)-(IIC), $R^6$ is $SO_2R^8$, where $R^8$ is $C_1$-$C_6$ alkyl, or $NR^9R^{10}$.

In a particular embodiment, with respect to compounds according to any one of Formulae (IIA)-(IIC), R' is selected from OH, $NO_2$, $C_1$-$C_6$ alkoxy, substituted $C_1$-$C_6$ alkoxy, halogen, $C_1$-$C_6$ alkyl, substituted $C_1$-$C_6$ alkyl, $NR^9R^{10}$, $NHSO_2R^8$ and $NHCOR^8$.

In a particular embodiment, with respect to compounds according to any one of Formulae (IIA)-(IIC), R' is selected from OH, $NO_2$, $NH_2$, $C_1$-$C_6$ alkoxy, halogen, $C_1$-$C_6$ alkyl, $NHSO_2R^8$ and $NHCOR^8$; where $R^8$ is $C_1$-$C_6$ alkyl.

In a particular embodiment, with respect to compounds according to any one of Formulae (IIA)-(IIC), R' is selected from OH, $NO_2$, $NH_2$, and $COR^8$; where $R^8$ is $C_1$-$C_6$ alkyl.

In a particular embodiment, with respect to compounds according to any one of Formulae (IIA)-(IIC), R' is selected from OH, $NO_2$, $NH_2$, OMe, halogen, $NHSO_2R^8$ and $NHCOR^8$; where $R^8$ is $C_1$-$C_6$ alkyl.

In a particular embodiment, the compounds are according to Formula (IIB) or (IIC).

In a particular embodiment, the invention relates to compounds according to Formulae (IIIA)-(IIIC) below:

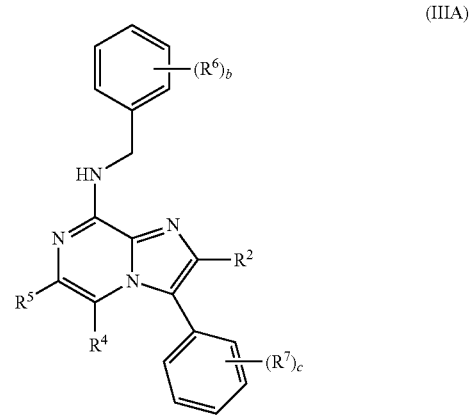

(IIIA)

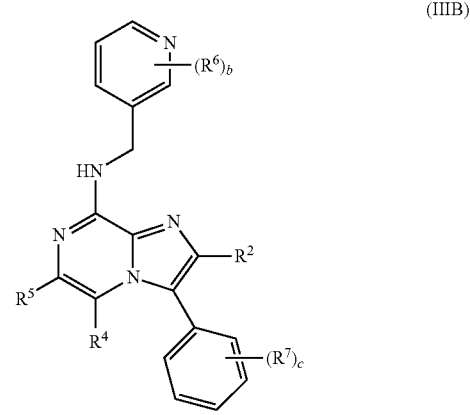

(IIIB)

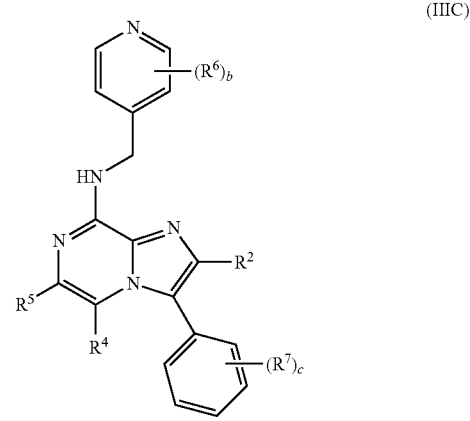

(IIIC)

Wherein $R^2$, $R^4$ and $R^5$ are as defined for Formula (I) above;

Each $R^6$ may be the same or different and is selected from halo, OH, $C_1$-$C_6$ alkyl, substituted $C_1$-$C_6$ alkyl, $C_1$-$C_6$ haloalkyl, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

Each $R^7$ may be the same or different and is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ haloalkyl, $OCF_3$, alkyl-OH, $NHSO_2R^9$, $COR^8$, $NHCOR^8$, and $NR^9R^{10}$;

$R^8$ is selected from H, $C_1$-$C_6$ alkyl, substituted $C_1$-$C_6$ alkyl, and $NR^9R^{10}$;

$R^9$ and $R^{10}$ may be the same or different and are selected from H, $C_1$-$C_6$ alkyl, and substituted $C_1$-$C_6$ alkyl; and b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above;

Each $R^6$ may be the same or different and is selected from halo, OH, $C_1$-$C_6$ alkyl, substituted $C_1$-$C_6$ alkyl, $CF_3$, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

Each R' may be the same or different and is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $CF_3$, $OCF_3$, alkyl-OH, $NHSO_2R^9$, $COR^8$, $NHCOR^8$, and $NR^9R^{10}$;

$R^8$ is selected from H, $C_1$-$C_6$ alkyl, substituted $C_1$-$C_6$ alkyl, and $NR^9R^{10}$;

$R^9$ and $R^{10}$ may be the same or different and are selected from H, $C_1$-$C_6$ alkyl, and substituted $C_1$-$C_6$ alkyl; and b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above;

Each $R^6$ may be the same or different and is selected from halo, OH, $C_1$-$C_6$ alkyl, $C_1$-$C_6$ haloalkyl, $C_1$-$C_6$ alkoxy, CN, $C_1$-$C_6$ alkyl-OH, $SO_2R^8$, $CO_2R^8$, $COR^8$ and $NHSO_2R^8$;

Each $R^7$ may be the same or different and is selected from OH, halo, CN, $NO_2$, $C_1$-$C_6$ alkyl, $C_1$-$C_6$ alkoxy, $C_1$-$C_6$ haloalkyl, $OCF_3$, alkyl-OH, $NHSO_2R^9$, $COR^8$, $NHCOR^8$, and $NR^9R^{10}$;

$R^8$ is selected from H, $C_1$-$C_6$ alkyl, and $NR^9R^{10}$;

$R^9$ and $R^{10}$ may be the same or different and are selected from H and $C_1$-$C_6$ alkyl; and b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above;

Each $R^6$ may be the same or different and is selected from halo, OH, $C_1$-$C_6$ alkyl, $CF_3$, $C_1$-$C_6$ alkoxy, CN, $C_1$-$C_6$ alkyl-OH, $SO_2R_8$, $CO_2R_8$, $COR_8$, and $NHSO_2R_8$;

Each R' may be the same or different and is selected from OH, halo, CN, $NO_2$, $C_1$-$C_6$ alkyl, $C_1$-$C_6$ alkoxy, $CF_3$, $OCF_3$, alkyl-OH, $NHSO_2R_9$, $COR_8$, $NHCOR_8$, and $NR_9R_{10}$;

$R^8$ is selected from H, $C_1$-$C_6$ alkyl, $NR_9R_{10}$;

$R^9$ and $R^{10}$ may be the same or different and are selected from H and $C_1$-$C_6$ alkyl; and b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above,

Each $R^6$ may be the same or different and is selected from halo, OH, $C_1$-$C_6$ alkyl, substituted $C_1$-$C_6$ alkyl, $C_1$-$C_6$ haloalkyl, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

Each $R^7$ may be the same or different and is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ haloalkyl, $OCF_3$, alkyl-OH, $NHSO_2R^9$, $NHCOR^8$, and $NR^9R^{10}$;

$R^8$ is selected from H, $C_1$-$C_6$ alkyl, substituted $C_1$-$C_6$ alkyl, and $NR^9R^{10}$;

$R^9$ and $R^{10}$ may be the same or different and are selected from H, $C_1$-$C_6$ alkyl, and substituted $C_1$-$C_6$ alkyl;

b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above;

Each $R^6$ may be the same or different and is selected from halo, OH, $C_1$-$C_6$ alkyl, $C_1$-$C_6$ haloalkyl, $C_1$-$C_6$ alkoxy, CN, $C_1$-$C_6$ alkyl-OH, $SO_2R^8$, $CO_2R^8$, $COR^8$ and $NHSO_2R^8$;

Each $R^6$ may be the same or different and is selected from OH, halo, CN, $NO_2$, $C_1$-$C_6$ alkyl, $C_1$-$C_6$ alkoxy, $C_1$-$C_6$ haloalkyl, $OCF_3$, alkyl-OH, $NHSO_2R^9$, $NHCOR^8$, and $NR^9R^{10}$;

$R^8$ is selected from H, $C_1$-$C_6$ alkyl, and $NR^9R^{10}$;

$R^9$ and $R^{10}$ may be the same or different and are selected from H, and $C_1$-$C_6$ alkyl; and b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above;

Each $R^6$ may be the same or different and is selected from halo, OH, $C_1$-$C_6$ alkyl, substituted $C_1$-$C_6$ alkyl, $CF_3$, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

Each $R^7$ may be the same or different and is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $CF_3$, $OCF_3$, alkyl-OH, $NHSO_2R^9$, $NHCOR^8$, and $NR^9R^{10}$;

$R^8$ is selected from H, $C_1$-$C_6$ alkyl, substituted $C_1$-$C_6$ alkyl, and $NR^9R^{10}$;

$R^9$ and $R^{10}$ may be the same or different and are selected from H, $C_1$-$C_6$ alkyl, and substituted $C_1$-$C_6$ alkyl; and b and c are selected from 0, 1, 2 or 3.

In a particular embodiment, with respect to compounds according to any one of Formulae (IIIA)-(IIIC):

$R^2$, $R^4$ and $R^5$ are as defined for Formula (I) above;

Each $R^6$ may be the same or different and is selected from halo, OH, $C_1$-$C_6$ alkyl, $CF_3$, $C_1$-$C_6$ alkoxy, CN, $C_1$-$C_6$ alkyl-OH, $SO_2R^8$, $CO_2R^8$, $COR^8$, and $NHSO_2R^8$;

Each R' may be the same or different and is selected from OH, halo, CN, $NO_2$, $C_1$-$C_6$ alkyl, $C_1$-$C_6$ alkoxy, $CF_3$, $OCF_3$, alkyl-OH, $NHSO_2R^9$, $NHCOR^8$, and $NR^9R^{10}$;

$R^8$ is selected from H, $C_1$-$C_6$ alkyl, $NR^9R^{10}$;

$R^9$ and $R^{10}$ may be the same or different and are selected from H, and $C_1$-$C_6$ alkyl; and b and c are selected from 0, 1, 2 or 3.

In a particular embodiment, with respect to compounds according to any one of Formulae (IIIA)-(IIIC), $R^2$, $R^4$ and $R^5$ are selected from H, Me, and Et.

In a particular embodiment, with respect to compounds according to any one of Formulae (IIIA)-(IIIC), $R^2$, $R^4$ and $R^5$ are selected from H and Me.

In a particular embodiment, with respect to compounds according to any one of Formulae (IIIA)-(IIIC), $R^6$ is selected from halogen, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkyl-OH, $SO_2R^8$ and $COR^8$.

In a particular embodiment, with respect to compounds according to any one of Formulae (IIIA)-(IIIC), $R^6$ is selected from halogen, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkyl-OH, and $SO_2R^8$.

In a particular embodiment, with respect to compounds according to any one of Formulae (IIIA)-(IIIC), $R^6$ is selected from halogen, $C_1$-$C_6$ alkyl, $C_1$-$C_6$ alkoxy, $C_1$-$C_6$ alkyl-OH and $SO_2R^8$.

In a particular embodiment, with respect to compounds according to any one of Formulae (IIIA)-(IIIC), $R^6$ is selected from halogen, $C_1$-$C_6$ alkyl, $C_1$-$C_6$ alkoxy, $C_1$-$C_6$ alkyl-OH, $COR^8$ and $SO_2R^8$.

In a particular embodiment, with respect to compounds according to any one of Formulae (IIIA)-(IIIC), $R^6$ is $SO_2R^8$, where $R^8$ is $C_1$-$C_6$ alkyl or $NR^9R^{10}$.

In a particular embodiment, with respect to compounds according to any one of Formulae (IIIA)-(IIIC), $R^7$ is selected from OH, $NO_2$, $C_1$-$C_6$ alkoxy, substituted $C_1$-$C_6$ alkoxy, halogen, $C_1$-$C_6$ alkyl, substituted $C_1$-$C_6$ alkyl, $NR^9R^{10}$, $NHSO_2R^8$ and $NHCOR^8$.

In a particular embodiment, with respect to compounds according to any one of Formulae (IIIA)-(IIIC), R' is selected from OH, $NO_2$, $NH_2$, $C_1$-$C_6$ alkoxy, halogen, $C_1$-$C_6$ alkyl, $NHSO_2R^8$ and $NHCOR^8$; where $R^8$ is $C_1$-$C_6$ alkyl.

In a particular embodiment, with respect to compounds according to any one of Formulae (IIIA)-(IIIC), R' is selected from OH, $NO_2$, $NH_2$, and $COR^8$; where $R^8$ is $C_1$-$C_6$ alkyl.

In a particular embodiment, with respect to compounds according to any one of Formulae (IIIA)-(IIIC), R' is selected from OH, $NO_2$, $NH_2$, OMe, halogen, $NHSO_2R^8$ and $NHCOR^8$; where $R^8$ is $C_1$-$C_6$ alkyl.

In a particular embodiment, the compounds are according to Formula (IIIB) or (IIIC).

In a particular embodiment, the present invention relates to compounds according to Formula (IVA)-(IVB) below:

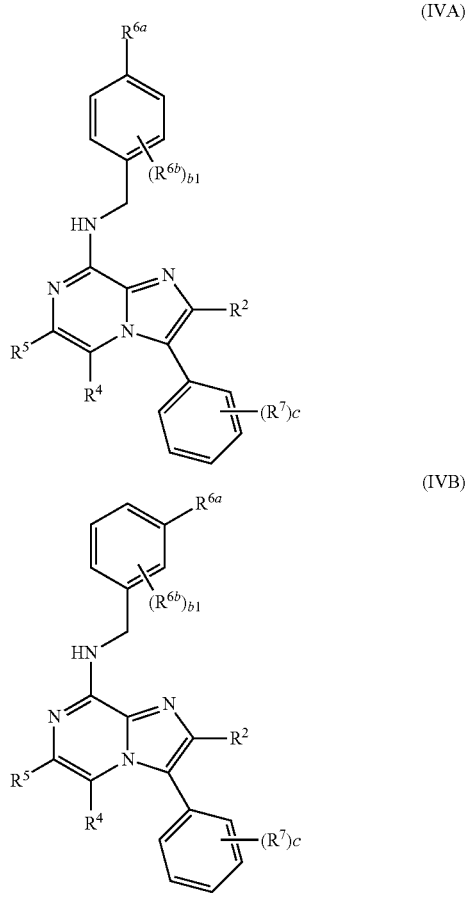

Wherein
$R^2$, $R^4$, $R^5$, and $R^7$ are as defined for Formulae (I) and (IIA)-(IIC) above;

$R^{6a}$ is selected from halo, OH, $C_1$-$C_6$ alkyl, substituted $C_1$-$C_6$ alkyl, $CF_3$, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

Each $R^{6b}$ may be the same or different and is selected from halo, OH, $C_1$-$C_6$ alkyl, substituted $C_1$-$C_6$ alkyl, $CF_3$, $C_1$-$C_6$ alkoxy, substituted $C_1$-$C_6$ alkoxy, CN, $C_1$-$C_6$ alkyl-OH, $SO_2R^8$, $CO_2R^8$, $COR^8$, and $NHSO_2R^8$;

b1 is 0, 1, or 2; and c is 0, 1, 2 or 3.

In a particular embodiment, with respect to compounds according to Formula (IVA) or (IVB), $R^2$, $R^4$ and $R^5$ are selected from H, Me, and Et.

In a particular embodiment, with respect to compounds according to Formula (IVA) or (IVB), $R^2$, $R^4$ and $R^5$ are selected from H and Me.

In a particular embodiment, with respect to compounds according to Formula (IVA) or (IVB), $R^{6a}$ is selected from halo, OH, $C_1$-$C_6$ alkyl, substituted $C_1$-$C_6$ alkyl, $CF_3$, $C_1$-$C_6$ alkoxy, substituted $C_1$-$C_6$ alkoxy, $C_1$-$C_6$ alkyl-OH and $SO_2R^8$, where $R^8$ is $C_1$-$C_6$ alkyl and $NR^9R^{10}$.

In a particular embodiment, with respect to compounds according to Formula (IVA) or (IVB), $R^{6a}$ is $SO_2R^8$, where $R^8$ is $C_1$-$C_6$ alkyl or $NR^9R^{10}$.

In a particular embodiment, with respect to compounds according to Formula (IVA) or (IVB), $R^{6a}$ is $SO_2R^8$, where $R^8$ is $NR^9R^{10}$ and $R^9$ and $R^{10}$ are each independently selected from H and $C_1$-$C_6$ alkyl.

In a particular embodiment, with respect to compounds according to Formula (IVA) or (IVB), $R^{6a}$ is $SO_2R^8$, where $R^8$ is $C_1$-$C_6$ alkyl.

In a particular embodiment, with respect to compounds according to Formula (IVA) or (IVB), $R^{6b}$ is selected from halogen, $C_1$-$C_6$ alkyl, $C_1$-$C_6$ alkoxy and OH.

In a particular embodiment, with respect to compounds according to any one of Formulae (IVA)-(IVC), $R^7$ is selected from OH, $NO_2$, $C_1$-$C_6$ alkoxy, substituted $C_1$-$C_6$ alkoxy, halogen, $C_1$-$C_6$ alkyl, substituted $C_1$-$C_6$ alkyl, $NR^9R^{10}$, $NHSO_2R^8$ and $NHCOR^8$.

In a particular embodiment, with respect to compounds according to any one of Formulae (IVA)-(IVC), $R^7$ is selected from OH, $NO_2$, $NH_2$, $C_1$-$C_6$ alkoxy, halogen, $C_1$-$C_6$ alkyl, $NHSO_2R^8$ and $NHCOR^8$; where $R^8$ is $C_1$-$C_6$ alkyl.

In a particular embodiment, with respect to compounds according to any one of Formulae (IVA)-(IVC), R' is selected from OH, $NO_2$, $NH_2$, and $COR^S$; where $R^8$ is $C_1$-$C_6$ alkyl.

In a particular embodiment, with respect to compounds according to any one of Formulae (IVA)-(IVC), R' is selected from OH, $NO_2$, $NH_2$, OMe, halogen, $NHSO_2R^8$ and $NHCOR^8$; where $R^8$ is $C_1$-$C_6$ alkyl.

In a particular embodiment, the present invention relates to compounds according to Fomulae (VA)-(VB) below:

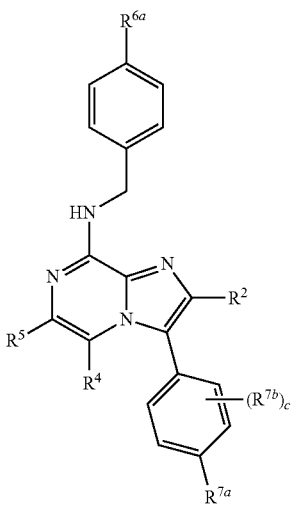

(VA)

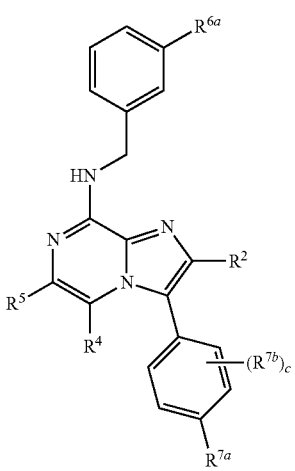

(VB)

Wherein
- $R^2$, $R^4$, $R^5$, and $R^{6a}$ are as defined for Formulae (I) and (IIA)-(IIC) above;
- $R^{7a}$ is selected from H, OH, $OCH_3$, halogen, $NH_2$, $CH_2$—OH and $NHCOR_8$;
- each $R^{7b}$ is selected from OH, halo, CN, $NO_2$, $C_1$-$C_6$ alkyl, substituted $C_1$-$C_6$ alkyl, $C_1$-$C_6$ alkoxy, substituted $C_1$-$C_6$ alkoxy, $CF_3$, $OCF_3$, alkyl-OH, $NHSO_2R^9$, $NHCOR^8$, and $NR^9R^{10}$;
- $R^8$ is selected from H, $C_1$-$C_6$ alkyl, substituted $C_1$-$C_6$ alkyl, and $NR^9R^{10}$;
- $R^9$ and $R^{10}$ may be the same or different and are selected from H, $C_1$-$C_6$ alkyl, and substituted $C_1$-$C_6$ alkyl; and
- c1 is 0 or 1.

In a particular embodiment, with respect to compounds according to Formula (VA) or (VB), $R^2$, $R^4$ and $R^5$ are selected from H, Me, and Et.

In a particular embodiment, with respect to compounds according to Formula (VA) or (VB), $R^2$, $R^4$ and $R^5$ are selected from H and Me.

In a particular embodiment, with respect to compounds according to Formula (VA) or (VB), $R^{6a}$ is selected from halo, OH, $C_1$-$C_6$ alkyl, substituted $C_1$-$C_6$ alkyl, $CF_3$, $C_1$-$C_6$ alkoxy, substituted $C_1$-$C_6$ alkoxy, $C_1$-$C_6$ alkyl-OH and $SO_2R^8$, where $R^8$ is $C_1$-$C_6$ alkyl or $NR^9R^{10}$.

In a particular embodiment, with respect to compounds according to Formula (VA) or (VB), $R^{6a}$ is $SO_2R^8$, where $R^8$ is $C_1$-$C_6$ alkyl or $NR^9R^{10}$.

In a particular embodiment, with respect to compounds according to Formula (VA) or (VB), $R^{6a}$ is $SO_2R^8$, where $R^8$ is $NR^9R^{10}$ and $R^9$ and $R^{10}$ are each independently selected from H and $C_1$-$C_6$ alkyl.

In a particular embodiment, with respect to compounds according to Formula (VA) or (VB), $R^{6a}$ is $SO_2R^8$, where $R^8$ is $C_1$-$C_6$ alkyl.

In a particular embodiment, with respect to compounds according to Formula (VA) or (VB), $R^{6b}$ is selected from halogen, $C_1$-$C_6$ alkyl, $C_1$-$C_6$ alkoxy and OH.

In a particular embodiment, with respect to compounds according to Formula (VA) or (VB), $R^{7a}$ is selected from H, OH, $NH_2$ and OMe.

In a particular embodiment, with respect to compounds according to Formula (VA) or (VB), $R^{7b}$ is selected from OH, halo, $NO_2$, $NH_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkyl-OH, $NHSO_2R^9$ and $NHCOR^8$.

In a particular embodiment, with respect to compounds according to Formula (VA) or (VB), $R^{7b}$ is selected from OH, halo, $NO_2$, $NH_2$, $C_1$-$C_6$ alkyl, $C_1$-$C_6$ alkoxy, $C_1$-$C_6$ alkyl-OH, $NHSO_2R^9$ and $NHCOR^8$.

In a particular embodiment, with respect to compounds according to Formula (VA) or (VB), c1 is 0.

In a particular embodiment, the present invention relates to compounds according to Formula (VIA)-(VIB) below:

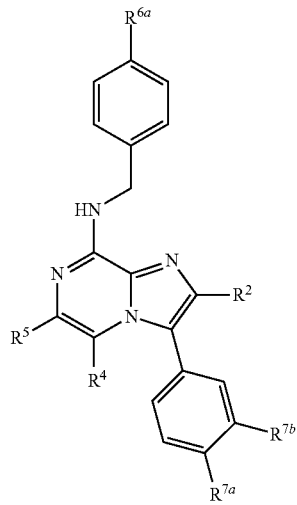

(VIA)

-continued

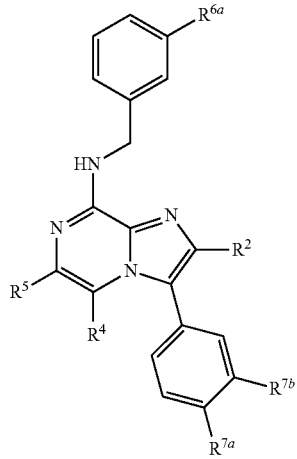
(VIB)

Wherein
$R^2$, $R^4$, $R^5$, are as defined for Formula (I) above;
$R^{6a}$ is selected from H, $SO_2R_8$, $NHSO_2R_8$, $CO_2H$ and $CH_2OH$;
$R^8$ is selected from H, alkyl and $NR^9R^{10}$;
$R^9$ and $R^{10}$ may be the same or different and are selected from H and alkyl;
$R^{7b}$ is selected from H, OH, halogen, $OCH_3$, $CF_3$, $OCF_3$, $NO_2$, $CH_3$, $CH_2$—OH, $CH_3$, —$NHSO_2R^8$ and —$COR_8$; and
$R^{7a}$ is selected from H, OH, $OCH_3$, halogen, $NH_2$, —$CH_2$—OH and —$NHCOR^8$.

In a particular embodiment, with respect to compounds according to Formula (VIA)-(VIB), $R^2$, $R^4$ and $R^5$ are selected from H, Me, and Et.

In a particular embodiment, with respect to compounds according to Formula (VIA)-(VIB), $R^2$, $R^4$ and $R^5$ are selected from H and Me.

In a particular embodiment, with respect to compounds according to Formula (VIA)-(VIB), $R^{6a}$ is $SO_2R^8$, where $R^8$ is $C_1$-$C_6$ alkyl.

In a particular embodiment, with respect to compounds according to Formula (VIA)-(VIB), $R^{6a}$ is $SO_2R^8$, where $R^8$ is $NR^9R^{10}$.

In a particular embodiment, with respect to compounds according to Formula (VIA)-(VIB), $R^{6a}$ is $SO_2R^8$, where $R^8$ is $NR^9R^{10}$ and $R^9$ and $R^{10}$ are each independently selected from H and $C_1$-$C_6$ alkyl.

In a particular embodiment, with respect to compounds according to Formula (VIA)-(VIB), $R^{7a}$ is selected from H, OH, $NH_2$ and OMe.

In a particular embodiment, the present invention relates to compounds according to Formula (VIIA)-(VIIB) below:

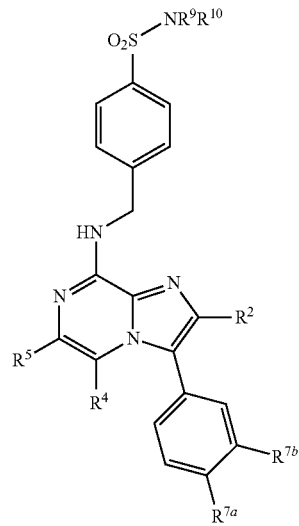
(VIIA)

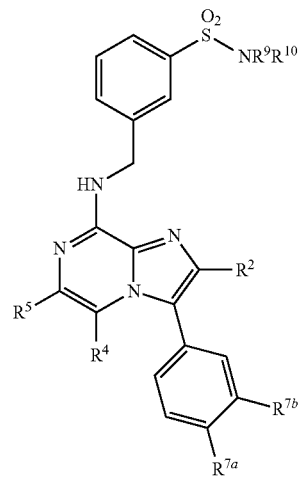
(VIIB)

Wherein:
$R^2$, $R^4$, and $R^5$ are as defined for Formulae (I) above;
$R_9$ and $R_{10}$ may be the same or different and are selected from H and alkyl;
$R^{7b}$ is selected from H, OH, halogen, $OCH_3$, $CF_3$, $OCF_3$, $NO_2$ and $CH_3$; and
$R^{7a}$ is selected from H, OH, $OCH_3$, halogen and $NH_2$.

In a particular embodiment, with respect to compounds according to Formula (VIIA) or (VIIB)
$R^2$, $R^4$, and $R^5$ are as defined for Formulae (I) above;
$R_9$ and $R_{10}$ may be the same or different and are selected from H and $C_1$-$C_6$ alkyl;
$R^{7b}$ is selected from H, OH, halogen, $OCH_3$, $CF_3$, $OCF_3$, $NO_2$ and $CH_3$; and
$R^{7a}$ is selected from H, OH, $OCH_3$, halogen and $NH_2$.

In a particular embodiment, with respect to compounds according to Formula (VIIA) or (VIIB)
$R^2$, $R^4$, and $R^5$ are as defined for Formulae (I) above;
$R_9$ and $R_{10}$ may be the same or different and are selected from H and $C_1$-$C_6$ alkyl;
$R^{7b}$ is selected from H, OH, halogen, $OCH_3$, $NO_2$ and $CH_3$; and
$R^{7a}$ is selected from H, OH, $OCH_3$, halogen and $NH_2$.

In a particular embodiment, with respect to compounds according to any one of Fomulae (VIA), (VIB), (VIIA) and (VIIB) described above $R_2$, $R_4$ and $R_5$ are selected from H, Me, and Et.

In a particular embodiment, with respect to compounds according to any one of Fomulae (VIA), (VIB), (VIIA) and (VIIB) described above $R_2$, $R_4$ and $R_5$ are selected from H and Me.

In a particular embodiment, with respect to compounds according to any one of Formulae (VIA), (VIB), (VIIA) and (VIIB) above, $R^2$, $R^4$ and $R^5$ are H.

In a particular embodiment, with respect to compounds according to any one of Formulae (VIA), (VIB), (VIIA) and (VIIB) above, $R^2$ and $R^4$ are both H and $R^5$ is Me.

In a particular embodiment, with respect to compounds according to any one of Formulae (VIA), (VIB), (VIIA) and (VIIB) above, $R^2$ is H, $R^4$ is Me and $R^5$ is H.

In a particular embodiment, with respect to compounds according to any one of Formulae (VIA), (VIB), (VIIA) and (VIIB)above, $R^2$ is Me, $R^4$ is H and $R^5$ is H.

In a particular embodiment, with respect to compounds according to Formula (VIA)-(VIB), $R^{7a}$ is selected from H, OH, and OMe.

In a particular embodiment the present invention relates to a compound selected from:

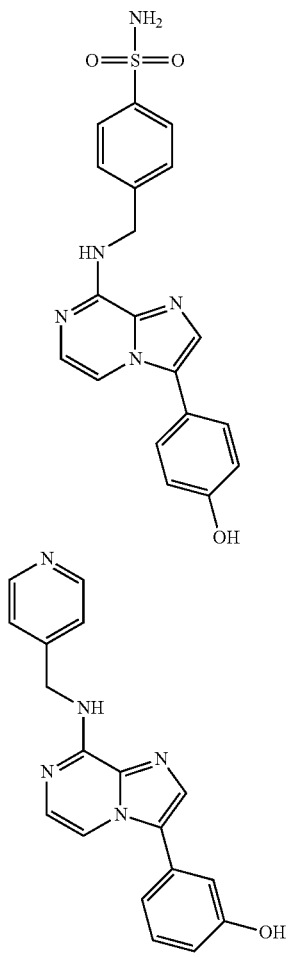

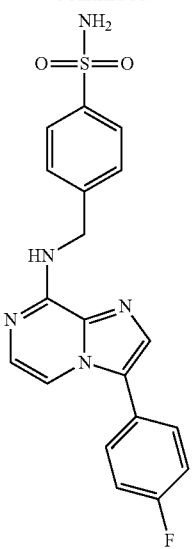

-continued

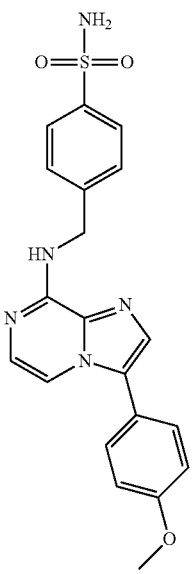

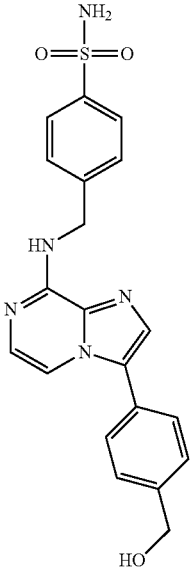

33
-continued
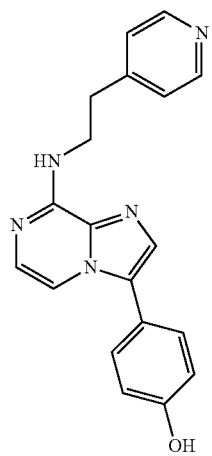
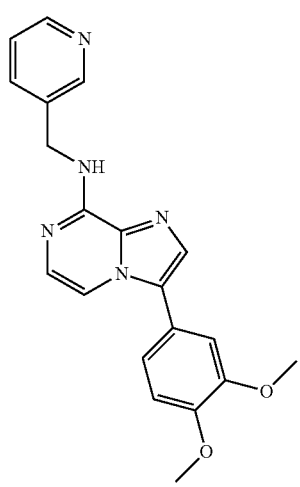
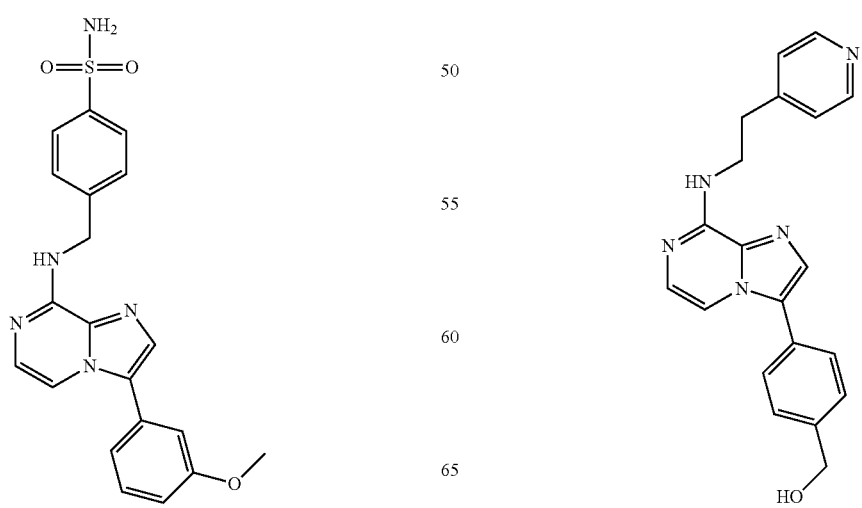
34
-continued
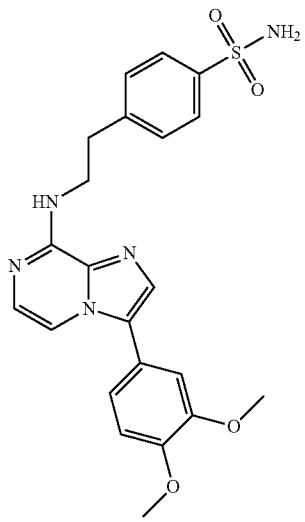

35
-continued
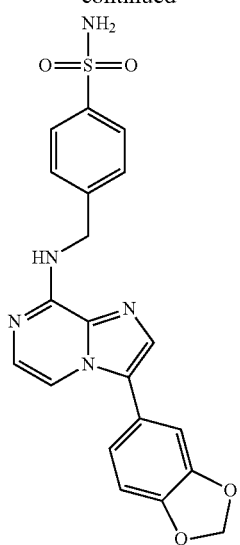
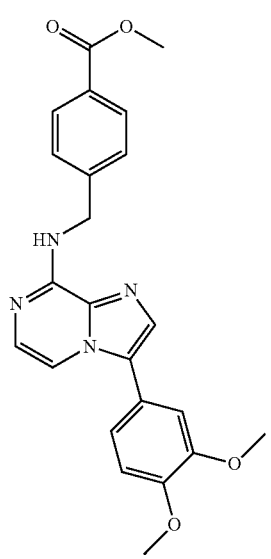
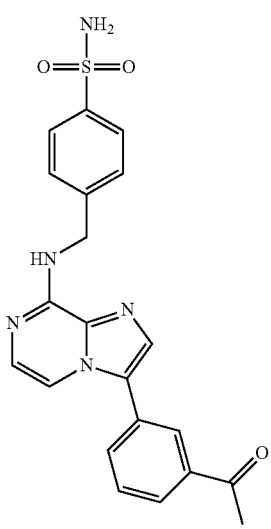
36
-continued
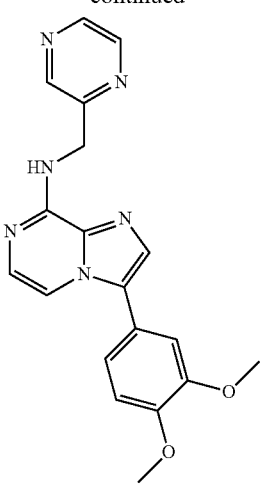
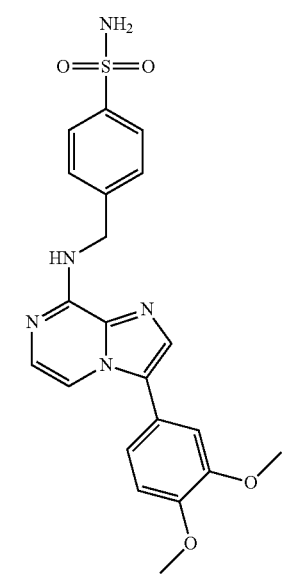

37
-continued
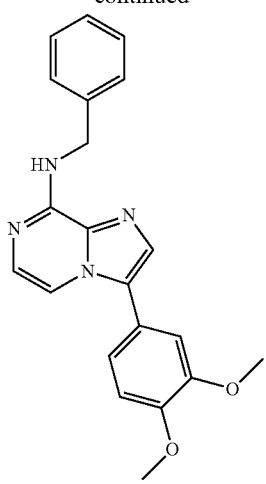
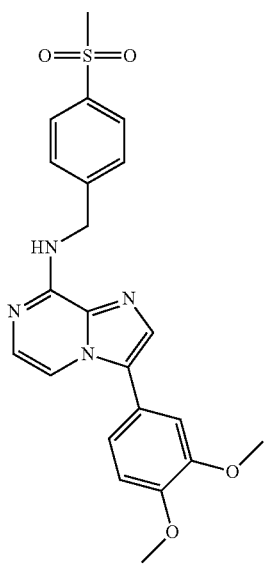
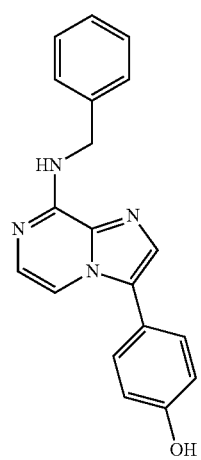
38
-continued
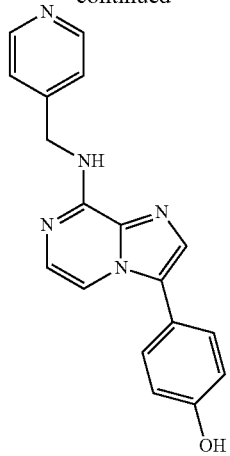
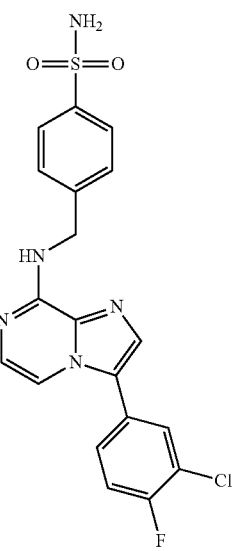
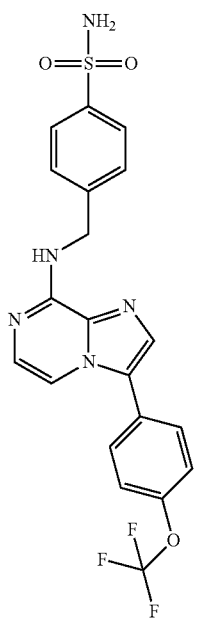

-continued
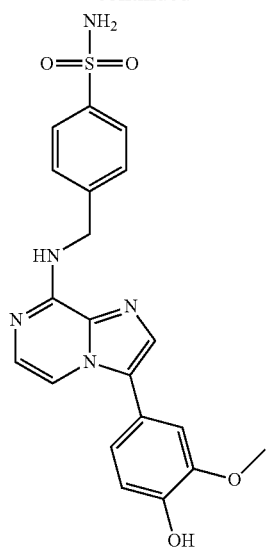
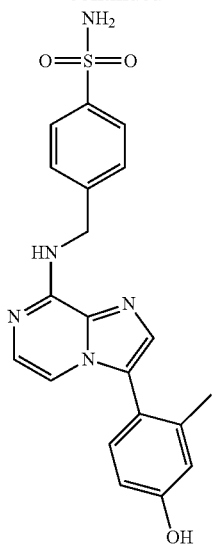
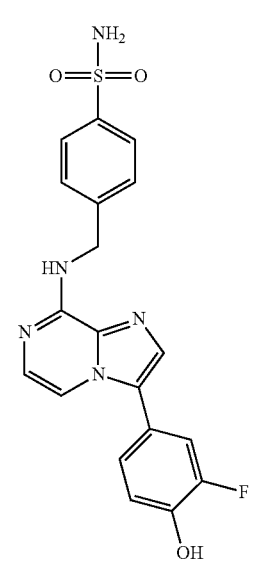
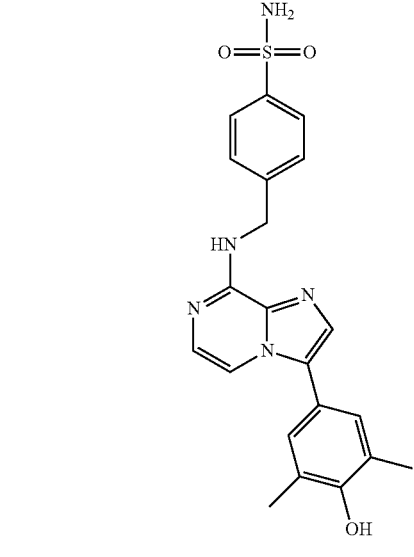
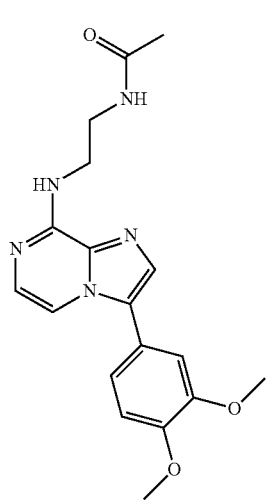
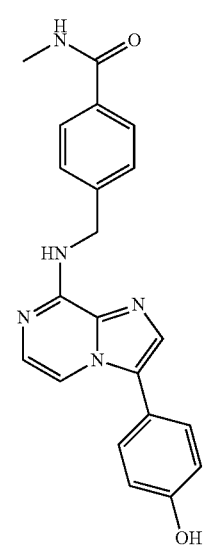

| 41 -continued | 42 -continued |
|---|---|
| 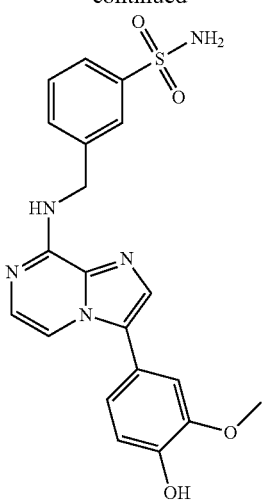 | 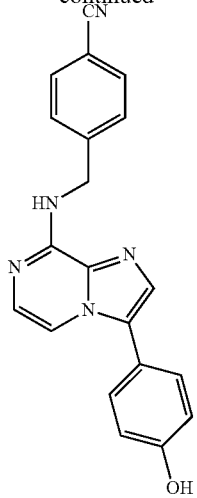 |
| 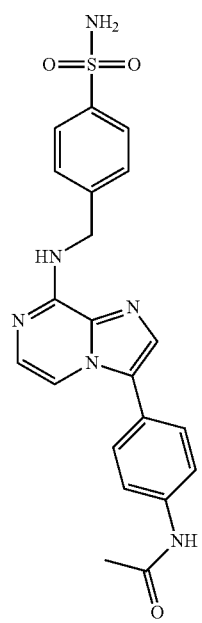 | 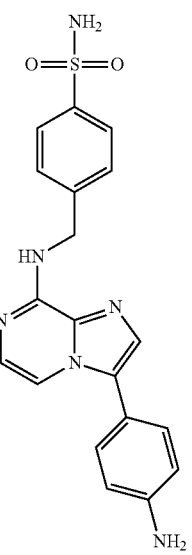 |
| 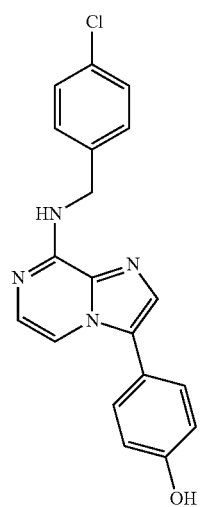 | 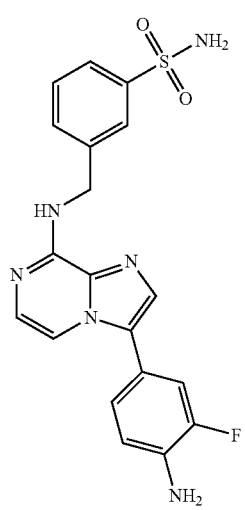 |

43
-continued
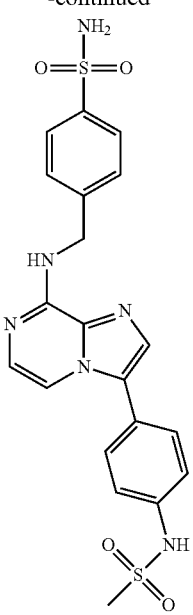
44
-continued
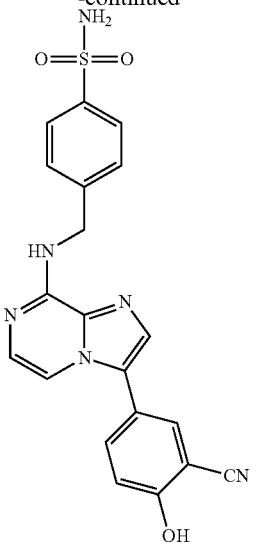
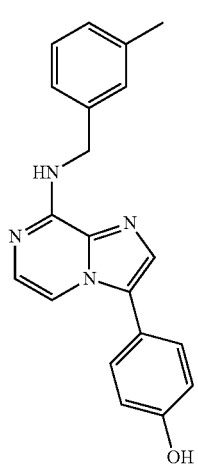
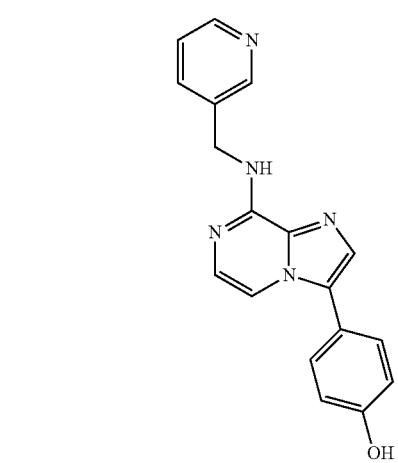
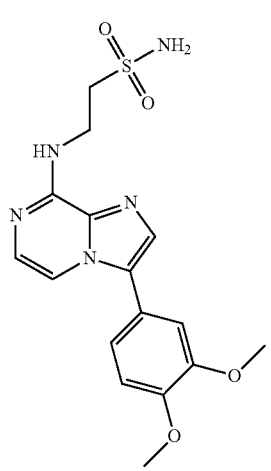
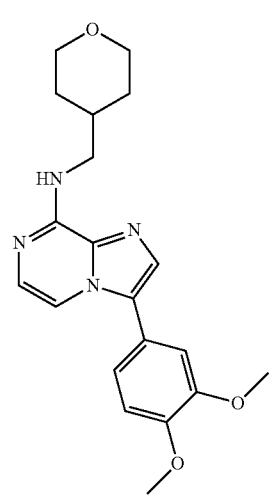

45
-continued
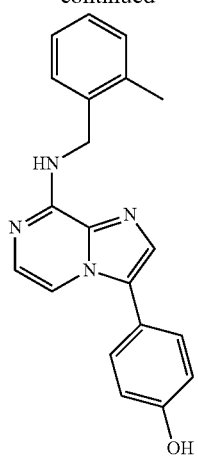
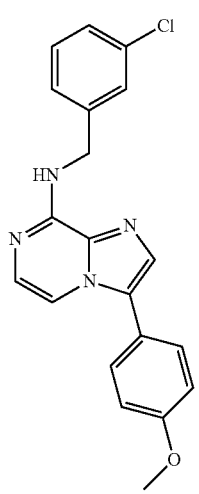
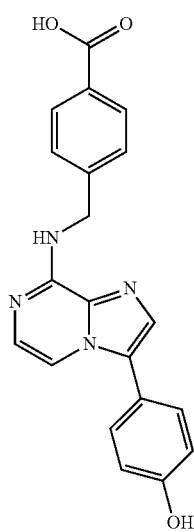
46
-continued
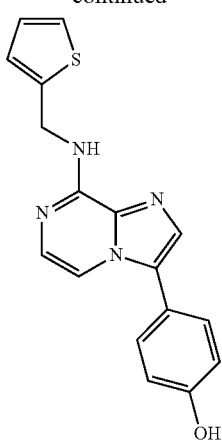
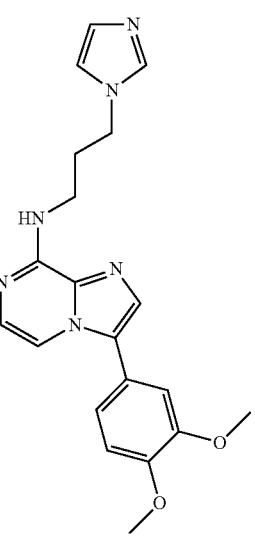
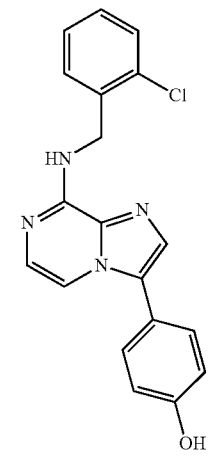

47
-continued
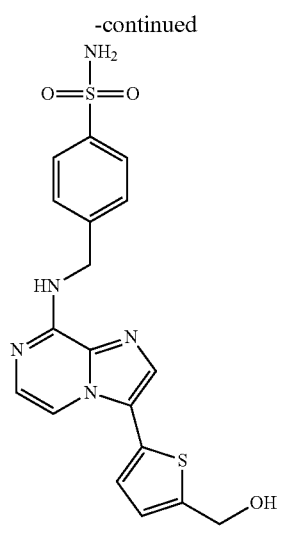
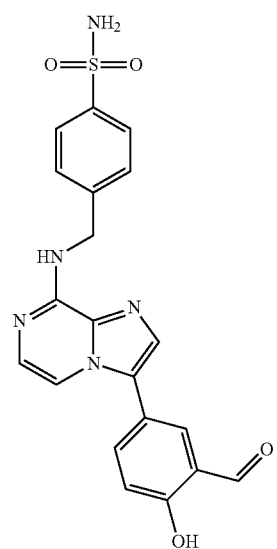
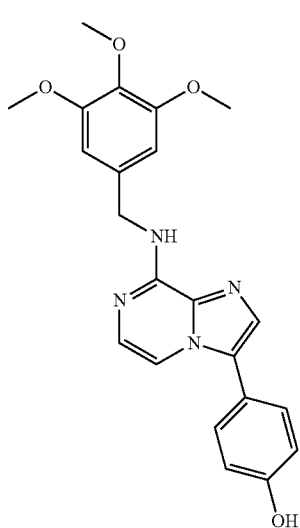
48
-continued
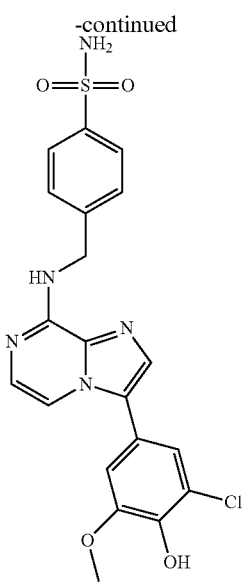
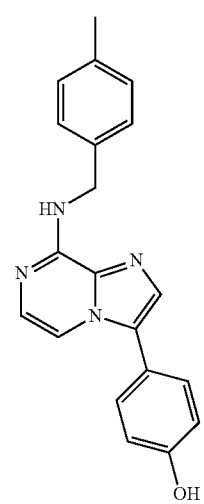
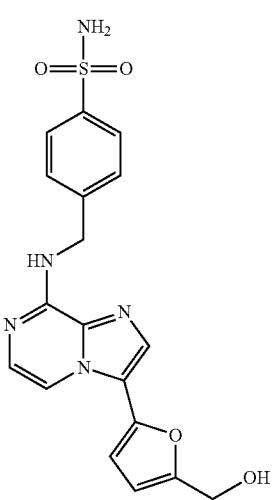

49
-continued
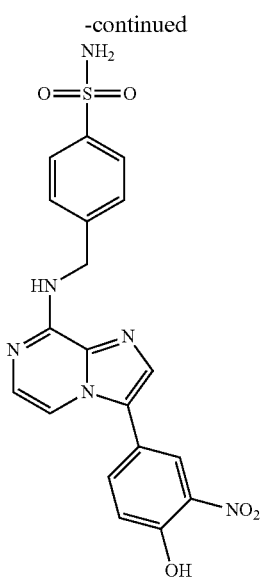
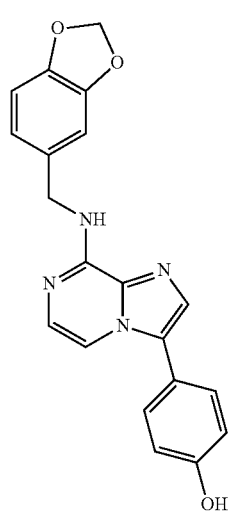
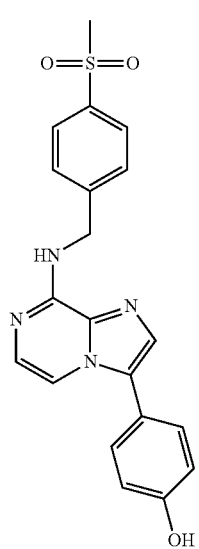
50
-continued
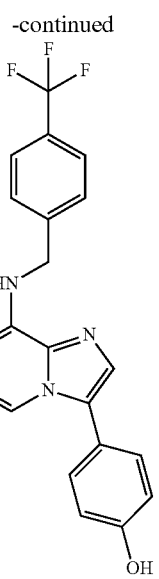
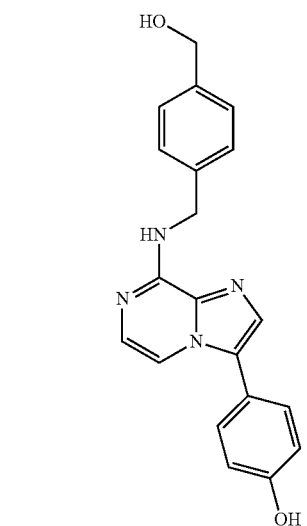
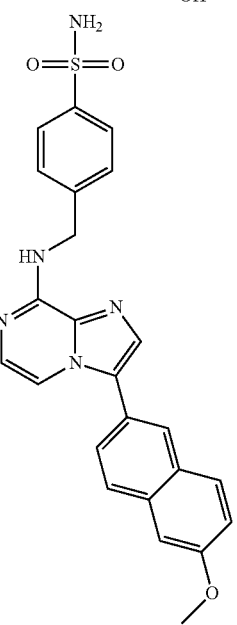

51
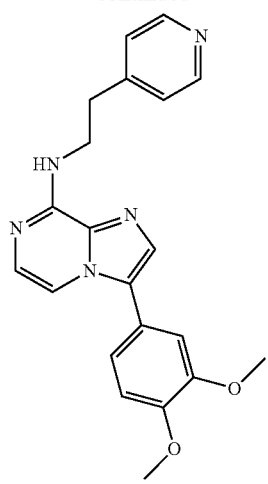
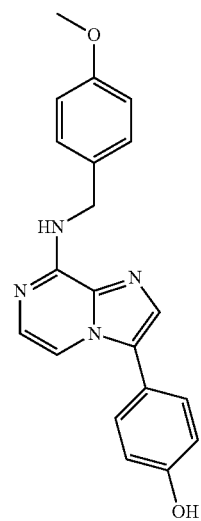
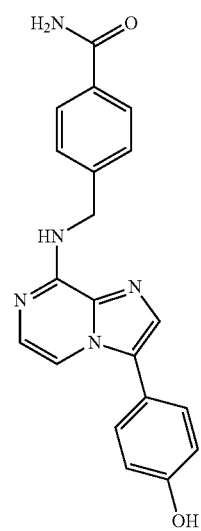
52
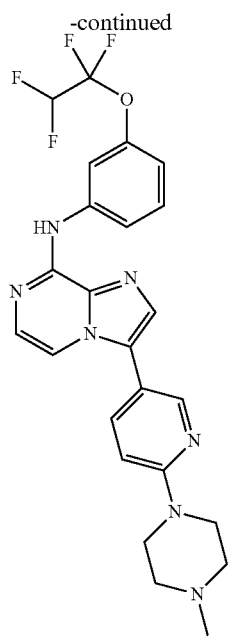
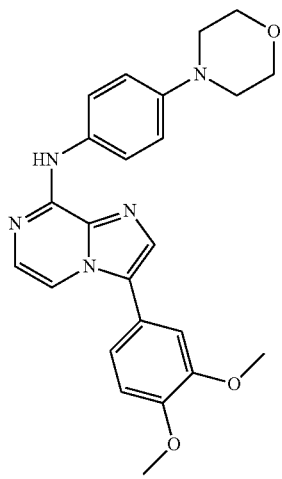
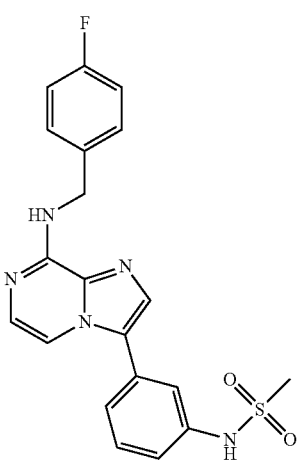

53
-continued
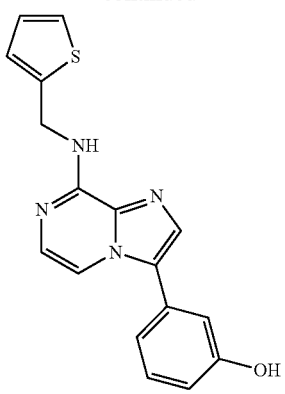
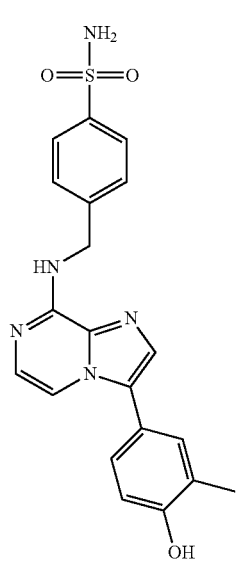
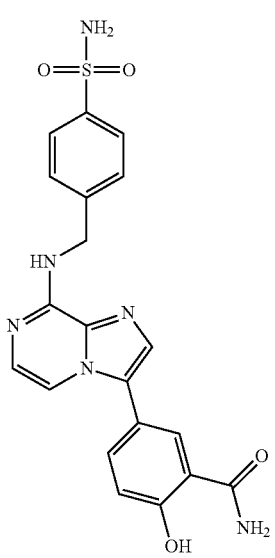
54
-continued
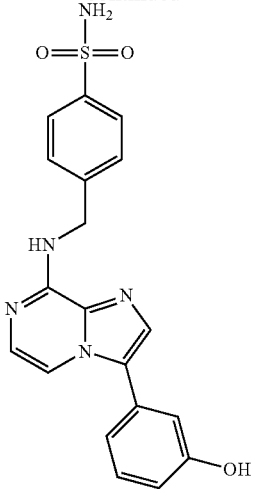
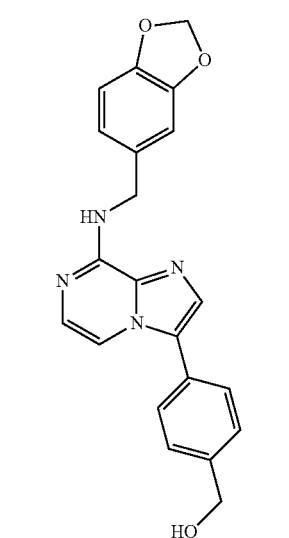

55
-continued
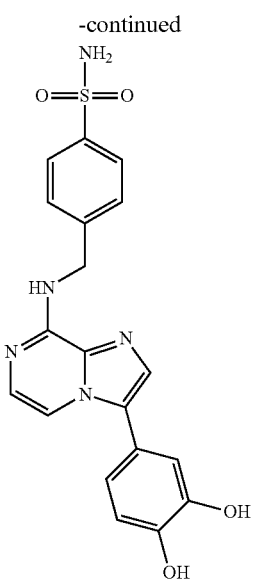
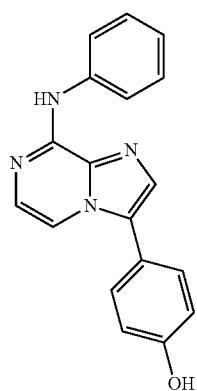
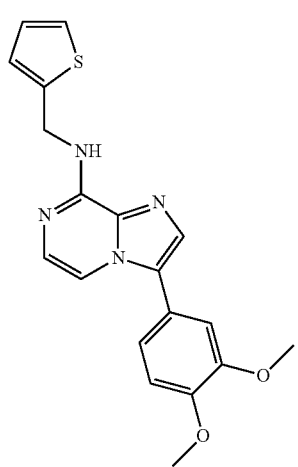
56
-continued
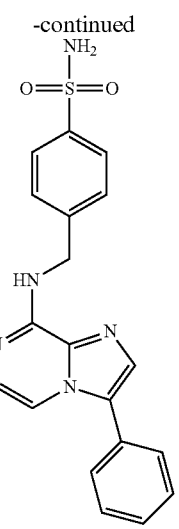
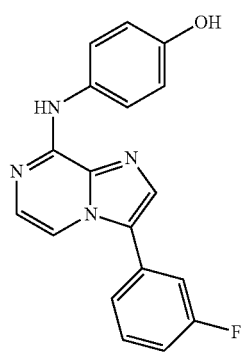
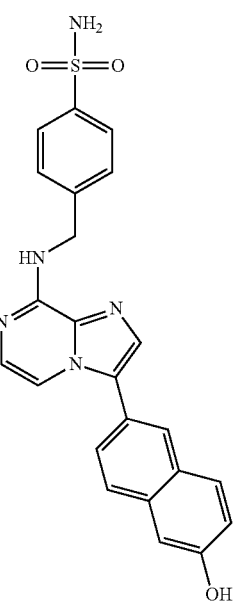

57
-continued
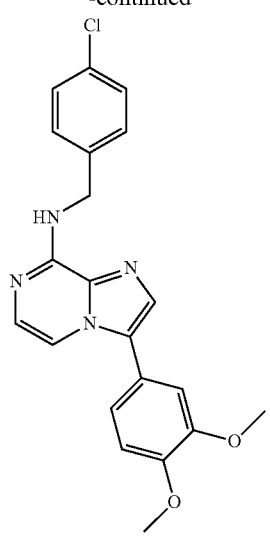
58
-continued
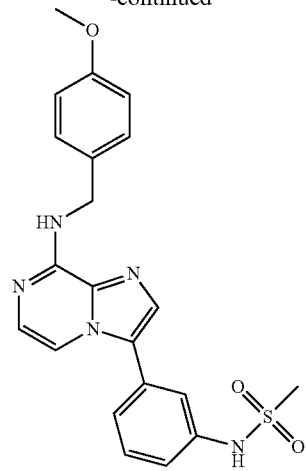
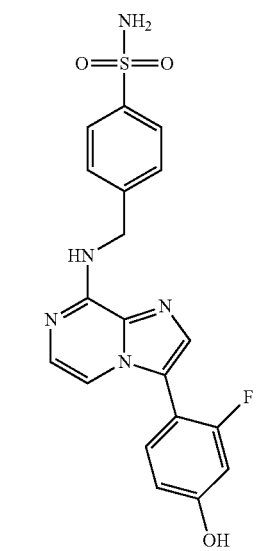
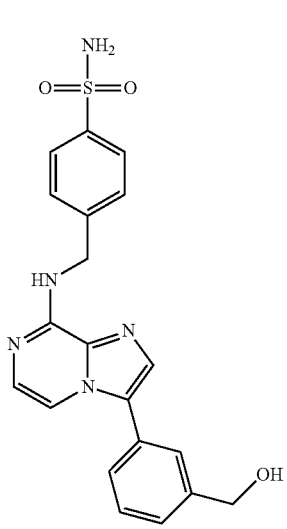
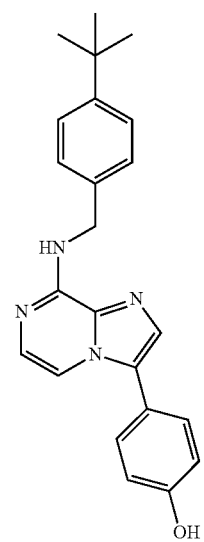

59
-continued
60
-continued
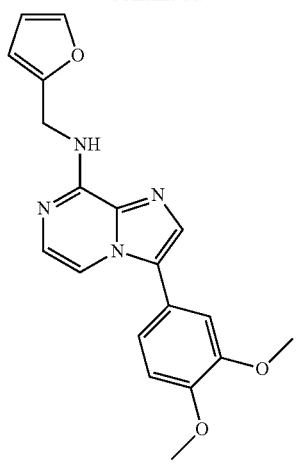
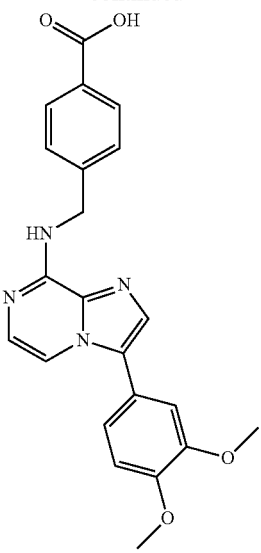
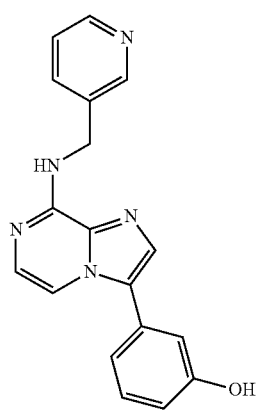
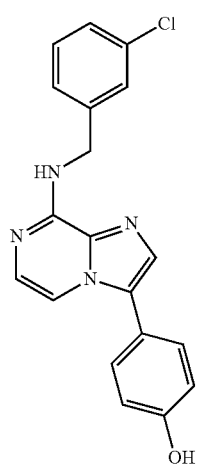
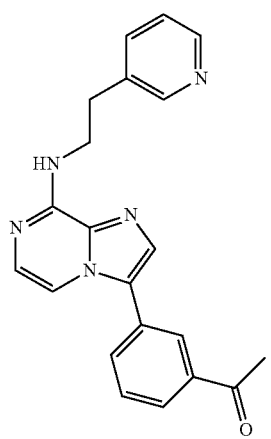
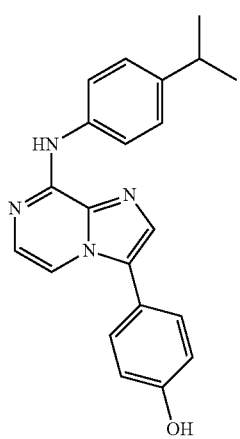

-continued
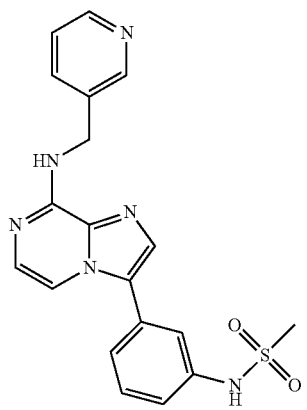
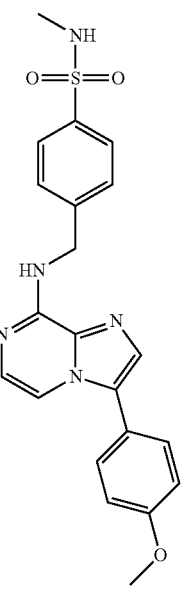
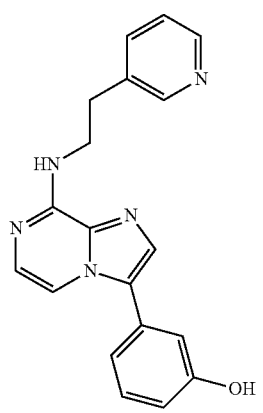
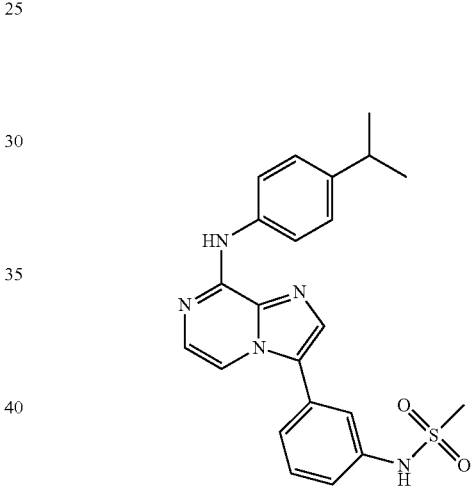
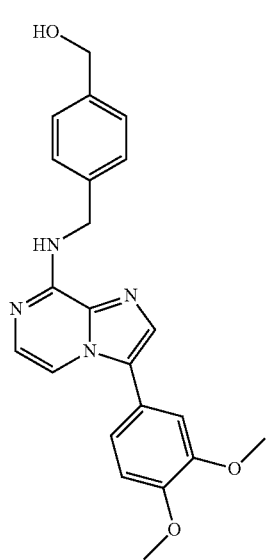
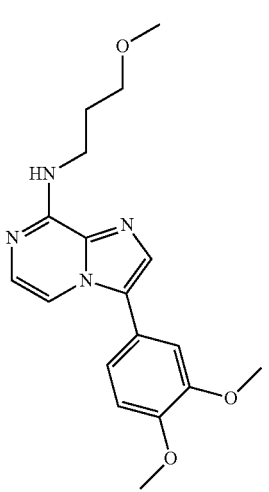

63
-continued
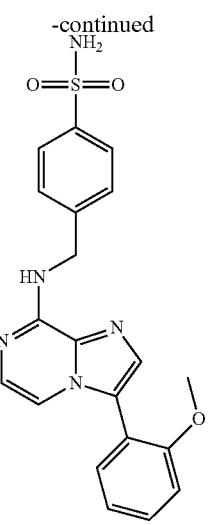
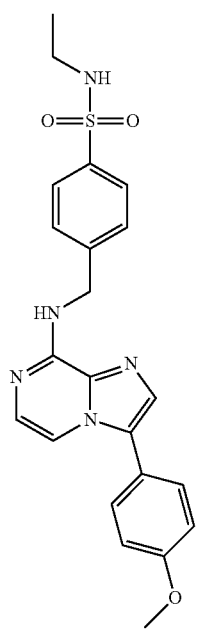
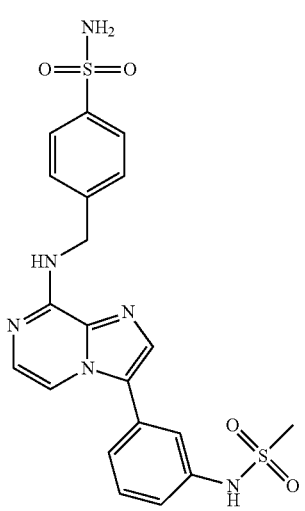
64
-continued
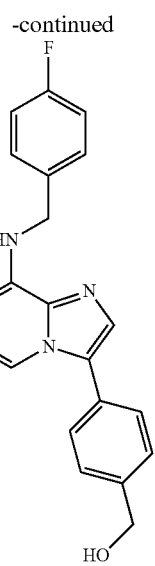
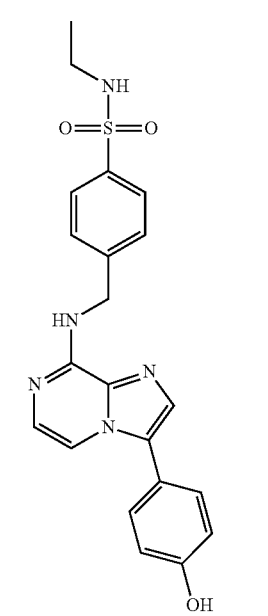

65
-continued
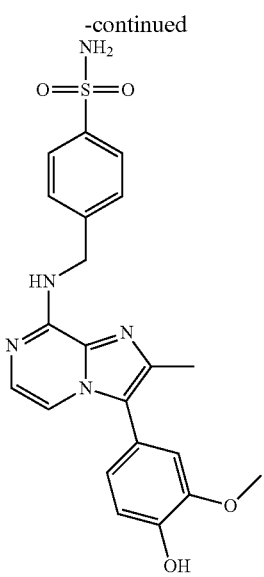
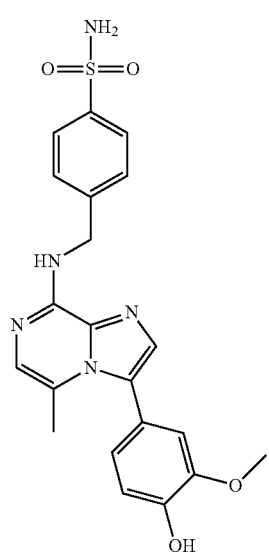
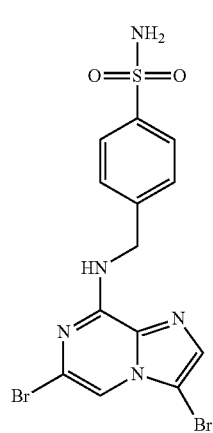
66
-continued
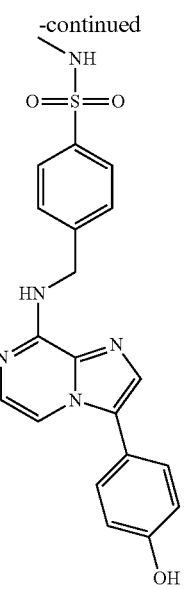
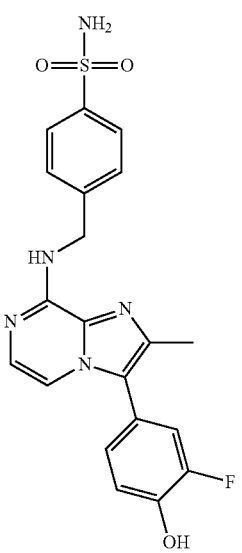
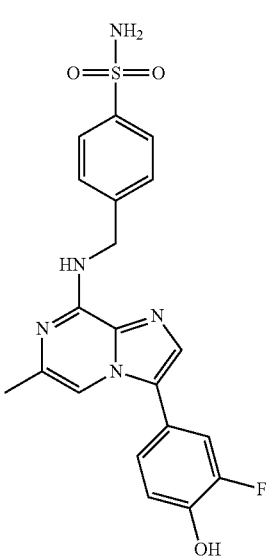

-continued

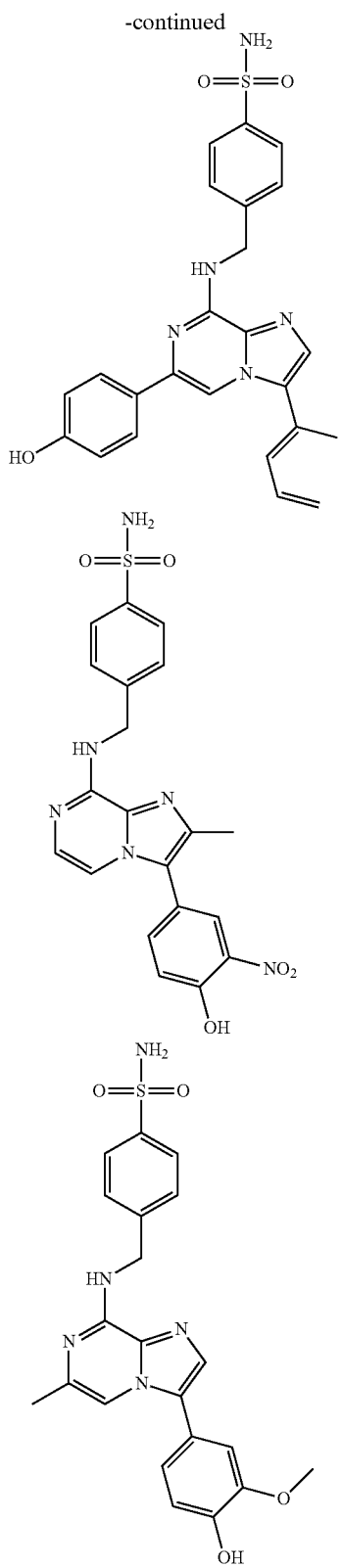

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

In yet another embodiment, the present application provides a combination pharmaceutical composition comprising: a) a first pharmaceutical composition comprising a compound of the present invention, or a pharmaceutically acceptable salt thereof; and b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In a particular embodiment, the present invention provides that one or more compounds of the present invention may be combined with one or more compounds selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231 B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib). It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations. Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g. 1-12 hours), by administration of a unit dose of one or more other active agents. In other cases, it may be desirable to administer a unit dose of one or more other active agents first, followed, after a period of hours (e.g. 1-12 hours), by administration of a unit dose of a compound of the invention.

The combination therapy may provide "synergy" or "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

The following formulation examples illustrate representative pharmaceutical compositions that may be prepared according to the present invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/mL.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of viral infections in mammals, in particular the treatment of flaviviruses and other positive strand RNA viruses such as picornaviruses. More particularly the present invention provides compounds that may be used as therapeutic agents for the treatment of flaviviruses and picornaviruses, in particular HCV, HRV, Sb, and/or CVB, more particularly in the treatment of HCV. Accordingly, the compounds and pharmaceutical compositions of this invention find use as therapeutics for preventing and/or treating viral infections in mammals including humans.

In a method of treatment aspect, this invention provides a method of treatment or prophylaxis in a mammal susceptible to or afflicted with a viral infection, for example a flavivirus such as HCV and other positive-strand RNA viruses, such as the picornaviruses poliovirus (Sb-1) and coxsackie B virus (CVB-2) which method comprises administering a therapeutically effective amount of a compound according to the invention, or one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

In a further embodiment, the present invention provides a compound of the invention for use in the treatment or prevention of a viral infection. In particular, the present invention provides a compound of the invention for use in the treatment or prevention of flaviviruses or picornaviruses. More particularly, the present invention provides a compound of the invention for use in the treatment and/or prevention of HCV, HRV, Sb and/or CVB. More particularly the present invention provides a compound of the invention for use in the treatment and/or prevention of HCV.

In yet another embodiment, the present application provides for a compound of the invention for use in preventing and/or treating a viral infection by administering a combination comprising a) a first pharmaceutical composition comprising a compound of the present invention, or a pharmaceutically acceptable salt thereof; and b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In yet another embodiment, the present application provides for a compound of the invention for use in preventing and/or treating a viral infection by administering a combination comprising a) a first pharmaceutical composition comprising a compound of the present invention, or a pharmaceutically acceptable salt thereof; and b) one or more compounds selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231 B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a viral infection, the compounds of this invention will be administered to a patient at risk for developing the condition, typically on the advice and under the supervision of a physician, at the dosage levels described above. Patients at risk for developing a particular viral infection generally include those that have been exposed to the virus in question or those who have been identified by genetic testing or screening to be particularly susceptible to developing the viral infection.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The imidazopyrazine compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; however, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative imidazopyrazine compounds that have been listed hereinabove. The compounds of the invention may be prepared from known or commercially available starting materials and reagents by one skilled in the art of organic synthesis.

EXAMPLES

Representative compounds of Formula (I) may be prepared according to the synthetic routes outlined below.

General Method 1

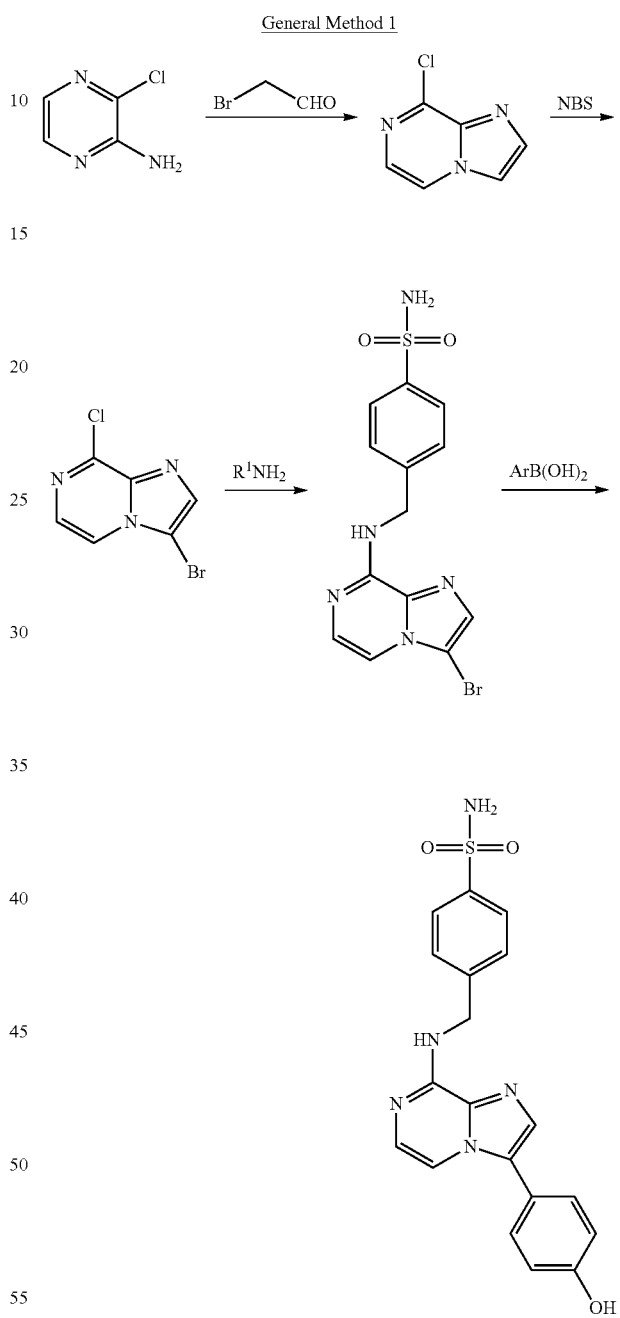

8-Chloro-imidazo[1,2-a]pyrazine

Bromoacetaldehyde diethyl acetal (200 mL, 1.3 mol) and a solution of 48% HBr (48 ml) are heated at reflux for 1.5 hours, then poured onto a suspension of $NaHCO_3$ (100 g) in propan-2-ol (1.6 L). The resulting solid is filtered off and 2-amino-3-chloropyrazine (51.8 g, 0.4 mol) is added to the solution then heated to reflux, during which time a clear solution forms which precipitates over 2 hours. The reaction mixture is cooled and allowed to stand overnight, and the solid may be collected by filtration and washed with propan-2-ol and Et$_2$O. The solid is added to a saturated solution of NaHCO$_3$ (500 mL) and DCM (1 L). The aqueous layer is separated from the organic solvent and re-extracted with DCM (2×250 mL). The organic layers are combined and dried over MgSO$_4$, filtered and evaporated to dryness, to afford a light brown solid. The propan-2-ol and Et$_2$O liquors from washing the filter cake, are evaporated to give a pale brown solid which is washed with a saturated solution of NaHCO$_3$ and extracted with DCM (X 3). The two solids were combined to afford compound 8-chloro-imidazo[1,2-a]pyrazine (59.1 g, 96%).

3-Bromo-8-chloro-imidazol[1,2-a]pyrazine

To a solution of 8-chloro-imidazo[1,2-a]pyrazine (1.53 g, 0.01 mol) in DCM (30 mL) is added N-bromosuccinimide (1.78 g, 0.01 mol) and the reaction is stirred at room temperature for 2 h. After this time the solution is washed with saturated aqueous solution of Na$_2$CO$_3$ (2×20 mL), dried (MgSO$_4$), filtered and concentrated in vacuo to give 3-bromo-8-chloro-imidazo[1,2-a]pyrazine (2.11 g, 96%).

4-[(3-Bromo-imidazo[1,2-a]pyrazin-8-ylamino)-methyl]-benzenesulfonamide

To a solution of 3-bromo-8-chloro-imidazo[1,2-a]pyrazine (2 g, 8.6 mmol) in $^t$BuOH (5 ml) is added 4-aminomethyl-benzenesulfonamide hydrochloride (2.1 g, 9.5 mmol) and DIPEA (3.7 ml, 21.5 mmol). The reaction is heated to 108° C. and stirred for 16 h. After this time the solution is allowed to cool, resulting in a thick white precipitate. The precipitate is filtered and washed with diethyl ether to give 4-[(3-Bromo-imidazo[1,2-a]pyrazin-8-ylamino)-methyl]-benzenesulfonamide as a white solid (1.24 g, 38%)

Compound 1: 4-{[3-(4-Hydroxy-phenyl)-imidazol[1,2-a]pyrazin-8-ylamino]-methyl}-benzenesulfonamide To a 5 mL microwave tube is added 4-[(3-Bromo-imidazo[1,2-a]pyrazin-8-ylamino)-methyl]-benzenesulfonamide (0.14 g, 0.379 mmol), 4-(4,4,5,5-Tetramethyl-[1,3,2]dioxaborolan-2-yl)-phenol (0.084 g, 0.417 mmol), Na$_2$CO$_3$ (0.1 g, 0.95 mmol), Pd(OAc)$_2$ (approx. 7 mg, 0.028 mmol), and (oxidi-2,1-phenylene)bis(diphenylphosphine) (20 mg, 0.038 mmol). The mixture is suspended in DMF (3 mL) and water (1 mL) and the vessel is sealed under a nitrogen atmosphere. The reaction vessel is heated to 130° C. in the CEM microwave for 20 min then allowed to cool and filtered through Celite and washed with EtOAc. The filtrate is evaporated and the residue taken up in DMSO and purified by prep HPLC. The product, 4-{[3-(4-Hydroxy-phenyl)-imidazo[1,2-a]pyrazin-8-ylamino]-methyl}-benzenesulfonamide, is obtained as a white solid (32 mg, 19%) (LC-MS m/z 396 [M+H]$^+$).

Examples 2-63

Using essentially the same procedures as described for General Method 1 and Compound I the compounds in Table 1 may be prepared,

TABLE 1

| Compound # | Structure | LC-MS:MH$^+$ |
|---|---|---|
| 1 | (structure) | m/z 396 [M + H]$^+$ |
| 2 | (structure) | m/z 332 [M + H]$^+$ |
| 3 | (structure) | m/z 346 [M + H]$^+$ |

TABLE 1-continued
| Compound # | Structure | LC-MS:MH+ |
|---|---|---|
| 4 | 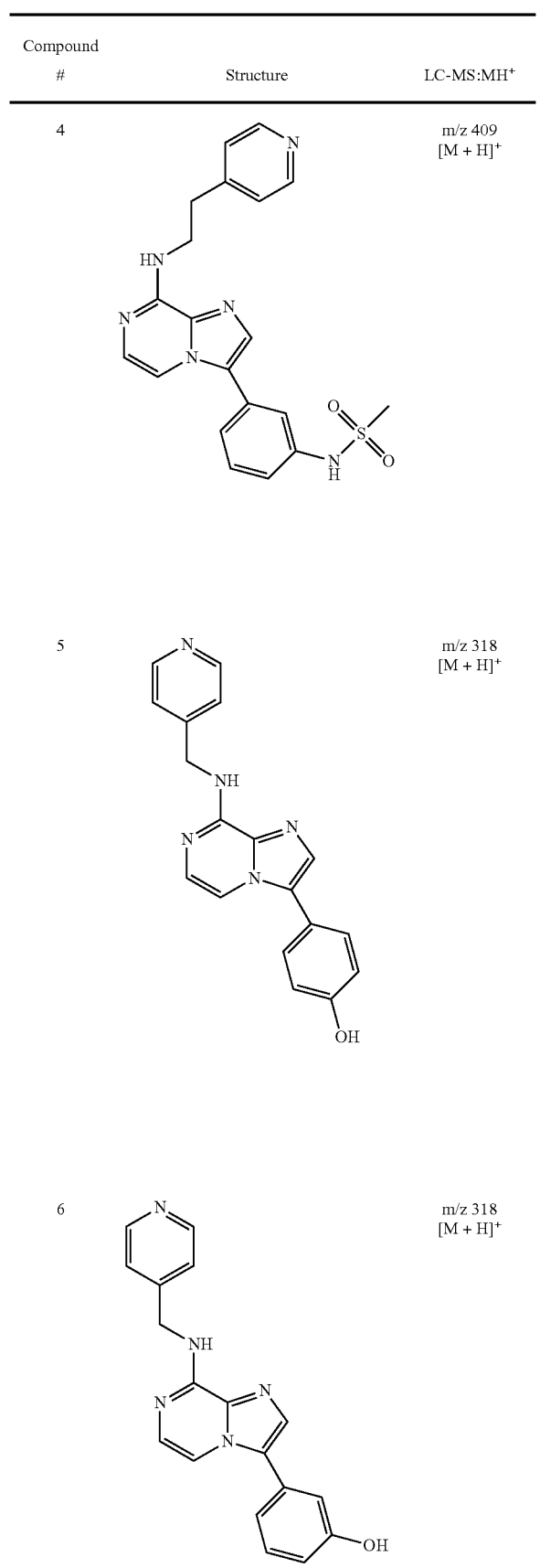 | m/z 409 [M + H]+ |
| 5 | 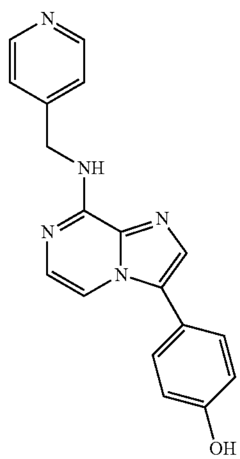 [SMILES: Oc1ccc(-c2cnc3c(NCc4ccncc4)nccn23)cc1] | m/z 318 [M + H]+ |
| 6 | 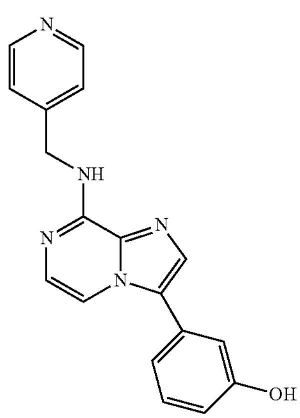 [SMILES: Oc1cccc(-c2cnc3c(NCc4ccncc4)nccn23)c1] | m/z 318 [M + H]+ |
| 7 | 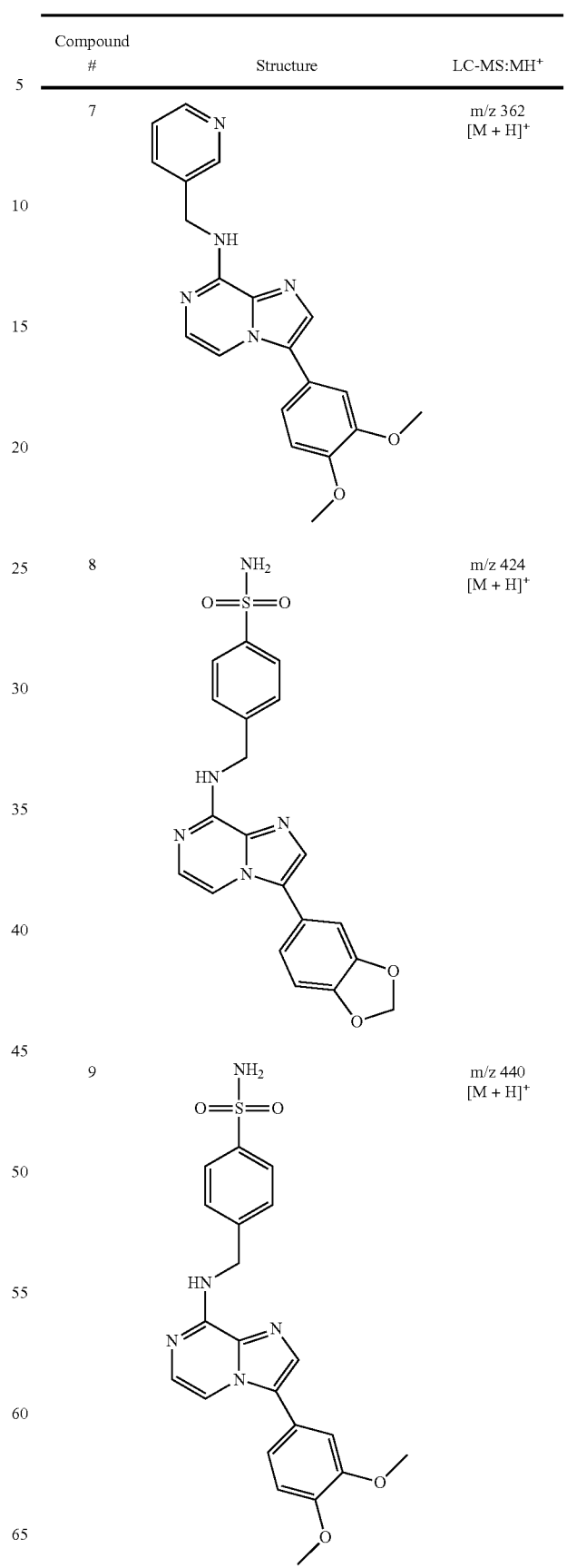 | m/z 362 [M + H]+ |
| 8 | | m/z 424 [M + H]+ |
| 9 | | m/z 440 [M + H]+ |

TABLE 1-continued

| Compound # | Structure | LC-MS:MH+ |
|---|---|---|
| 10 | 4-sulfamoylbenzyl-NH-imidazo[1,2-a]pyrazin-8-yl; 3-(3-chloro-4-fluorophenyl) substituent | m/z 432 [M + H]+ |
| 11 | 4-sulfamoylbenzyl-NH-imidazo[1,2-a]pyrazin-8-yl; 3-(4-fluorophenyl) substituent | m/z 398 [M + H]+ |
| 12 | 4-sulfamoylbenzyl-NH-imidazo[1,2-a]pyrazin-8-yl; 3-(3-methoxyphenyl) substituent | m/z 410 [M + H]+ |
| 13 | 4-(methoxycarbonyl)benzyl-NH-imidazo[1,2-a]pyrazin-8-yl; 3-(3,4-dimethoxyphenyl) substituent | m/z 419 [M + H]+ |
| 14 | benzyl-NH-imidazo[1,2-a]pyrazin-8-yl; 3-(3,4-dimethoxyphenyl) substituent | m/z 361 [M + H]+ |
| 15 | 4-sulfamoylbenzyl-NH-imidazo[1,2-a]pyrazin-8-yl; 3-(4-trifluoromethoxyphenyl) substituent | m/z 464 [M + H]+ |

TABLE 1-continued

| Compound # | Structure | LC-MS:MH+ |
|---|---|---|
| 16 | (4-methoxyphenyl at position 3; 4-sulfamoylbenzyl-NH at position 8 of imidazo[1,2-a]pyrazine) | m/z 410 [M + H]+ |
| 17 | (3,4-dimethoxyphenyl at position 3; 4-sulfamoylphenethyl-NH at position 8 of imidazo[1,2-a]pyrazine) | m/z 454 [M + H]+ |
| 18 | (3-acetylphenyl at position 3; 4-sulfamoylbenzyl-NH at position 8 of imidazo[1,2-a]pyrazine) | m/z 422 [M + H]+ |
| 19 | (3,4-dimethoxyphenyl at position 3; 4-(methylsulfonyl)benzyl-NH at position 8 of imidazo[1,2-a]pyrazine) | m/z 439 [M + H]+ |
| 20 | (3-methoxy-4-hydroxyphenyl at position 3; 4-sulfamoylbenzyl-NH at position 8 of imidazo[1,2-a]pyrazine) | m/z 426 [M + H]+ |
| 21 | (4-(hydroxymethyl)phenyl at position 3; 4-sulfamoylbenzyl-NH at position 8 of imidazo[1,2-a]pyrazine) | m/z 422 [M + H]+ |

TABLE 1-continued
| Compound # | Structure | LC-MS:MH+ |
|---|---|---|
| 22 | 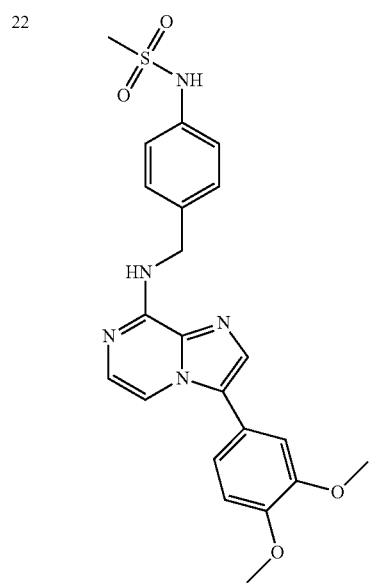 | m/z 454 [M + H]+ |
| 23 | 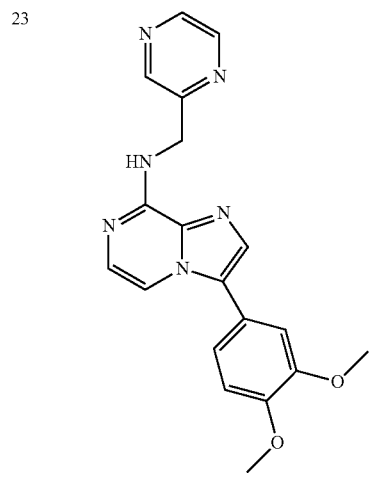 | m/z 363 [M + H]+ |
| 24 | 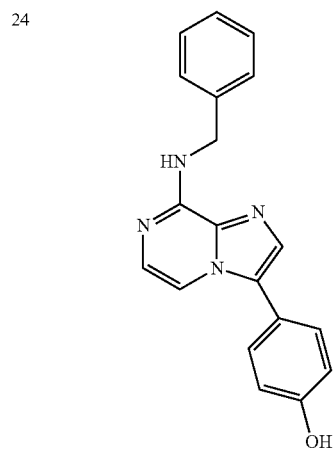 | m/z 317 [M + H]+ |
| 25 | 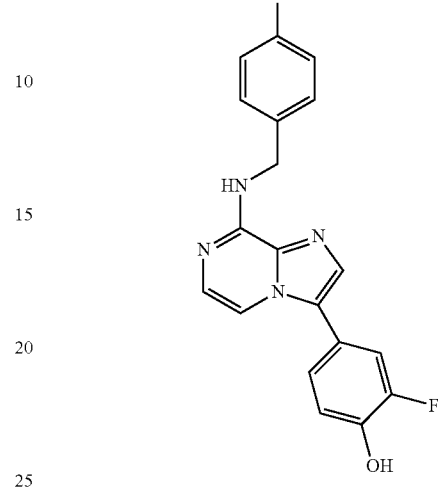 | m/z 414 [M + H]+ |
| 26 | 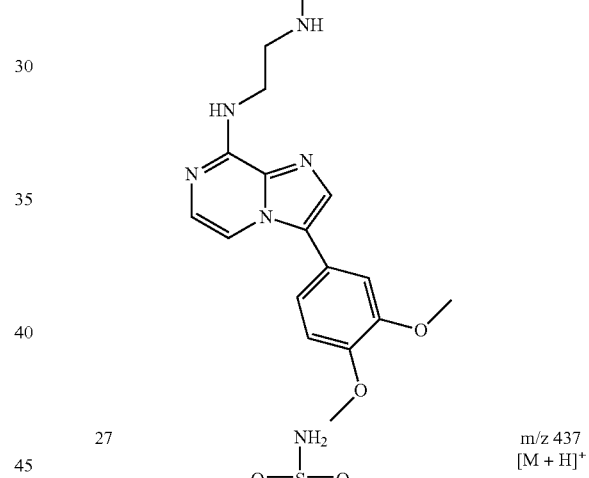 | m/z 356 [M + H]+ |
| 27 | 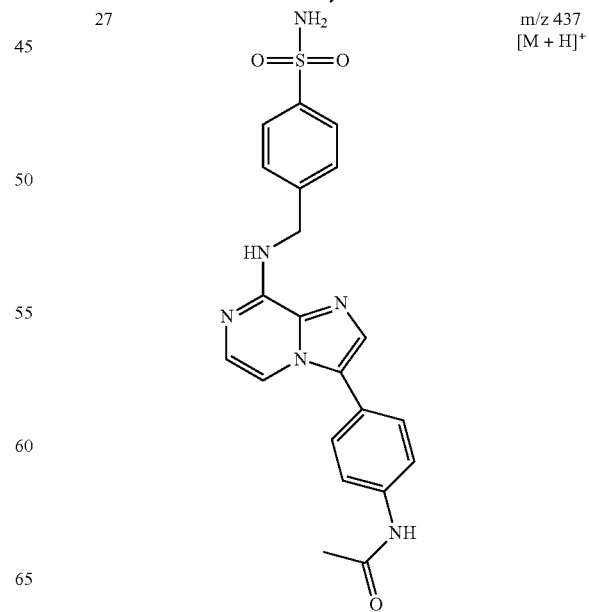 | m/z 437 [M + H]+ |

TABLE 1-continued

| Compound # | Structure | LC-MS:MH+ |
|---|---|---|
| 28 | 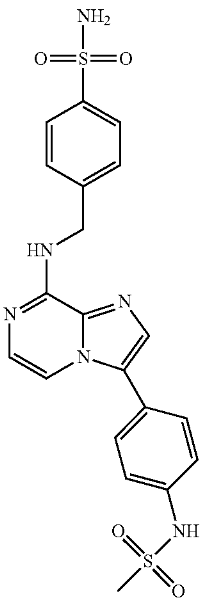 [SMILES: CS(=O)(=O)Nc1ccc(-c2cnc3c(NCc4ccc(S(N)(=O)=O)cc4)nccn23)cc1] | m/z 473 [M + H]+ |
| 29 | 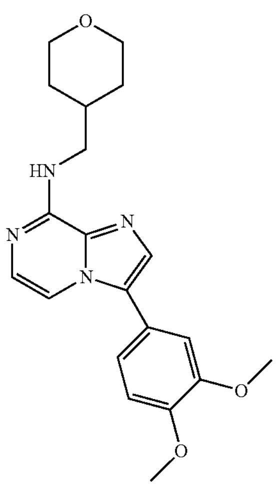 [SMILES: COc1ccc(-c2cnc3c(NCC4CCOCC4)nccn23)cc1OC] | m/z 369 [M + H]+ |
| 30 | 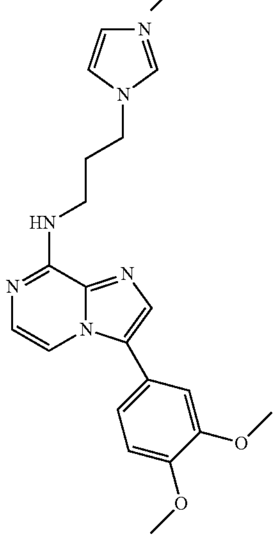 | m/z 379 [M + H]+ |

TABLE 1-continued

| Compound # | Structure | LC-MS:MH+ |
|---|---|---|
| 31 | 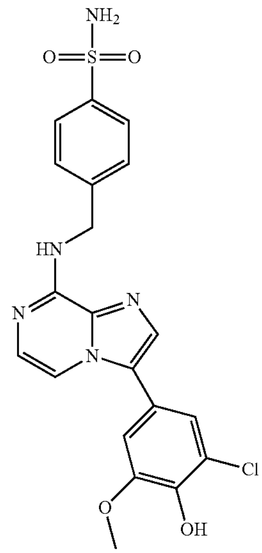 [SMILES: COc1cc(-c2cnc3c(NCc4ccc(S(N)(=O)=O)cc4)nccn23)cc(Cl)c1O] | m/z 460 [M + H]+ |
| 32 | 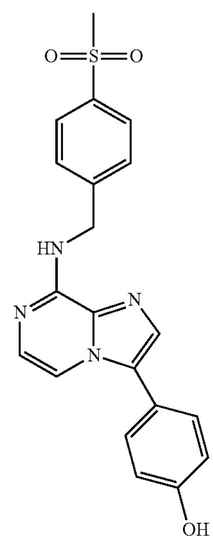 [SMILES: CS(=O)(=O)c1ccc(CNc2nccn3c(-c4ccc(O)cc4)cnc23)cc1] | m/z 395 [M + H]+ |
| 33 | 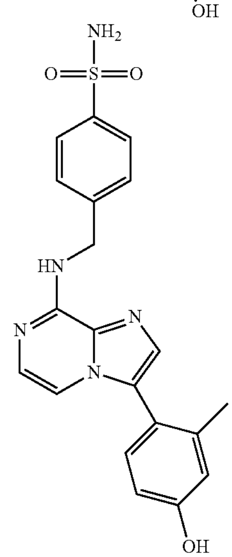 | m/z 410 [M + H]+ |

TABLE 1-continued
| Compound # | Structure | LC-MS:MH+ |
|---|---|---|
| 34 | 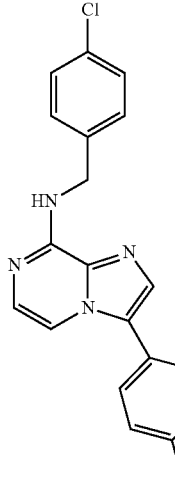 | m/z 351 [M + H]+ |
| 35 | 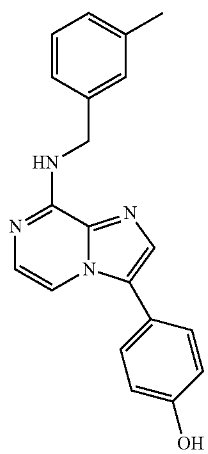 | m/z 331 [M + H]+ |
| 36 | 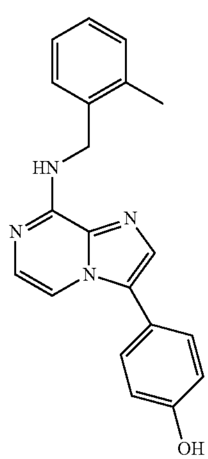 [SMILES: Cc1ccccc1CNc1nccn2c(-c3ccc(O)cc3)cnc12] | m/z 331 [M + H]+ |
| 37 | 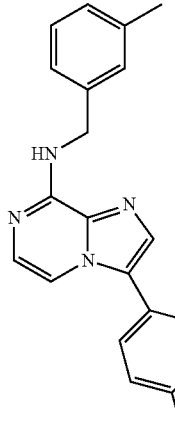 | m/z 351 [M + H]+ |
| 38 | | m/z 331 [M + H]+ |
| 39 | 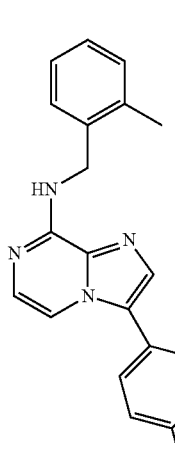 | m/z 384 [M + H]+ |

TABLE 1-continued
| Compound # | Structure | LC-MS:MH+ |
|---|---|---|
| 40 | 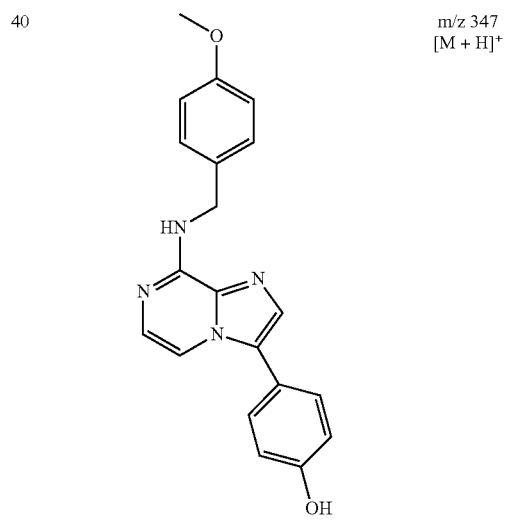 | m/z 347 [M + H]+ |
| 41 | 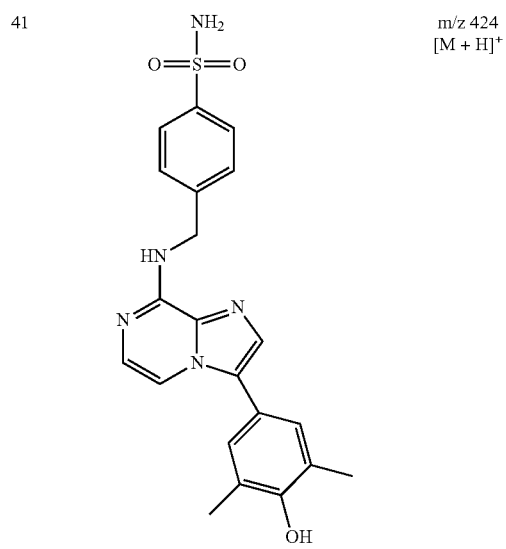 | m/z 424 [M + H]+ |
| 42 | 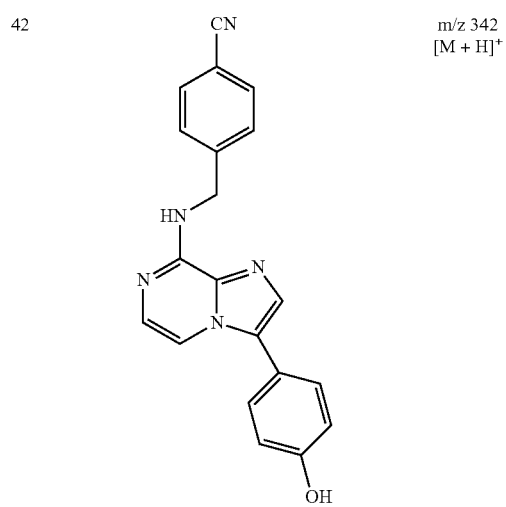 | m/z 342 [M + H]+ |
TABLE 1-continued
| Compound # | Structure | LC-MS:MH+ |
|---|---|---|
| 43 | 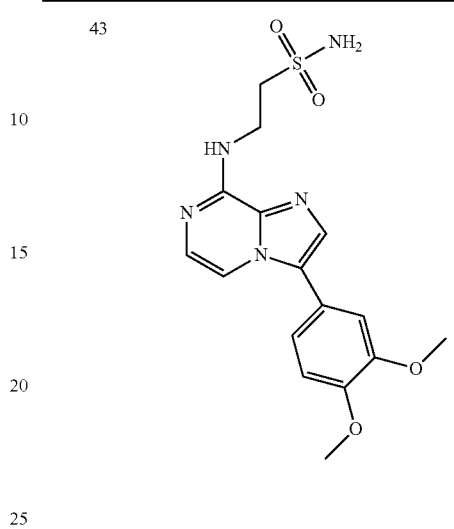 | m/z 378 [M + H]+ |
| 44 | 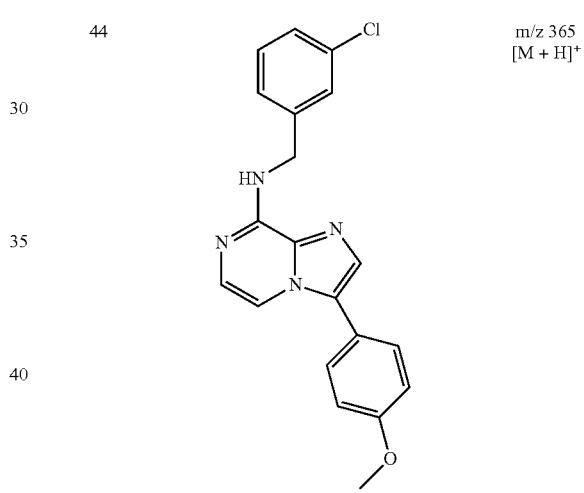 | m/z 365 [M + H]+ |
| 45 | 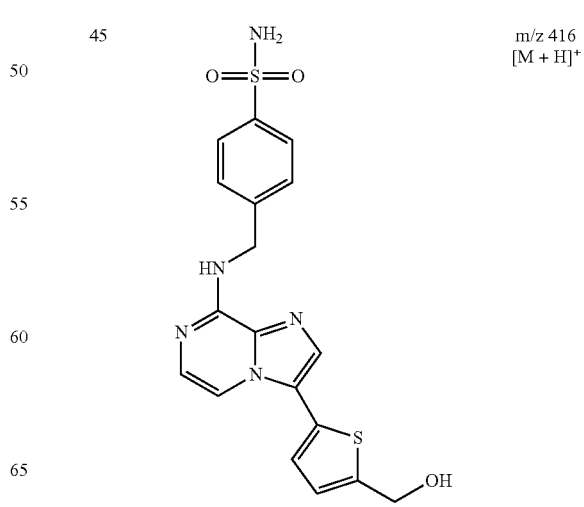 | m/z 416 [M + H]+ |

TABLE 1-continued
| Compound # | Structure | LC-MS:MH+ |
|---|---|---|
| 46 | 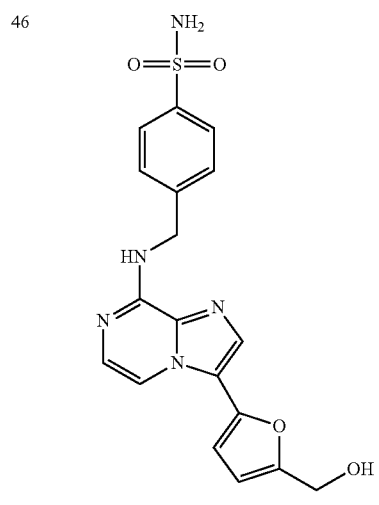 | m/z 400 [M + H]+ |
| 47 | 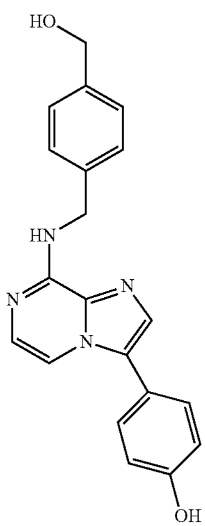 [SMILES: OCc1ccc(CNc2nccn3c(-c4ccc(O)cc4)cnc23)cc1] | m/z 347 [M + H]+ |
| 48 | 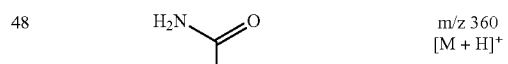 | m/z 360 [M + H]+ |
TABLE 1-continued
| Compound # | Structure | LC-MS:MH+ |
|---|---|---|
| 49 | 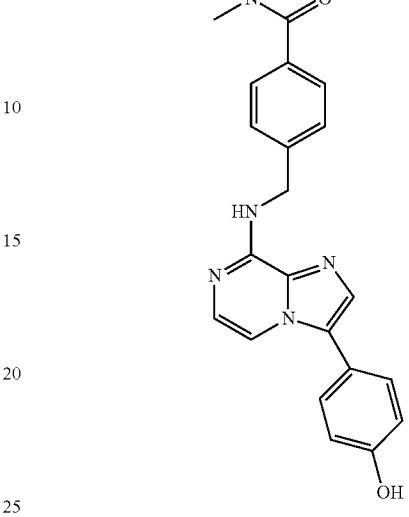 | m/z 374 [M + H]+ |
| 50 | 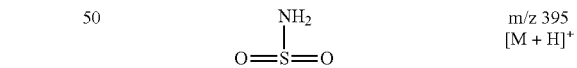 | m/z 395 [M + H]+ |
| 51 | 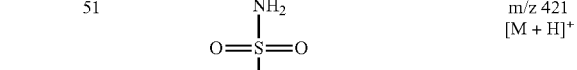 | m/z 421 [M + H]+ |

TABLE 1-continued

| Compound # | Structure | LC-MS:MH+ |
|---|---|---|
| 52 | (4-hydroxyphenyl)-imidazo[1,2-a]pyrazine with 4-(HOOC)benzyl-NH | m/z 361 [M + H]+ |
| 53 | (3-formyl-4-hydroxyphenyl)-imidazo[1,2-a]pyrazine with 4-sulfamoylbenzyl-NH | m/z 438 [M + H]+ |
| 54 | (3-nitro-4-hydroxyphenyl)-imidazo[1,2-a]pyrazine with 4-sulfamoylbenzyl-NH | m/z 441 [M + H]+ |
| 55 | (6-methoxynaphth-2-yl)-imidazo[1,2-a]pyrazine with 4-sulfamoylbenzyl-NH | m/z 460 [M + H]+ |
| 56 | (3-methoxy-4-hydroxyphenyl)-imidazo[1,2-a]pyrazine with 3-sulfamoylbenzyl-NH | m/z 426 [M + H]+ |
| 57 | (3-fluoro-4-hydroxyphenyl)-imidazo[1,2-a]pyrazine with 3-sulfamoylbenzyl-NH | m/z 414 [M + H]+ |

TABLE 1-continued
| Compound # | Structure | LC-MS:MH+ |
|---|---|---|
| 58 | 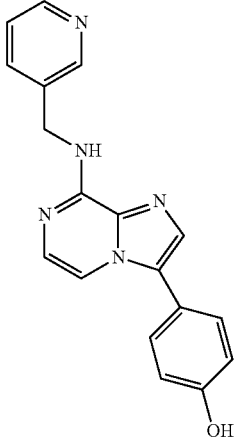 [SMILES: Oc1ccc(-c2cnc3c(NCc4cccnc4)nccn23)cc1] | m/z 318 [M + H]+ |
| 59 | 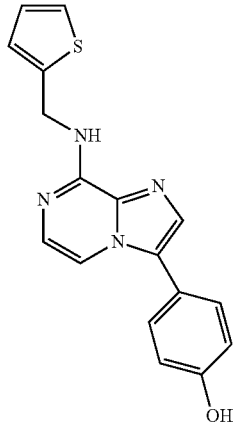 [SMILES: Oc1ccc(-c2cnc3c(NCc4cccs4)nccn23)cc1] | m/z 323 [M + H]+ |
| 60 | 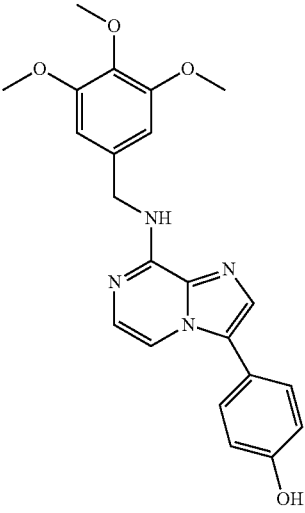 [SMILES: COc1cc(CNc2nccn3c(-c4ccc(O)cc4)cnc23)cc(OC)c1OC] | m/z 407 [M + H]+ |
| 61 | 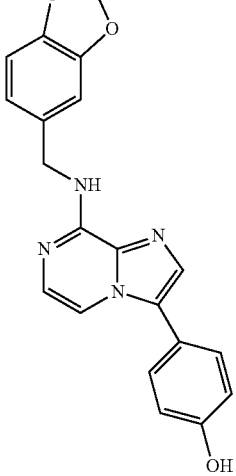 | m/z 361 [M + H]+ |
| 62 | 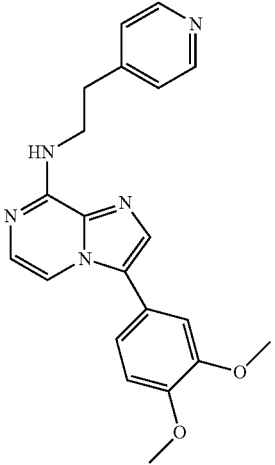 [SMILES: COc1ccc(-c2cnc3c(NCCc4ccncc4)nccn23)cc1OC] | m/z 376 [M + H]+ |
| 63 | 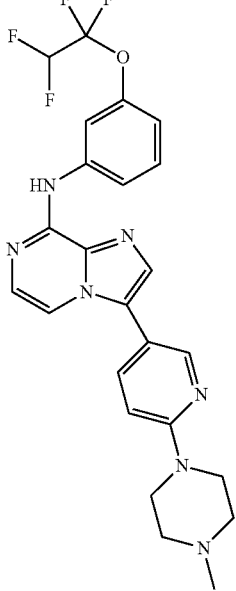 | m/z 502 [M + H]+ |

TABLE 1-continued
| Compound # | Structure | LC-MS:MH+ |
|---|---|---|
| 64 | 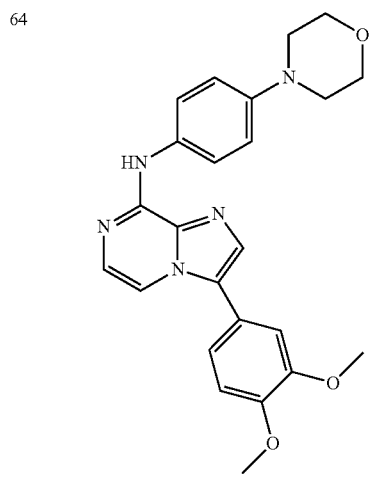 | m/z 432 [M + H]+ |
| 65 | 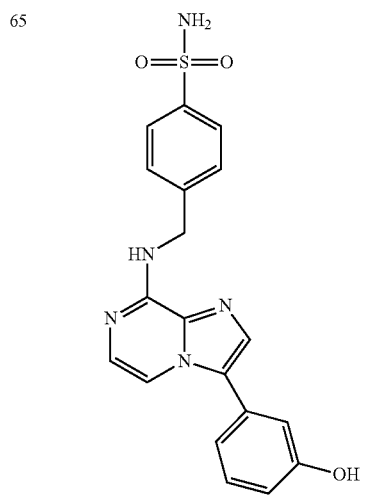 | m/z 396 [M + H]+ |
| 66 | 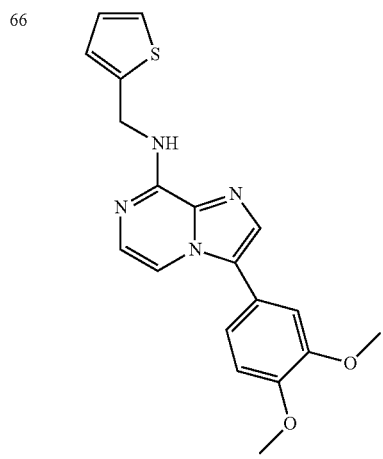 | m/z 367 [M + H]+ |
| 67 | 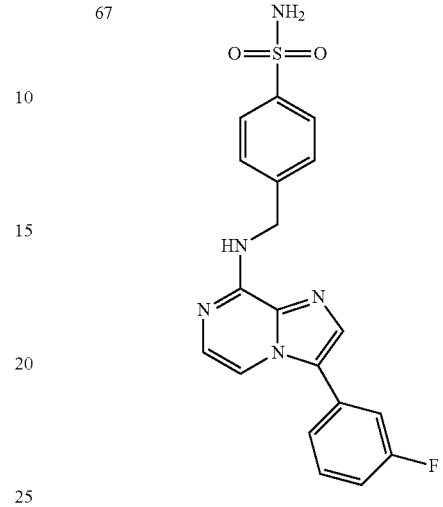 | m/z 398 [M + H]+ |
| 68 | 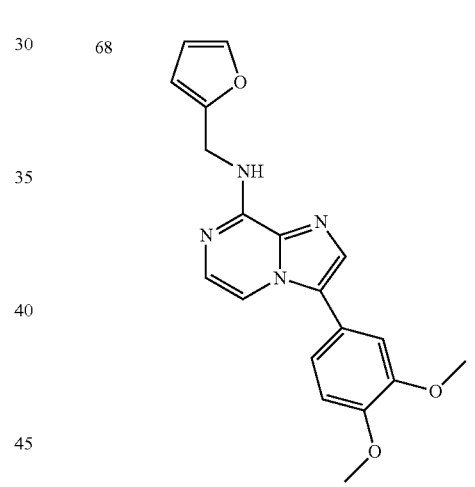 | m/z 351 [M + H]+ |
| 69 | 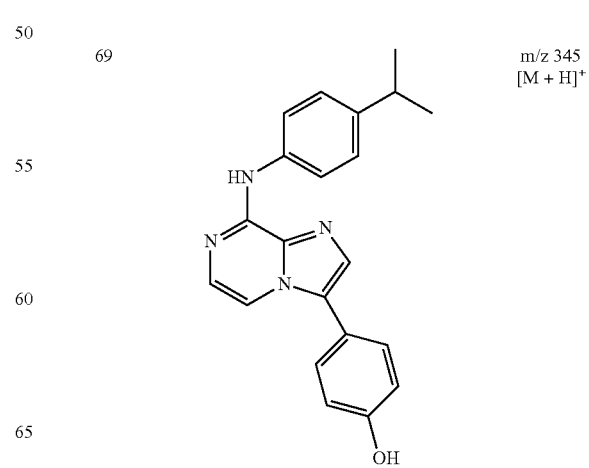 | m/z 345 [M + H]+ |

TABLE 1-continued
| Compound # | Structure | LC-MS:MH+ |
|---|---|---|
| 70 | 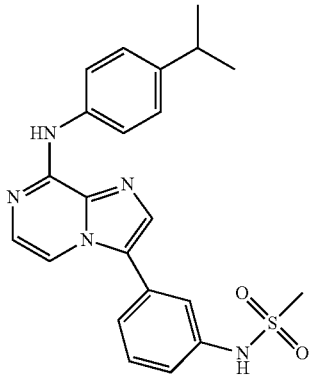 [SMILES: CC(C)c1ccc(Nc2nccn3c(-c4cccc(NS(C)(=O)=O)c4)cnc23)cc1] | m/z 422 [M + H]+ |
| 71 | 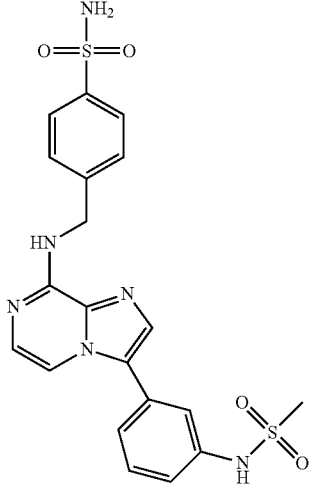 [SMILES: CS(=O)(=O)Nc1cccc(-c2cnc3c(NCc4ccc(S(N)(=O)=O)cc4)nccn23)c1] | m/z 473 [M + H]+ |
| 72 | 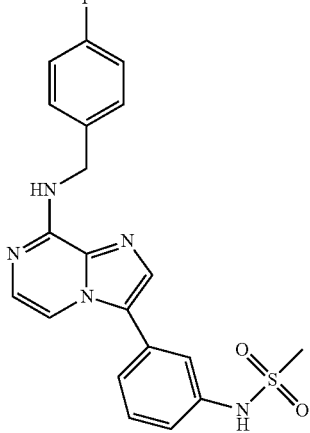 | m/z 424 [M + H]+ |
| 73 | 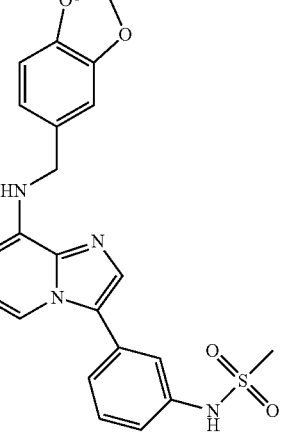 | m/z 438 [M + H]+ |
| 74 | 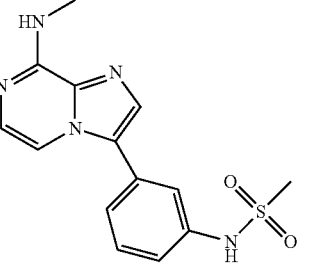 | m/z 380 [M + H]+ |
| 75 | 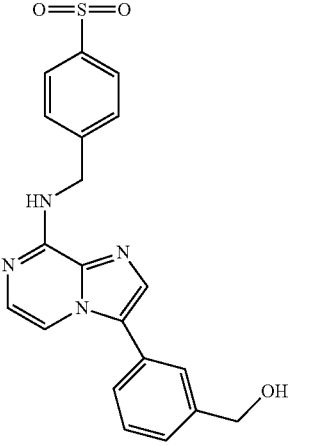 | m/z 410 [M + H]+ |

TABLE 1-continued
| Compound # | Structure | LC-MS:MH+ |
|---|---|---|
| 76 | 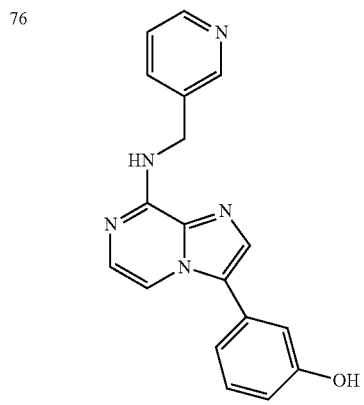 | m/z 316 [M − H]− |
| 77 | 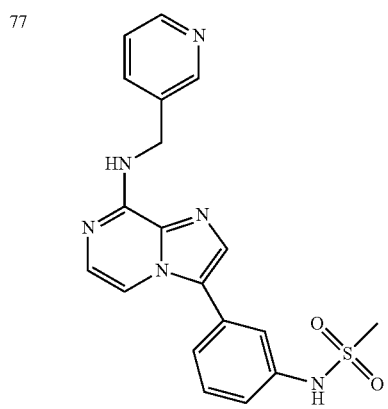 | m/z 393 [M − H]− |
| 78 | 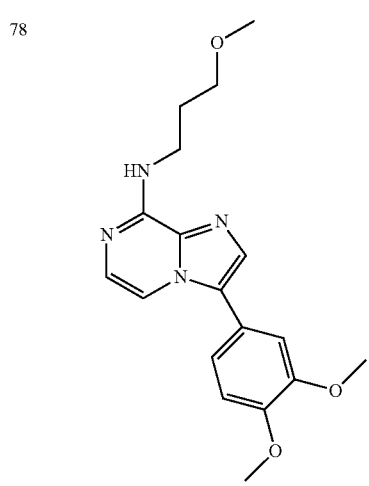 | m/z 343 [M + H]+ |
TABLE 1-continued
| Compound # | Structure | LC-MS:MH+ |
|---|---|---|
| 79 | 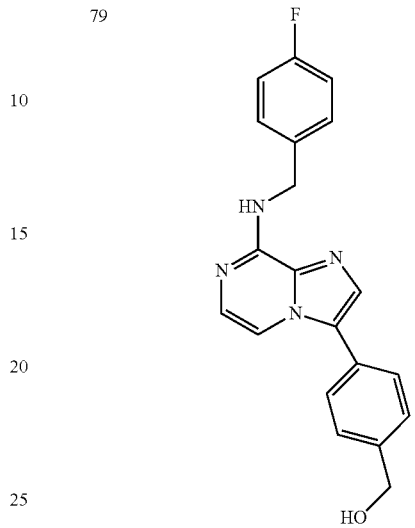 | m/z 349 [M + H]+ |
| 80 | 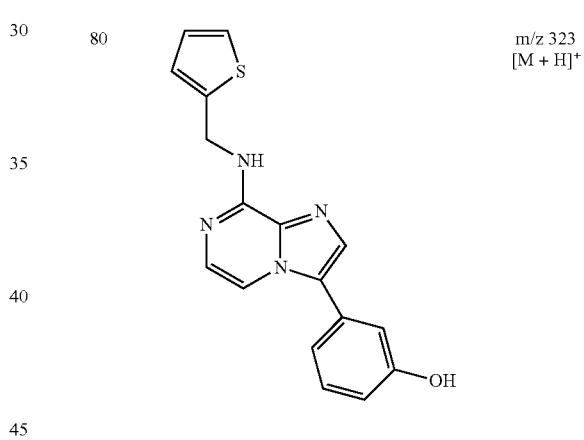 | m/z 323 [M + H]+ |
| 81 | 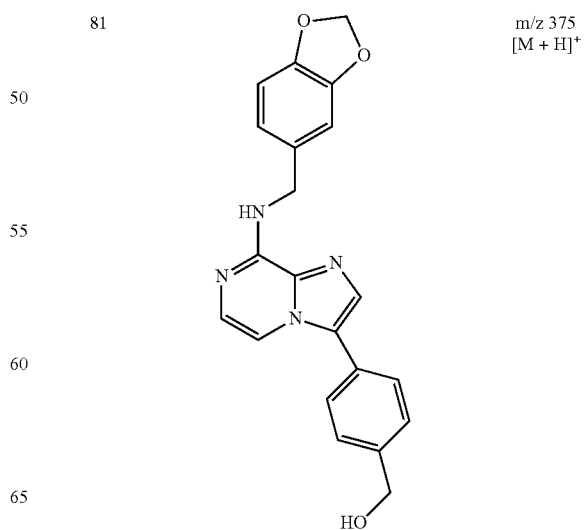 | m/z 375 [M + H]+ |

TABLE 1-continued

| Compound # | Structure | LC-MS:MH+ |
|---|---|---|
| 82 | 4-hydroxyphenyl-NH-imidazo[1,2-a]pyrazine-3-(3-fluorophenyl) | m/z 321 [M + H]+ |
| 83 | (4-methoxybenzyl)-NH-imidazo[1,2-a]pyrazine-3-(3-methanesulfonamidophenyl) | m/z 424 [M + H]+ |
| 84 | 2-(pyridin-3-yl)ethyl-NH-imidazo[1,2-a]pyrazine-3-(3-acetylphenyl) | m/z 358 [M + H]+ |
| 85 | 2-(pyridin-3-yl)ethyl-NH-imidazo[1,2-a]pyrazine-3-(3-hydroxyphenyl) | m/z 330 [M − H]− |
| 86 | (4-sulfamoylbenzyl)-NH-imidazo[1,2-a]pyrazine-3-(2-methoxyphenyl) | m/z 410 [M + H]+ |
| 87 | (4-sulfamoylbenzyl)-NH-imidazo[1,2-a]pyrazine-3-(3-acetamidophenyl) | m/z 437 [M + H]+ |

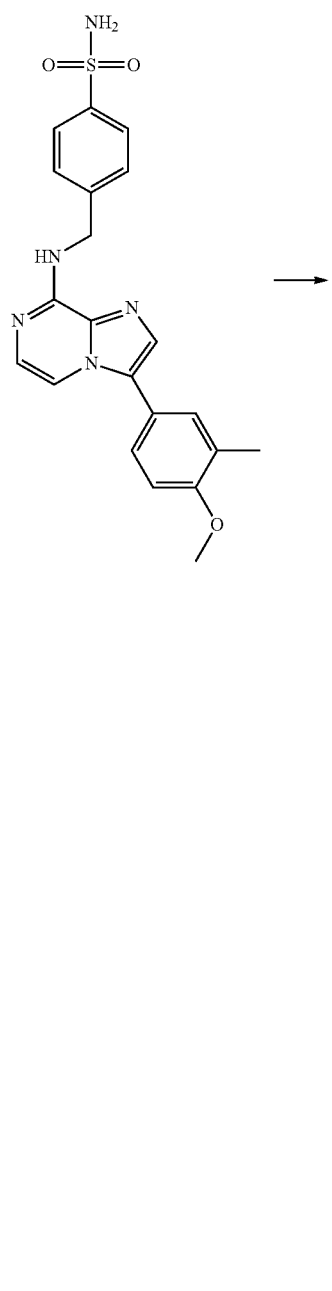

Compound 88: 4-{[3-(4-Hydroxy-3-methyl-phenyl)-imidazo[1,2-a]pyrazin-8-ylamino]-methyl}-benzenesulfonamide To a solution of 4-{[3-(4-Methoxy-3-methyl-phenyl)-imidazo[1,2-a]pyrazin-8-ylamino]-methyl}-benzenesulfonamide (0.167 g, 0.39 mmol) in dichloromethane (5 mL) at −78° C. was added boron tribromide (3.9 ml, 3.9 mmol, 1 M solution in dichloromethane). The reaction was allowed to warm gradually to ambient temperature then quenched with saturated aqueous sodium bicarbonate solution (30 mL). The reaction mixture was extracted with ethyl acetate (3×30 ml), the organic layers were combined and dried with magnesium sulphate, filtered and concentrated in vaccuo. The residue was taken up in DMSO and purified by prep HPLC. The product, 4-{[3-(4-Hydroxy-3-methyl-phenyl)-imidazo[1,2-a]pyrazin-8-ylamino]-methyl}-benzenesulfonamide, is obtained as a white solid (25 mg, 16%) (LC-MS m/z 410 [M+H]$^+$).

Compounds 89 and 90 were prepared in a similar fashion.

TABLE 2

| Compound # | Structure | LCMS: MH$^+$ |
|---|---|---|
| 88 | 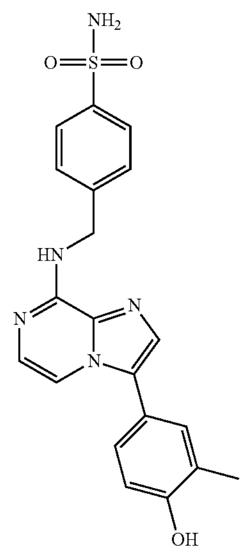 [SMILES: Cc1cc(-c2cnc3c(NCc4ccc(S(N)(=O)=O)cc4)nccn23)ccc1O] | m/z 410 [M + H]$^+$ |
| 89 | 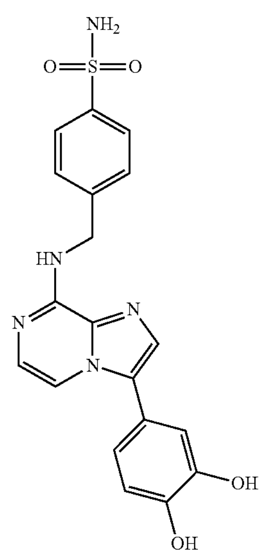 [SMILES: NS(=O)(=O)c1ccc(CNc2nccn3c(-c4ccc(O)c(O)c4)cnc23)cc1] | m/z 412 [M + H]$^+$ |

TABLE 2-continued

| Compound # | Structure | LCMS: MH+ |
|---|---|---|
| 90 | 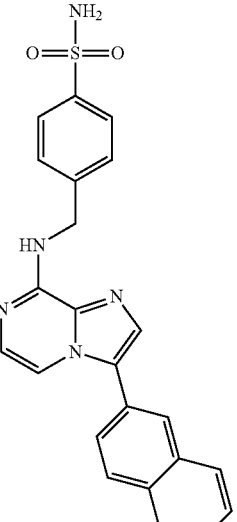 | m/z 460 [M + H]+ |

Compound 91

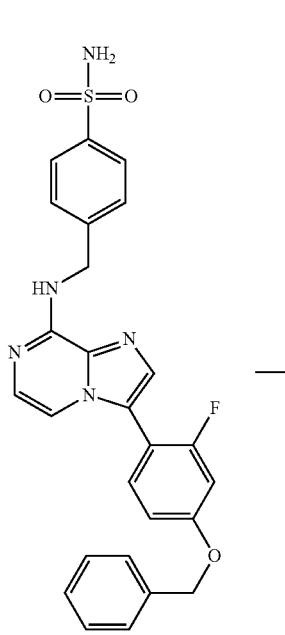

Compound 91: 4-{[3-(2-Fluoro-4-hydroxy-phenyl)-imidazo[1,2-a]pyrazin-8-ylamino]-methyl}-benzene-sulfonamide

To a solution of 4-{[3-(2-Fluoro-4-hydroxy-phenyl)-imidazo[1,2-a]pyrazin-8-ylamino]-methyl}-benzenesulfonamide (0.110 g, 0.218 mmol) and cyclohexadiene (0.41 ml, 4.36 mmol) in ethanol (3 ml) was added Palladium hydroxide on carbon (0.03 g, 0.043 mmol, 20 mol %). The reaction was heated to reflux for 2 hours then allowed to cool to ambient temperature. The reaction was filtered through celite and concentrated in vaccuo. The crude material was taken up in DMSO and purified by prep HPLC. The product, 4-{[3-(2-Fluoro-4-hydroxy-phenyl)-imidazo[1,2-a]pyrazin-8-ylamino]-methyl}-benzenesulfonamide, is obtained as a white solid (20 mg, 22%) (LC-MS m/z 414 [M+H]+).

TABLE 3

| Compound # | Structure | LCMS: MH+ |
|---|---|---|
| 91 | 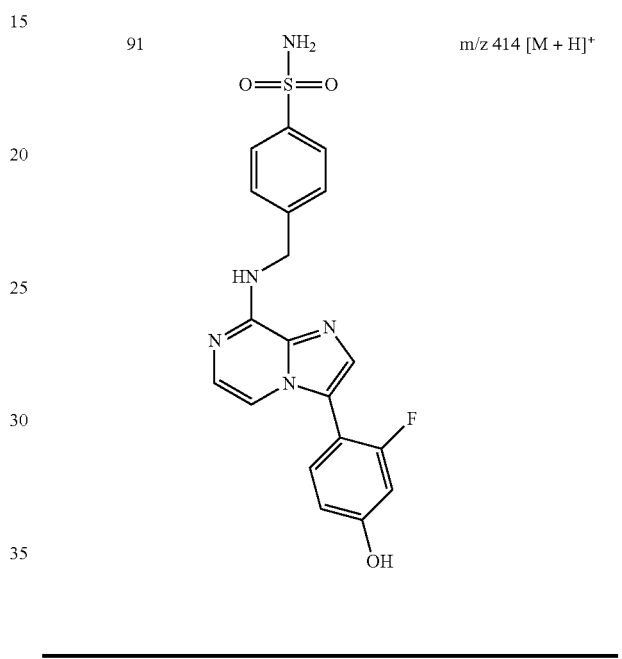 | m/z 414 [M + H]+ |

Compound 92

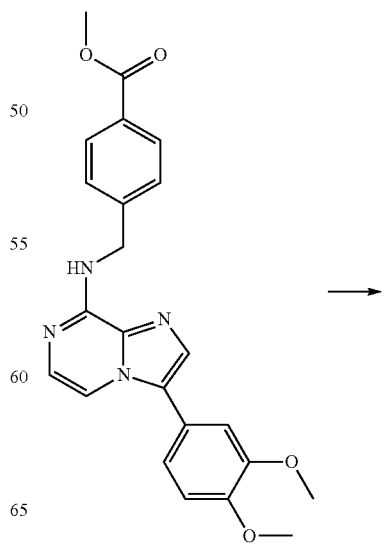

Compound 92: 4-{[3-(3,4-Dimethoxy-phenyl)-imidazo[1,2-a]pyrazin-8-ylamino]-methyl}-benzoic acid To a solution of 4-{[3-(3,4-Dimethoxy-phenyl)-imidazo[1,2-a]pyrazin-8-ylamino]-methyl}-benzoic acid methyl ester (0.20 g, 0.48 mmol) in tetrahydrofuran (4 ml) was added lithium hydroxide (0.72 ml, 0.72 mmol, 1 M aqueous solution). The reaction was stirred at ambient temperature for 24 hours then diluted with water (30 mL) and washed with ethyl acetate (30 ml). The aqueous phase was acidified with 1 M aqueous HCl and extracted with ethyl acetate (3×30 ml), the organic layers were combined and dried with magnesium sulphate, filtered and concentrated in vaccuo. The product, 4-{[3-(3,4-Dimethoxy-phenyl)-imidazo[1,2-a]pyrazin-8-ylamino]-methyl}-benzoic acid, is obtained as an off white solid (50 mg, 26%) (LC-MS m/z 405 [M+H]$^+$).

TABLE 4

| Compound # | Structure | LCMS: MH$^+$ |
|---|---|---|
| 92 | 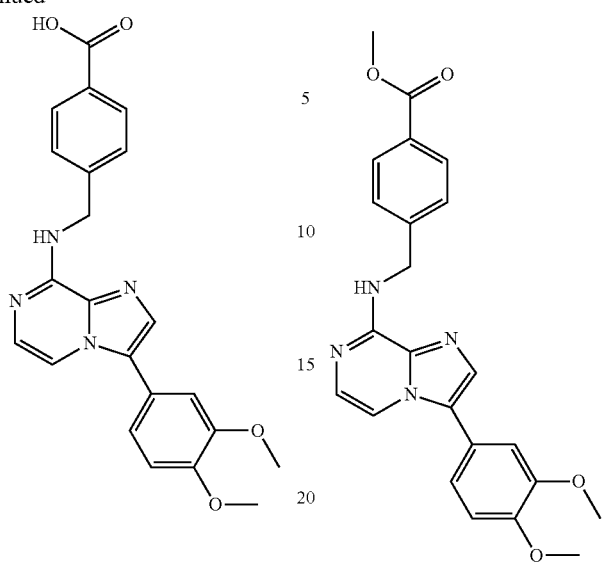 | m/z 405 [M + H]$^+$ |

Compound 93

(4-{[3-(3,4-Dimethoxy-phenyl)-imidazol[1,2-a]pyrazin-8-ylamino]-methyl}-phenyl)-methanol Diisobutylaluminium hydride (1 ml, 1.0 mmol, 1 M solution in dichloromethane) was added dropwise to a solution of 4-{[3-(3,4-dimethoxy-phenyl)-imidazo[1,2-a]pyrazin-8-ylamino]-methyl}-benzoic acid methyl ester (0.10 g, 0.24 mmol) in dichloromethane (1 mL) at ambient temperature. The reaction mixture was stirred for 1 hour then diluted with dichloromethane (50 ml) and washed with 1 M aqueous potassium sodium tartarate solution (30 mL) and water (30 mL). The organic layer was dried with magnesium sulphate, filtered and concentrated in vaccuo. The crude material was purified by column chromatography using 1:1 dichloromethane:ethyl acetate as eluent. The product, (4-{[3-(3,4-Dimethoxy-phenyl)-imidazo[1,2-a]pyrazin-8-ylamino]-methyl}-phenyl)-methanol, is obtained as a white solid (35 mg, 37%) (LC-MS m/z 391 [M+H]$^+$).

TABLE 5

| Compound # | Structure | LCMS: MH+ |
|---|---|---|
| 93 | (structure shown) | m/z 391 [M + H]+ |
| Compound 94 | (structure shown) | |

Compound 94: 2-Hydroxy-5-[8-(4-sulfamoyl-benzylamino)-imidazo[1,2-a]pyrazin-3-yl]-benzamide Trifluoroacetic acid (1.5 ml) and conc. Sulphuric acid (1.5 ml) were added to 4-{[3-(3-cyano-4-hydroxy-phenyl)-imidazo[1,2-a]pyrazin-8-ylamino]-methyl}-benzenesulfonamide (0.093 g, 0.2 mmol) and the resulting solution was stirred at ambient temperature for 24 hours. The reaction mixture was neutralized with conc. Aqueous sodium carbonate solution and extracted with ethyl acetate (2×50 mL). The organic layers were combined and dried with magnesium sulphate, filtered and concentrated in vaccuo. The crude material was taken up in DMSO and purified by prep HPLC. The product, 2-hydroxy-5-[8-(4-sulfamoyl-benzylamino)-imidazo[1,2-a]pyrazin-3-yl]-benzamide, is obtained as a white solid (4.2 mg, 5%) (LC-MS m/z 439 [M+H]+).

TABLE 6

| Compound # | Structure | LCMS: MH+ |
|---|---|---|
| 94 | (structure shown) | m/z 439 [M + H]+ |

General Method 2

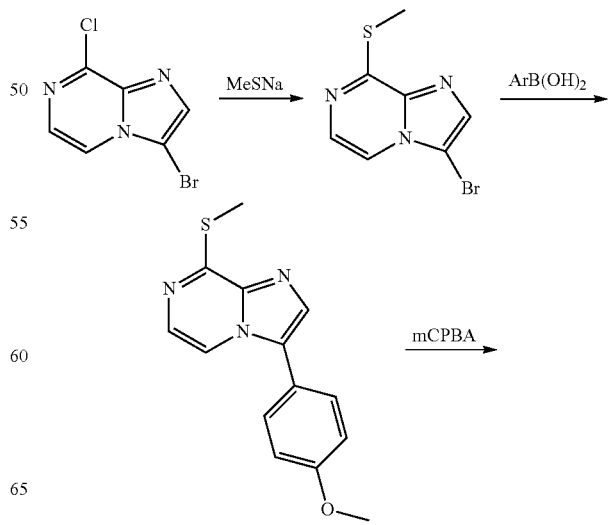

113

-continued

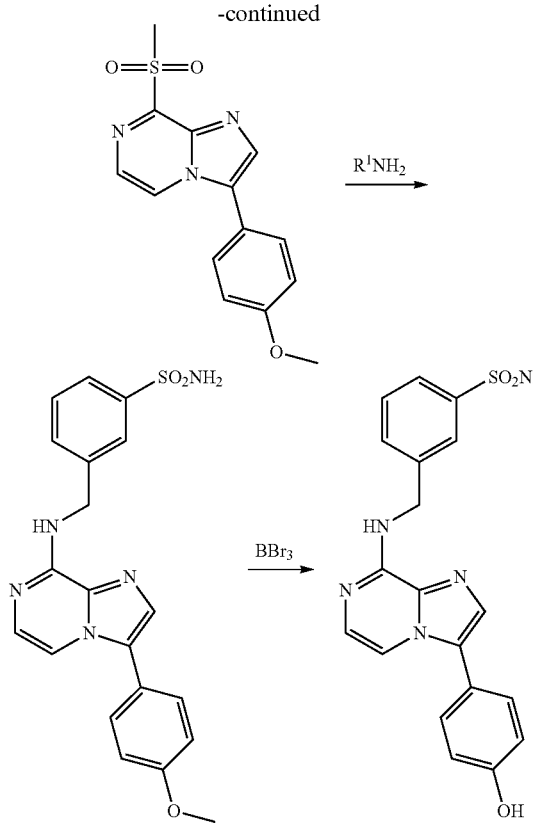

3-Bromo-8-methylsulfanyl-imidazo[1,2-a]pyrazine

To a solution of 3-bromo-8-chloro-imidazo[1,2-a]pyrazine (4.0 g, 18.2 mmol) in DMF (16 mL) MeSNa (1.52 g, 21.8 mmol) is added and stirred at 70° C. for 2 h. After this time the solution is allowed to cool, poured into 16 mL of water, stirred for 30 minutes and the solid obtained filtered off and washed with water (3×50 mL). The product, 3-Bromo-8-methylsulfanyl-imidazo[1,2-a]pyrazine was obtained as a beige solid (3.21 g, 72.3%).

3-(4-Methoxy-phenyl)-8-methylsulfanyl-imidazo[1,2-a]pyrazine

A mixture of 3-Bromo-8-methylsulfanyl-imidazo[1,2-a]pyrazine (1.06 g, 4.33 mmol), 4-methoxybenzeneboronic acid (0.79 g, 5.2 mmol), Pd(OAc)$_2$ (0.05 g, 0.22 mmol), (oxidi-2,1-phenylene)bis(diphenylphosphine) (233 mg, 0.43 mmol), 1.5M K$_2$CO$_3$ in water (5.8 mL, 8.66 mmol) and DMF (12.8 mL) is stirred at 88° C. for 16 h. Then allowed to cool, filtered through cotton, diluted with EtOAc and washed with water and brine. The organic layer is dried with MgSO$_4$ anh., filtered and evaporated. The crude is purified by column chromatography using a gradient of (Pet. Ether 40-60/AcOEt: 7/3 to 1/1) to give 3-(4-Methoxy-phenyl)-8-methylsulfanyl-imidazo[1,2-a]pyrazine as a pale yellow solid (1.0 g, 85%).

8-Methanesulfonyl-3-(4-methoxy-phenyl)-imidazo[1,2-a]pyrazine

Over a solution of 3-(4-Methoxy-phenyl)-8-methylsulfanyl-imidazo[1,2-a]pyrazine (1.00 g, 3.69 mmol) in DCM (30 mL) mCPBA (1.60 g, 9.22 mmol) is added and stirred at room temperature for 3 h. Then the reaction mixture is diluted with DCM, washed with NaHCO$_3$ sat. and brine. The organic layer is dried with MgSO$_4$ anh., filtered and evaporated to yield an orange viscous oil that is triturated with AcOEt. The solid formed is filtered off and washed with AcOEt to give 8-Methanesulfonyl-3-(4-methoxy-phenyl)-imidazo[1,2-a]pyrazine as a yellow solid (765 mg, 68%).

3-{[3-(4-Methoxy-phenyl)-imidazo[1,2-a]pyrazin-8-ylamino]-methyl}-benzenesulfonamide A mixture of 8-Methanesulfonyl-3-(4-methoxy-phenyl)-imidazo[1,2-a]pyrazine (0.150 g, 0.495 mmol), 3-Aminomethyl-benzenesulfonamide TFA salt (0.223 g, 0.742 mmol), DIPEA (0.260 mL, 1.50 mmol) in NMP (0.66 mL) is stirred at 100° C. for 16 hours. The reaction mixture is diluted with AcOEt, washed with water and brine, dried with MgSO$_4$ anh., filtered and evaporated. The crude is purified by column chromatography using a gradient of (Pet.Ether 40-60/AcOEt: 1/1 to 0/1) to give 3-{[3-(4-Methoxy-phenyl)-imidazo[1,2-a]pyrazin-8-ylamino]-methyl}-benzenesulfonamide as a pale yellow solid (0.135 g, 67%). LC-MS m/z 410 [M+H]$^+$.

Compound 95: 3-{[3-(4-Hydroxy-phenyl)-imidazol[1,2-a]pyrazin-8-ylamino]-methyl}-benzenesulfonamide BBr$_3$ (2.81 mL, 1.0M in DCM, 2.81 mmol) is added to a suspension of 3-{[3-(4-Methoxy-phenyl)-imidazo[1,2-a]pyrazin-8-ylamino]-methyl}-benzenesulfonamide (0.115 g, 0.281 mmol) in DCM (3 mL) at −78° C. under nitrogen atmosphere. The reaction is allowed to warm to r.t and monitored by analytical HPLC. After 2 h the reaction is complete and is cooled to −78° C., quenched with a solution of saturated aqueous K$_2$CO$_3$. The reaction is diluted with AcOEt, washed with water, dried with MgSO$_4$ anh., filtered and evaporated to give 0.058 g of 3-{[3-(4-Hydroxy-phenyl)-imidazo[1,2-a]pyrazin-8-ylamino]-methyl}-benzenesulfonamide as a brown oil (52%). No further purification was required. LC-MS m/z 396 [M+H]$^+$.

Compounds 96-103

By essentially the same procedures as described for General Method 2 and Compound 95 above, the compounds in Table 7 can be prepared.

TABLE 7

| Compound # | Structure | LCMS: MH$^+$ |
|---|---|---|
| 96 | 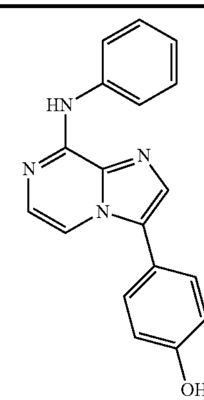 | m/z 303 [M + H]$^+$ |

TABLE 7-continued
| Compound # | Structure | LCMS: MH+ |
|---|---|---|
| 97 | 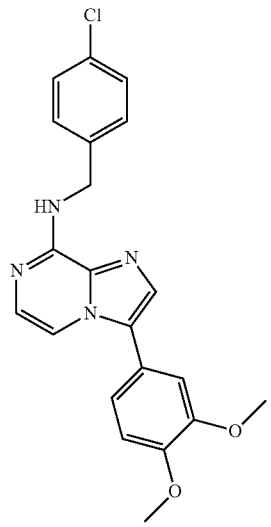 [SMILES: COc1ccc(-c2cnc3c(NCc4ccc(Cl)cc4)nccn23)cc1OC] | m/z 395 [M + H]+ |
| 98 | 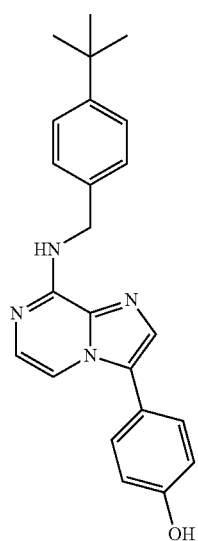 | m/z 373 [M + H]+ |
| 99 | 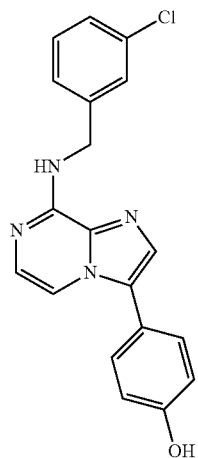 [SMILES: Oc1ccc(-c2cnc3c(NCc4cccc(Cl)c4)nccn23)cc1] | m/z 351 [M + H]+ |
| 100 | 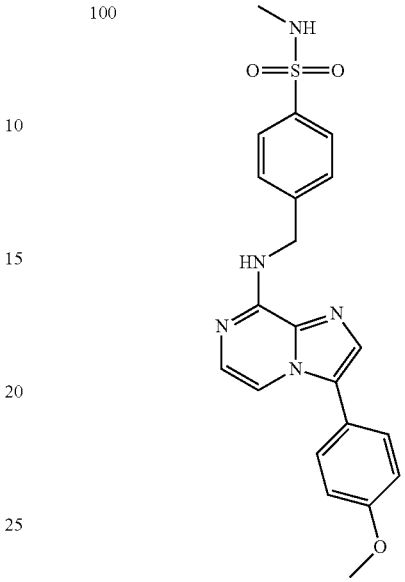 | m/z 424 [M + H]+ |
| 101 | 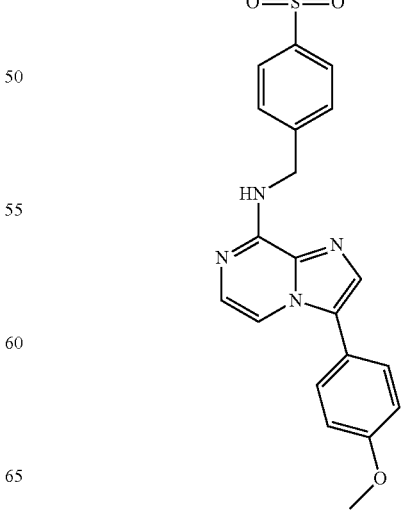 | m/z 438 [M + H]+ |

TABLE 7-continued
| Compound # | Structure | LCMS: MH+ |
|---|---|---|
| 102 | 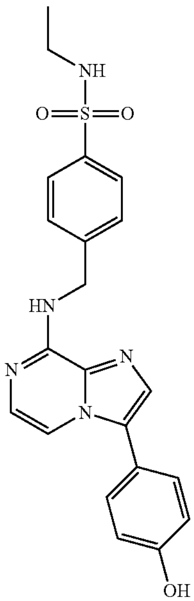 [SMILES: CCNS(=O)(=O)c1ccc(CNc2nccn3c(-c4ccc(O)cc4)cnc23)cc1] | m/z 424 [M + H]+ |
| 103 | 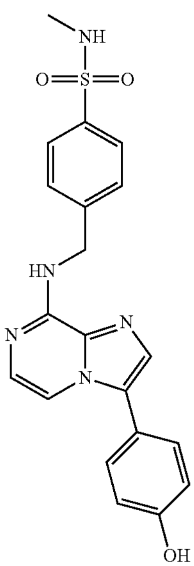 [SMILES: CNS(=O)(=O)c1ccc(CNc2nccn3c(-c4ccc(O)cc4)cnc23)cc1] | m/z 410 [M + H]+ |
General Method 3
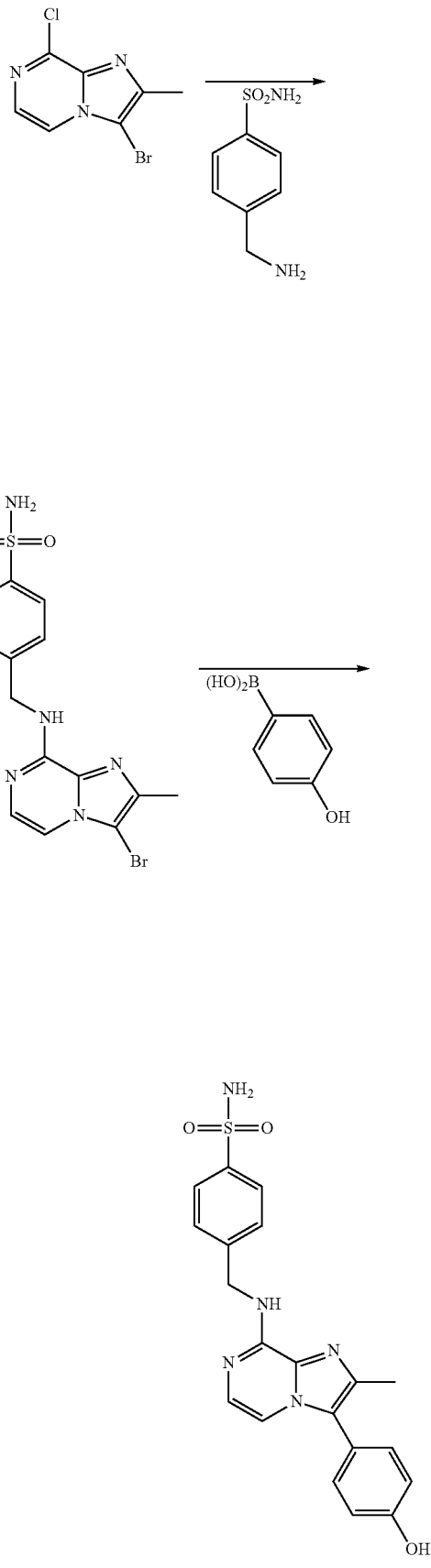

8-Chloro-2-methyl-imidazo[1,2-a]pyrazine

A solution of 2-amino-3-chloropyrazine (10 g, 77.5 mmol), chloroacetone (30 mL, 387 mmol) in MeOH (25 mL) is refluxed overnight at 88° C. It is then stirred for 1 h at 0° C. and any solid that forms, is filtered off and washed twice with MeOH (5 mL). The mother liq. are evaporated, diluted with EtOAc, and washed with HCl 2N, water and brine. The water and HCl mother liq. are evaporated to give a yellow solid that is neutralized with a saturated solution of $K_2CO_3$ in water, extracted with DCM, dried with $MgSO_4$ anh. filtered and concentrated. The crude material is purified by column chromatography using a gradient of (DCM/MeOH: 1/0 to 99/1) to give 8-Chloro-2-methyl-imidazo[1,2-a]pyrazine as an orange solid (1.02 g, 7.7%).

3-Bromo-8-chloro-2-methyl-imidazo[1,2-a]pyrazine

To a solution of 8-Chloro-2-methyl-imidazo[1,2-a]pyrazine (0.7 g, 4.18 mmol) in DCM (20 ml) is added N-bromo-succinimide (0.74 g, 4.18 mmol) and the reaction stirred at room temperature for 2 h. After this time the solution is washed with saturated aqueous solution of $Na_2CO_3$ (2×20 ml), dried ($MgSO_4$), filtered and concentrated in vacuo to give 3-bromo-8-chloro-2-methyl-imidazo[1,2-a]pyrazine (0.771 g, 75%).

4-[(3-Bromo-2-methyl-imidazo[1,2-a]pyrazin-8-ylamino)-methyl]-benzenesulphonamide To a solution of 3-bromo-8-chloro-2-methyl-imidazo[1,2-a]pyrazine (0.77 g, 3.12 mmol) in $^t$BuOH (10 ml) is added 4-aminomethyl-benzenesulfonamide hydrochloride (1.04 g, 4.69 mmol) and DIPEA (1.63 ml, 9.36 mmol). The reaction is heated to 108° C. and stirred for 16 h. After this time the solution is allowed to cool, resulting in a thick white precipitate. The precipitate is filtered and washed with diethyl ether to give 4-[(3-Bromo-2-methyl-imidazo[1,2-a]pyrazin-8-ylamino)-methyl]-benzenesulphonamide as a white solid (0.37 g, 30%)

Compound 104: 4-{[3-(4-Hydroxy-phenyl)-2-methyl-imidazo[1,2-a]pyrazin-8-ylamino]-methyl}-benzenesulfonamide To a 5 mL microwave tube is added 4-[(3-Bromo-2-methyl-imidazo[1,2-a]pyrazin-8-ylamino)-methyl]-benzene-sulfonamide (0.15 g, 0.379 mmol), 4-(4,4,5,5-tetramethyl-[1,3,2]dioxaborolan-2-yl)-phenol (0.084 g, 0.417 mmol), $Na_2CO_3$ (0.1 g, 0.95 mmol), Pd(OAc)$_2$ (approx. 7 mg, 0.028 mmol), and (oxidi-2,1-phenylene)bis(diphenylphosphine) (20 mg, 0.038 mmol). The mixture is suspended in DMF (3 mL) and water (1 mL) and the vessel is sealed under a nitrogen atmosphere. The reaction vessel is heated to 130° C. in the CEM microwave for 20 min then allowed to cool and filtered through Celite and washed with EtOAc. The filtrate is evaporated and the residue is taken up in DMSO and purified by prep HPLC. The product, 4-{[3-(4-Hydroxy-phenyl)-imidazo[1,2-a]pyrazin-8-ylamino]-methyl}-benzenesulfonamide, is obtained as a white solid (15 mg, 10%) LC-MS m/z 410 [M+H]$^+$.

Examples 105-107

By essentially the same procedures as described above for General Method 3 and Example 104, the compounds in Table 8 may be prepared.

TABLE 8

| Compound # | Structure | LCMS: MH$^+$ |
|---|---|---|
| 105 | (structure) | m/z 440 [M + H]$^+$ |
| 106 | (structure) | m/z 428 [M + H]$^+$ |
| 107 | (structure) | m/z 455 [M + H]$^+$ |

General Method 4

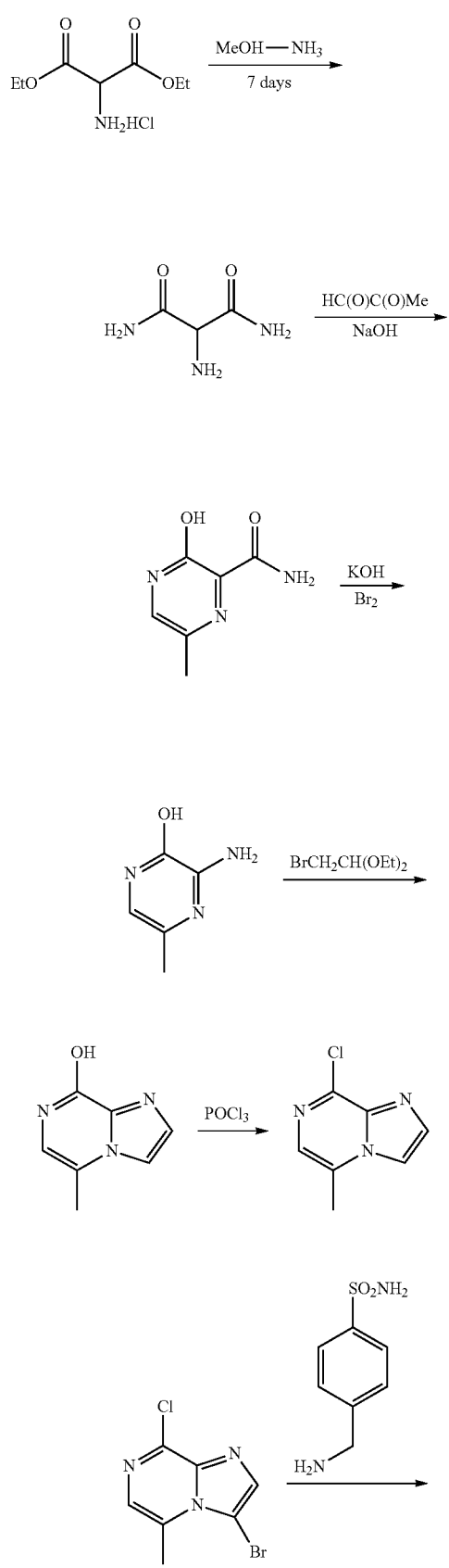

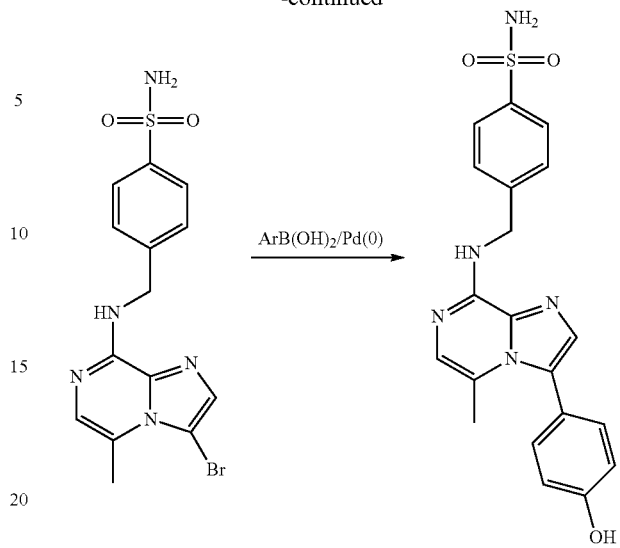

2-Amino-malonamide

A solution of diethyl aminomalonate hydrochloride (50.0 g, 0.237mol) in methanolic ammonia (750 mL, 7N, 5.25mol) is stirred at r.t. for 7 days in a sealed flask. Filtration and washing of the solid with MeOH will provide 2-amino-malonamide as a pale yellow product (25 g, 69%).

3-Hydroxy-6-methyl-pyrazine-2-carboxylic acid amide

An aqueous solution of NaOH (10.6 mL, 12.5N, 0.133mol) is added dropwise to a 40% water solution of pyruvic aldehyde (24 g, 9.6 g, 0.133mol) and 2-amino-malonamide (16 g, 0.136mol) at −20° C., keeping the temperature bellow 0° C. The reaction mixture is mechanically stirred overnight at r.t and then the reaction mixture is cooled to −20° C. and HCl conc. (16 mL, 0.16 mol) is slowly added keeping the temperature bellow 0° C. and stirred at r.t. for 48 h. The reaction mixture is cooled in an ice bath and the crystals formed filtered off, washed with a little water and dried with air, to give 3-hydroxy-6-methyl-pyrazine-2-carboxylic acid amide as a brown solid, (5.7 g, 28%).

3-Amino-5-methyl-pyrazin-2-ol

To a solution of KOH (6 g, 154 mmol) in water (46 mL) at 5° C. is added slowly bromine followed by 3-hydroxy-6-methyl-pyrazine-2-carboxylic acid amide (2.6 g, 17.0 mmol) with rapid stirring. The reaction mixture is warmed to 85° C. and stirred for 1 h 30 min. The reaction is cooled to 20° C. and acidified with HCl conc, basified with ammonium hydroxide conc. and left stand overnight at r.t. The solid obtained is filtered and washed with cold water, dried with air and then dried further in a vacuum oven at 60° C. to give 3-amino-5-methyl-pyrazin-2-ol as a beige solid (1.63 g, 76%).

5-Methyl-imidazo[1,2-a]pyrazin-8-ol

Bromoacetaldehyde diethyl acetal (12.2 mL, 81.4 mmol) and a solution of 48% HBr (0.94 mL) are heated at reflux for 1.5 hours, then poured into a suspension of NaHCO₃ (1.92 g) in propan-2-ol (31.3 mL). The resulting solid is filtered off and 3-amino-5-methyl-pyrazin-2-ol (3.13 g, 25.0 mmol) is added. The solution is refluxed for 2 hours then left to stand overnight and the solid formed washed with IPA and ether. The solid is added to a solution of DCM (60 mL) and NaHCO₃ sat. (30 mL), the two layers are separated and the aqueous phase is extracted with DCM. The combined organic layers are dried with MgSO₄ anh., filtered and evaporated to give a brown solid product. The aqueous phase is again extracted with a CHCl₃/IPA 9/1, dried with MgSO₄ anh., filtered and concentrated to give a brown solid product. The IPA and Ether used previously for washing the solid are combined, evaporated and submitted to the same process described previously to give a brown solid quite impurified from the DCM extraction and a brown solid with the CHCl₃/IPA of similar purity to the one obtained beforehand. The products resulting from the first DCM extraction and the two CHCl₃/IPA extraction are combined and washed with cold MeOH to give 5-Methyl-imidazo[1,2-a]pyrazin-8-ol as a pale yellow solid (1.32 g) that is submitted into the next step without further purification.

8-Chloro-5-methyl-imidazo[1,2-a]pyrazine

To a solution of 5-Methyl-imidazo[1,2-a]pyrazin-8-ol (1.32 g, 8.86 mmol) in POCl₃ (25 mL) is added pyridine (0.53 mL, 6.6 mmol) and the reaction stirred at 120° C. under N₂ atmosphere for 4 h 30 min. The reaction is cooled to 60° C. and poured into 80 g of ice and stirred for 1 h. The mixture is neutralized with NaOH (20%), extracted with CHCl₃/IPA 9/1, dried with MgSO₄ anh., filtered and concentrated to get a crude that is purified by column chromatography using a gradient of (DCM/MeOH:98/2 to 95/5) to give 8-Chloro-5-methyl-imidazo[1,2-a]pyrazine as a pale yellow solid (0.39 g, 26%).

3-Bromo-8-chloro-5-methyl-imidazo[1,2-a]pyrazine

N-bromosuccinimide (348 mg, 1.96 mmol) is added to a solution of 8-chloro-5-methyl-imidazo[1,2-a]pyrazine (327 mg, 1.98 mmol) in DCM (6 mL) and the reaction stirred at room temperature for 2 h. Once the reaction is finished the reaction mixture is diluted with DCM and washed twice with 4 mL of Na₂CO₃ sat., dried (MgSO₄), filtered and concentrated in vacuo to give a crude mixture that is purified by column chromatography using a gradient of (Pet.Ether40-60/AcOEt: 9/1 to 7/3) to give 3-Bromo-8-chloro-5-methyl-imidazo[1,2-a]pyrazine as a brown solid (335 mg, 69%).

4-[(3-Bromo-5-methyl-imidazo[1,2-a]pyrazin-8-ylamino)-methyl]-benzenesulfonamide To a solution of 3-bromo-8-chloro-5-methyl-imidazo[1,2-a]pyrazine (308 mg, 1.25 mmol) in ᵗBuOH (5 mL) is added 4-aminomethyl-benzenesulfonamide hydrochloride (298 mg, 1.38 mmol) and DIPEA (0.43 mL, 3.12 mmol). The reaction is stirred at 108° C. for 16 h. After this time the solution is allowed to cool, resulting in a thick precipitate that is filtered and washed with diethyl ether to give 330 mg of pure product as a beige solid (67%).

Compound 108: 4-{[3-(4-Hydroxy-phenyl)-5-methyl-imidazo[1,2-a]pyrazin-8-ylamino]-methyl}-benzenesulfonamide A mixture of 4-[(3-Bromo-5-methyl-imidazo[1,2-a]pyrazin-8-ylamino)-methyl]-benzenesulfonamide (0.1 g, 0.252 mmol), 4-(4,4,5,5-tetramethyl-[1,3,2]dioxaborolan-2-yl)-phenol (0.061 g, 0.277 mmol), K₂CO₃ 1.5M in water (0.34 mL, 0.504 mmol), Pd(OAc)₂ (3.0 mg, 0.013 mmol), and (oxidi-2,1-phenylene)bis(diphenylphosphine) (14 mg, 0.026 mmol) in DMF 1 mL is stirred at 88° C. overnight. The reaction mixture is filtered through cotton, diluted with AcOEt, washed with water, the organic layer dried with MgSO₄ anh. filtered and evaporated. The crude mixture is purified by prep. HPLC under acid conditions using a gradient of 0.1% formic acid in H₂O/0.1% formic acid in Acetonitrile (95/5:5 min, 9/1:13 min, 0/1:4 min) to give 4-{[3-(4-hydroxy-phenyl)-5-methyl-imidazo[1,2-a]pyrazin-8-ylamino]-methyl}-benzenesulfonamide as a brown oil, (36.5 mg) LC-MS m/z 410 [M+H]⁺.

Compound 109

By essentially the same procedures described for General Method 4 and as used to prepare Compound 108 the compound in Table 9 can be prepared.

TABLE 9

| Compound # | Structure | LCMS: MH⁺ |
|---|---|---|
| 109 | 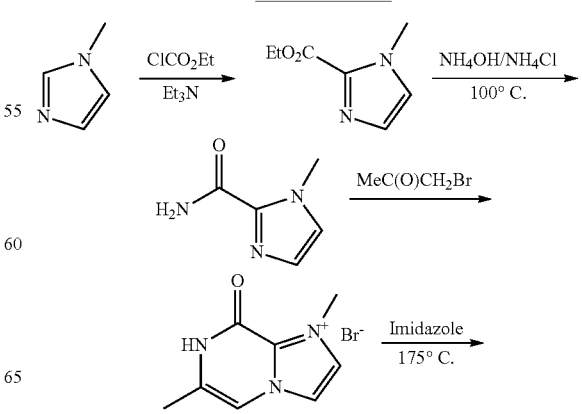 | m/z 440 [M + H]⁺ |

General Method 5

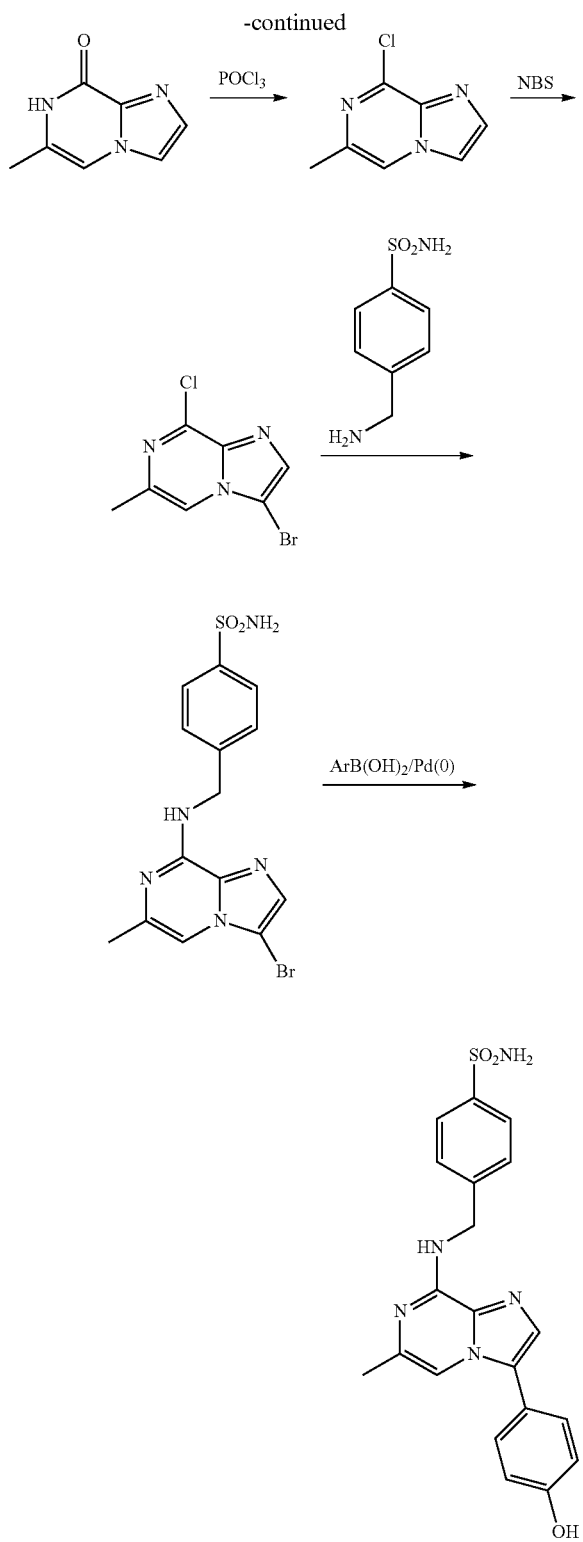

Triethyl amine (50 mL) is added to a solution of methyl imidazol (16.3 g, 199 mmol) in acetonitrile (100 mL), then it is cooled to −30° C. A solution of ethyl chloroformate (31 mL, 328 mmol) in acetonitrile (50 mL) is added slowly keeping the temperature bellow 10° C. The reaction mixture is concentrated and diluted in water and extracted with chloroform, dried with $MgSO_4$ anh, filtered and evaporated. Recrystallisation from ether yields 1-Methyl-1H-imidazole-2-carboxylic acid ethyl ester as an orange oil (15.5 g, 51%).

1-Methyl-1H-imidazole-2-carboxylic acid amide $NH_4Cl$ (0.150 g, 2.8 mmol) is added to a solution of 1-methyl-1H-imidazole-2-carboxylic acid ethyl ester (15.5 g, 101 mmol) in ammonium hydroxide 35% (112 mL) and the reaction is stirred for 6 h at 100° C. in a sealed reaction flask. The reaction is cooled to 0° C. and the solid formed filtered and washed with ice water and ether to give 1-methyl-1H-imidazole-2-carboxylic acid amide as brown crystals (6.9 g, 55%).

1,6-Dimethyl-8-oxo-7,8-dihydro-imidazol[1,2-a]pyrazin-1-ium bromide salt

A mixture of 1-Methyl-1H-imidazole-2-carboxylic acid amide (3.0 g, 14.3 mmol), bromoacetone (2.36 g, 17.2 mmol) and acetonitrile (40 mL) is stirred overnight at 80° C. The solid formed is filtered and washed with acetonitrile to give 1,6-dimethyl-8-oxo-7,8-dihydro-imidazo[1,2-a]pyrazin-1-ium bromide salt (4.3 g, 86%).

6-Methyl-7H-imidazol[1,2-a]pyrazin-8-one

A mixture of 1,6-dimethyl-8-oxo-7,8-dihydro-imidazo[1,2-a]pyrazin-1-ium bromide salt (4.3 g, 16.4 mmol) and imidazole (20.4 g, 310 mmol) is stirred at 175° C. for 20 h. After this time the reaction mixture is cooled down to 100° C. and poured into ice-water with vigorous stirring. No precipitation is observed therefore the solvent is removed and the imidazole distilled off under vacuum at approx. 130° C. The solid remaining is triturated with DCM to give 6-methyl-7H-imidazo[1,2-a]pyrazin-8-one as a brown solid (970 mg). The mother liq. are purified by column chromatography using a gradient of (DMC/MeOH:99/1 to 95/5) to give a further 667 mg of 6-methyl-7H-imidazo[1,2-a]pyrazin-8-one as a pale yellow solid (1.66 g, 68%).

8-Chloro-6-methyl-imidazo[1,2-a]pyrazine

Pyridine (0.4 mL, 4.9 mmol) was added to a solution of 6-methyl-7H-imidazo[1,2-a]pyrazin-8-one (0.97 g, 6.5 mmol) in $POCl_3$ (19 mL) and the reaction is stirred at 120° C. under $N_2$ atmosphere for 4 h 30 min. The reaction is cooled to 60° C. and poured into 60 g of ice and stirred for 1 h. The solution is neutralized with NaOH (10%), extracted with $CHCl_3$/IPA 9/1, dried with $MgSO_4$ anh., filtered and concentrated. The crude product is purified by column chromatography using a gradient of (DCM/MeOH:99/1 to 95/5) to give 8-chloro-6-methyl-imidazo[1,2-a]pyrazine as a pale yellow solid (0.383 g, 35%).

3-Bromo-8-chloro-6-methyl-imidazo[1,2-a]pyrazine

N-bromosuccinimide (348 mg, 1.96 mmol) is added to a solution of 8-chloro-6-methyl-imidazo[1,2-a]pyrazine (337 mg, 2.02 mmol) in DCM (6.1 mL) and the reaction is stirred at 40° C. for 10 min and then at room temperature for 1 h 30 min. The reaction mixture is diluted with DCM and washed twice with 4 mL of $Na_2CO_3$ sat., dried with $MgSO_4$ anh., filtered and concentrated in vacuo to give 3-bromo-8-chloro-6-methyl-imidazo[1,2-a]pyrazine as a yellow solid (470 mg, 95%).

4-[(3-Bromo-6-methyl-imidazo[1,2-a]pyrazin-8-ylamino)-methyl]-benzenesulfonamide To a solution of 3-bromo-8-chloro-6-methyl-imidazo[1,2-a]pyrazine (350 mg, 1.42 mmol) in $^{t}$BuOH (3 mL) is added 4-aminomethyl-benzenesulfonamide hydrochloride (334 mg, 1.42 mmol) and DIPEA (0.49 mL, 2.82 mmol). The reaction is stirred at 108° C. for 16 h. After this time the solution is allowed to cool, resulting in a thick precipitate that is filtered and washed with diethyl ether to give 4-[(3-bromo-6-methyl-imidazo[1,2-a]pyrazin-8-ylamino)-methyl]-benzenesulfonamide as a beige solid (420 mg, 75%).

Compound 110: 4-{[3-(4-Hydroxy-phenyl)-6-methyl-imidazo[1,2-a]pyrazin-8-ylamino]-methyl}-benzenesulfonamide A mixture of 4-[(3-bromo-6-methyl-imidazo[1,2-a]pyrazin-8-ylamino)-methyl]-benzenesulfonamide (0.1 g, 0.252 mmol), 4-(4,4,5,5-tetramethyl-[1,3,2]dioxaborolan-2-yl)-phenol (0.061 g, 0.277 mmol), $K_2CO_3$ 1.5M in water (0.34 mL, 0.504 mmol), Pd(OAc)$_2$ (3.0 mg, 0.013 mmol), and (oxidi-2,1-phenylene)bis(diphenylphosphine) (14 mg, 0.026 mmol) in DMF 1 mL was stirred at 88° C. overnight. Then the reaction mixture is filtered through cotton, diluted with AcOEt, washed with water, the organic layer dried with MgSO$_4$ (anhydrous), filtered and evaporated. The crude mixture is purified by prep. HPLC under acid conditions using a gradient of 0.1% formic acid in H$_2$O/0.1% formic acid in acetonitrile (95/5:5 min, 9/1:13 min, 0/1:4 min) to give 4-{[3-(4-hydroxy-phenyl)-6-methyl-imidazo[1,2-a]pyrazin-8-ylamino]-methyl}-benzenesulfonamide as a brown oil (30.2 mg) LC-MS m/z 410 [M+H]$^+$.

Compounds III-112

Using methods as described for General Method 5 and for the preparation of Compound 110, the compounds below may be prepared

TABLE 10

| Compound # | Structure | LCMS: MH$^+$ |
|---|---|---|
| 111 | (4-{[(6-methyl-3-(3-fluoro-4-hydroxyphenyl)imidazo[1,2-a]pyrazin-8-yl)amino]methyl}benzenesulfonamide) | m/z 428 [M + H]$^+$ |
| 112 | (4-{[(6-methyl-3-(4-hydroxy-3-methoxyphenyl)imidazo[1,2-a]pyrazin-8-yl)amino]methyl}benzenesulfonamide) | m/z 440 [M + H]$^+$ |

Compounds 113 and 114

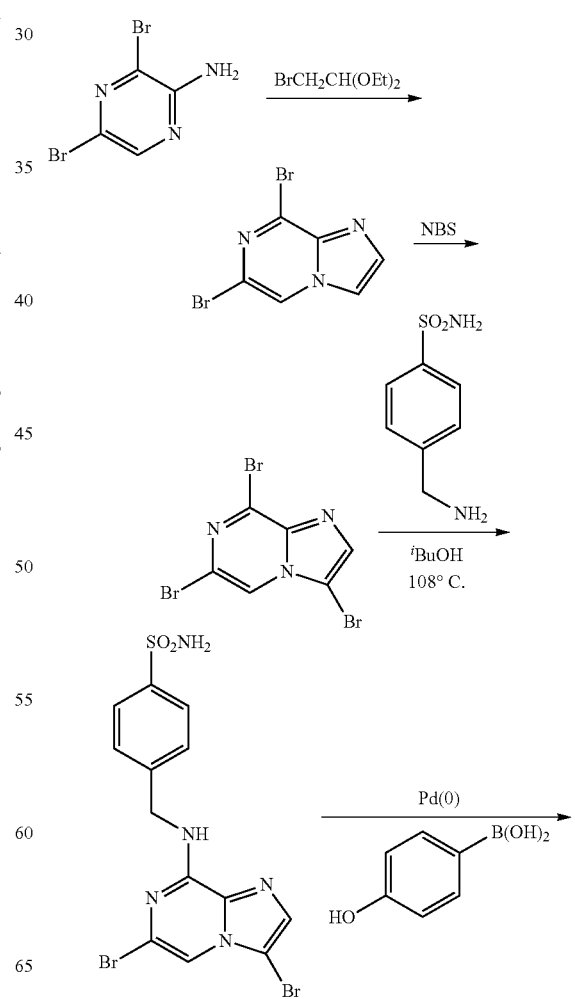

129

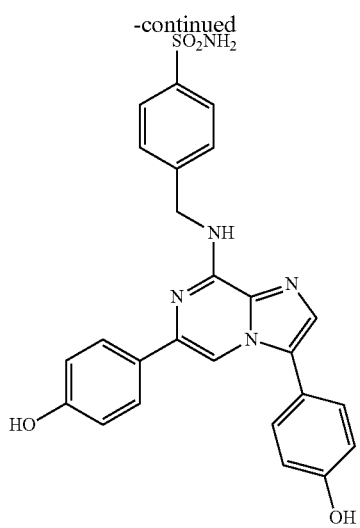

3,6,8-Tribromo-imidazo[1,2-a]pyrazine

N-bromosuccinimide (1.81 g, 10.15 mmol) was added to a solution of 6,8-Dibromo-imidazo[1,2-a]pyrazine (2.0 g, 10.15 mmol) in dichloromethane (40 ml). The reaction was stirred at room temperature over night then diluted with dichloromethane (100 ml) and washed with saturated aqueous sodium hydrogen carbonate (2×50 ml) and brine (50 ml). The organic layer was dried (MgSO$_4$), filtered and concentrated in vaccuo. The product, 3,6,8-Tribromo-imidazo[1,2-a]pyrazine was obtained as a pink solid (2.77 g), sufficiently pure to be used in subsequent reactions.

Compound 113: 4-[(3,6-Dibromo-imidazo[1,2-a]pyrazin-8-ylamino)-methyl]-benzenesulfonamide 4-Aminomethyl-benzenesulfonamide hydrochloride (2.22 g, 10 mmol) was added to a solution of 3,6,8-Tribromo-imidazo[1,2-a]pyrazine (2.77 g, 10 mmol) and DIPEA (3.65 ml, 21 mmol) in $^t$BuOH (20 mL). The reaction was stirred at 108° C. for 3 h then allowed to cool to room temperature. The precipitate formed was filtered and washed with diethyl ether to give 4-[(3,6-Dibromo-imidazo[1,2-a]pyrazin-8-ylamino)-methyl]-benzenesulfonamide as a pale brown solid (3.5 g, 76% yield). LC-MS m/z 462 [M+H]$^+$.

Compound 114: 4-{[3,6-Bis-(4-hydroxy-phenyl)-imidazo[1,2-a]pyrazin-8-ylamino]-methyl}-benzenesulfonamide A microwave tube was charged with 4-[(3,6-Dibromo-imidazo[1,2-a]pyrazin-8-ylamino)-methyl]-benzenesulfonamide (0.17 g, 0.379 mmol), 4-(4,4,5,5-Tetramethyl-[1,3,2]dioxaborolan-2-yl)-phenol (0.175 g, 0.79 mmol), Na$_2$CO$_3$ (0.10 g, 0.95 mmol), Pd(OAc)$_2$ (7 mg, 0.028 mmol), and (Oxidi-2,1-phenylene)bis(diphenylphosphine) (20 mg, 0.0379 mmol), suspended in a mixture of DMF (3 mL) and water (1 ml). The tube was sealed under a nitrogen atmosphere then heated to 130° C. for 20 min. The reaction was filtered, diluted with AcOEt and washed with water. The organic layer was dried with MgSO$_4$ anh. filtered and evaporated. The crude mixture was purified by prep. HPLC under acid conditions using a gradient of 0.1% formic acid in H$_2$O/0.1% formic acid in Acetonitrile (95/5:5 min, 9/1:13 min, 0/1:4 min) to give 4-{[3,6-Bis-(4-hydroxy-phenyl)-imidazo[1,2-a]pyrazin-8-ylamino]-methyl}-benzenesulfonamide as a brown solid (21 mg,). LC-MS m/z 488 [M+H]$^+$.

TABLE 11

| Compound # | Structure | LCMS: MH$^+$ |
|---|---|---|
| 113 | (4-[(3,6-Dibromo-imidazo[1,2-a]pyrazin-8-ylamino)-methyl]-benzenesulfonamide structure) | m/z 462 [M + H]$^+$ |
| 114 | (4-{[3,6-Bis-(4-hydroxy-phenyl)-imidazo[1,2-a]pyrazin-8-ylamino]-methyl}-benzenesulfonamide structure) | m/z 488 [M + H]$^+$ |

Further examples of the invention can be prepared using the procedures outlined below:

The required scaffolds can be prepared using the General Methods 1-5 described above or can be prepared using other methods that will be obvious to those skilled in the art The appropriate amines for use in these General Methods are either available from commercial sources or can be prepared using the general method described below or other methods that will be obvious to those skilled in the art.

General Method 6

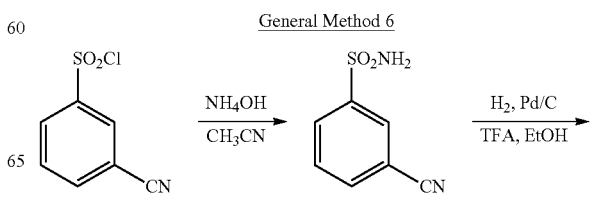

131

-continued

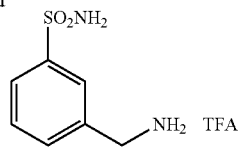

3-cyano-benzenesulfonamide

NH$_4$OH (22 mL, excess) can be added to a solution of 3-cyanobenzene-1-sulfonyl chloride (1.0 g, 4.97 mmol) in acetonitrile (22 mL) and the reaction stirred overnight at r.t. The reaction can be concentrated and the solid obtained washed with water to give 500 mg of product. The water phase can be extracted with AcOEt, dried with MgSO$_4$ anh, filtered and evaporated to give 400 mg of product that can be combined with the solid obtained before (0.90 g, 99%).

3-Aminomethyl-benzenesulfonamide TFA salt

TFA (5 mL) can be added to a solution of 3-cyano-benzenesulfonamide (0.90 g, 4.94 mmol) in EtOH (50 mL) followed by Pd/C (100 mg) and the mixture hydrogenated at 40 psi and r.t. for 20 h. The reaction mixture can be filtered through celite and the solvent concentrated to give 3-Aminomethyl-benzenesulfonamide TFA salt as a white solid in quantitative yield.

A representative set of suitable amines that can be prepared using this methodology

| Intermediate # | Structure |
|---|---|
| I | 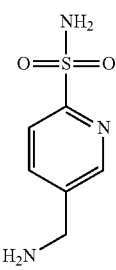 |
| II | 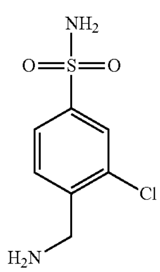 [SMILES: NCc1ccc(S(N)(=O)=O)cc1Cl] |
| III | 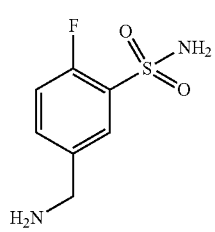 [SMILES: NCc1ccc(F)c(S(N)(=O)=O)c1] |

132

-continued

| Intermediate # | Structure |
|---|---|
| IV | 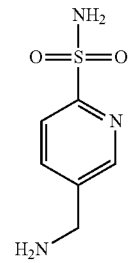 |

The following compounds as shown in table 12 below, can be prepared using the methods disclosed here or by using methods that will be obvious to those skilled in the art.

TABLE 12

| Compound # | Structure |
|---|---|
| 115 | 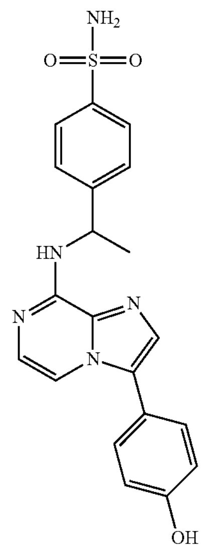 [SMILES: CC(Nc1nccn2c(-c3ccc(O)cc3)cnc12)c1ccc(S(N)(=O)=O)cc1] |
| 116 | 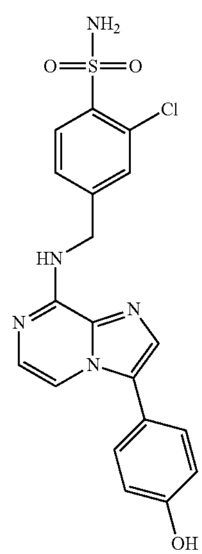 [SMILES: NS(=O)(=O)c1ccc(CNc2nccn3c(-c4ccc(O)cc4)cnc23)cc1Cl] |

TABLE 12-continued
| Compound # | Structure |
|---|---|
| 117 | 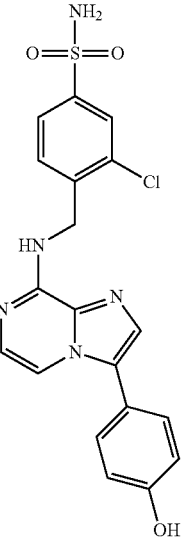 |
| 118 | 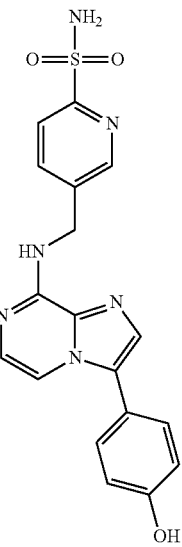 |
| 119 | 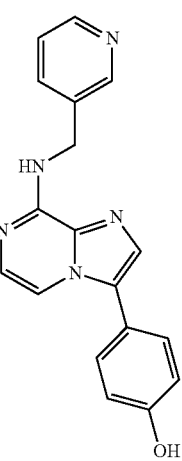 |
TABLE 12-continued
| Compound # | Structure |
|---|---|
| 120 | 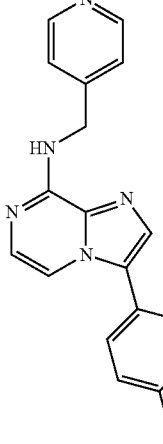 |
| 121 | 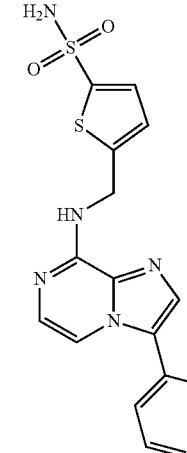 |
| 122 | 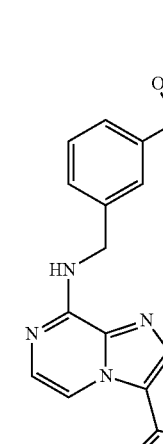 |

TABLE 12-continued

| Compound # | Structure |
|---|---|
| 123 | (4-sulfamoylbenzyl)amino-2-methyl-3-(3,4-dimethoxyphenyl)imidazo[1,2-a]pyrazine |
| 124 | (4-sulfamoylbenzyl)amino-2-methyl-3-(4-methoxyphenyl)imidazo[1,2-a]pyrazine |
| 125 | 1-(4-sulfamoylphenyl)ethylamino-2-methyl-3-(4-hydroxyphenyl)imidazo[1,2-a]pyrazine |
| 126 | (2-chloro-4-sulfamoylbenzyl)amino-2-methyl-3-(4-hydroxyphenyl)imidazo[1,2-a]pyrazine |
| 127 | (2-chloro-4-sulfamoylbenzyl)amino-2-methyl-3-(4-hydroxyphenyl)imidazo[1,2-a]pyrazine |

TABLE 12-continued

| Compound # | Structure |
| --- | --- |
| 128 | (structure) |
| 129 | (structure) |
| 130 | (structure) |
| 131 | (structure) |
| 132 | (structure) |
| 133 | (structure) |

TABLE 12-continued

| Compound # | Structure |
|---|---|
| 134 | (5-sulfamoylthiophen-2-yl)methylamino-2-methyl-3-(4-hydroxyphenyl)imidazo[1,2-a]pyrazine |
| 135 | 4-sulfamoylbenzylamino-2-methyl-3-(3-methyl-4-hydroxyphenyl)imidazo[1,2-a]pyrazine |
| 136 | 4-sulfamoylbenzylamino-2-methyl-3-(2-fluoro-4-hydroxyphenyl)imidazo[1,2-a]pyrazine |
| 137 | 3-sulfamoylbenzylamino-2-methyl-3-(4-hydroxyphenyl)imidazo[1,2-a]pyrazine |
| 138 | 3-sulfamoylbenzylamino-2-methyl-3-(3-fluoro-4-hydroxyphenyl)imidazo[1,2-a]pyrazine |
| 139 | 3-sulfamoylbenzylamino-2-methyl-3-(3-methoxy-4-hydroxyphenyl)imidazo[1,2-a]pyrazine |

TABLE 12-continued
| Compound # | Structure |
|---|---|
| 140 | 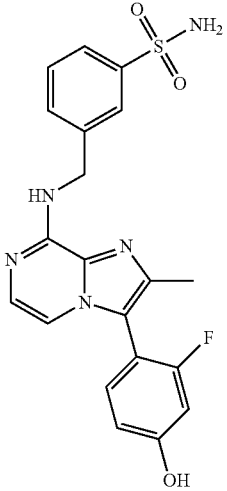 [SMILES: Cc1nc2c(NCc3cccc(S(N)(=O)=O)c3)nccn2c1-c1ccc(O)cc1F] |
| 141 | 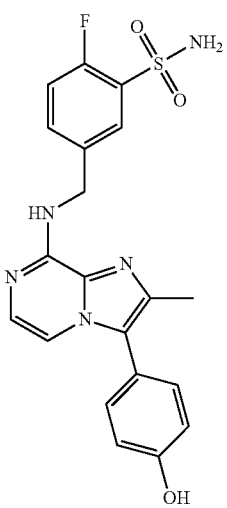 [SMILES: Cc1nc2c(NCc3ccc(F)c(S(N)(=O)=O)c3)nccn2c1-c1ccc(O)cc1] |
| 142 | 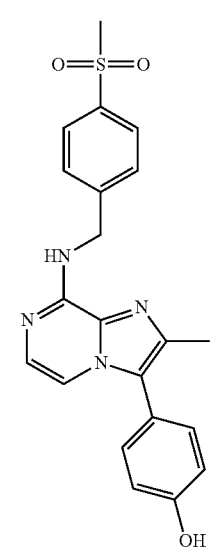 [SMILES: Cc1nc2c(NCc3ccc(S(C)(=O)=O)cc3)nccn2c1-c1ccc(O)cc1] |
| 143 | 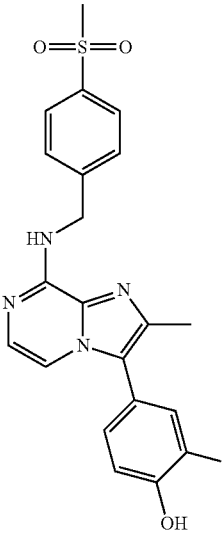 |
| 144 | 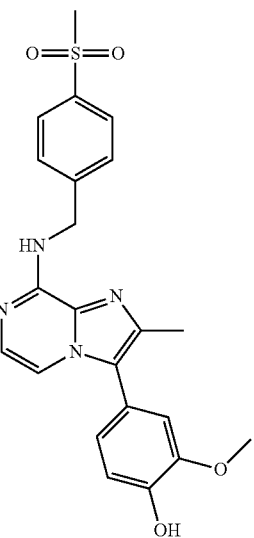 |
| 145 | 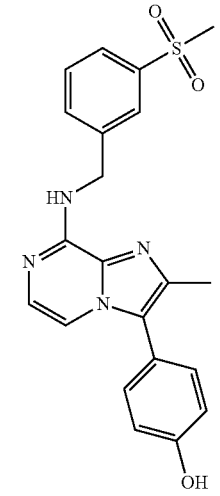 [SMILES: Cc1nc2c(NCc3cccc(S(C)(=O)=O)c3)nccn2c1-c1ccc(O)cc1] |

TABLE 12-continued

| Compound # | Structure |
|---|---|
| 146 | *(structure: 4-hydroxyphenyl-imidazopyrazine with 2-methyl substituent, 8-NH-CH2-phenyl-SO2NHCH3)* |
| 147 | *(structure: 4-hydroxyphenyl-imidazopyrazine with 2-methyl substituent, 8-NH-CH2-phenyl-SO2N(CH3)2)* |
| 148 | *(structure: 4-hydroxyphenyl-imidazopyrazine with 2-methyl substituent, 8-NH-CH2-phenyl-SO2NH-CH2CH2-N(CH3)2)* |
| 149 | *(structure: 4-hydroxyphenyl-imidazopyrazine with 2-methyl substituent, 8-NH-CH2-phenyl-SO2-morpholine)* |

TABLE 12-continued
| Compound # | Structure |
|---|---|
| 150 | 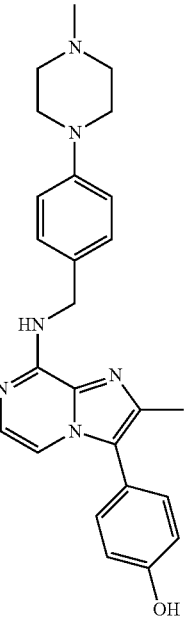 |
| 151 | 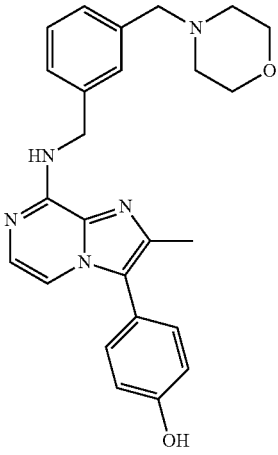 [SMILES: Cc1nc2c(NCc3cccc(CN4CCOCC4)c3)nccn2c1-c1ccc(O)cc1] |
| 152 | 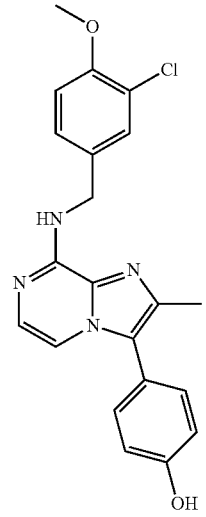 [SMILES: COc1ccc(CNc2nccn3c(-c4ccc(O)cc4)c(C)nc23)cc1Cl] |
TABLE 12-continued
| Compound # | Structure |
|---|---|
| 153 | 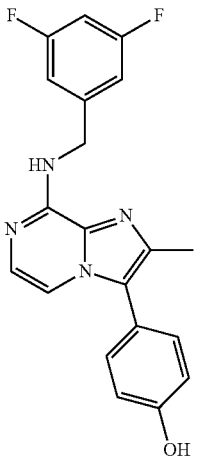 [SMILES: Cc1nc2c(NCc3cc(F)cc(F)c3)nccn2c1-c1ccc(O)cc1] |
| 154 | 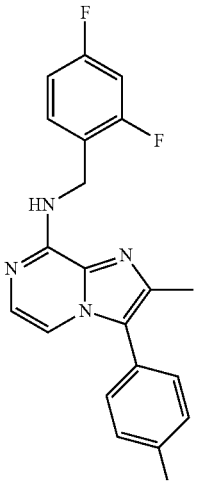 |
| 155 | 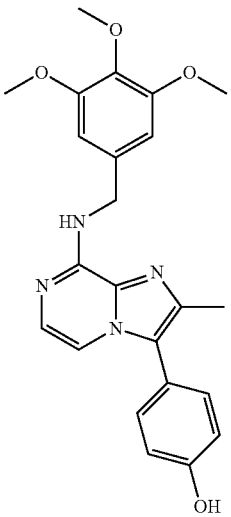 |

TABLE 12-continued
| Compound # | Structure |
|---|---|
| 156 | 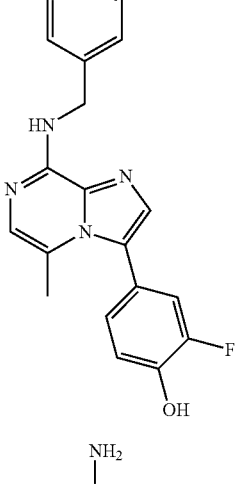 |
| 157 | |
| 158 | |// placeholder TABLE 12-continued
| Compound # | Structure |
|---|---|
| 162 | |
| 163 | |
| 164 | |
| 165 | |
| 166 | |
| 167 | |
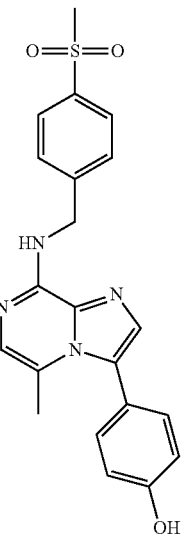

TABLE 12-continued
| Compound # | Structure |
|---|---|
| 168 | 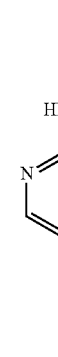 |
| 169 | 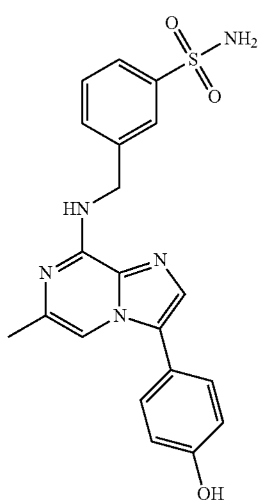 [SMILES: Cc1cn2c(-c3ccc(O)cc3)cnc2c(NCc2cccc(S(N)(=O)=O)c2)n1] |
| 170 | 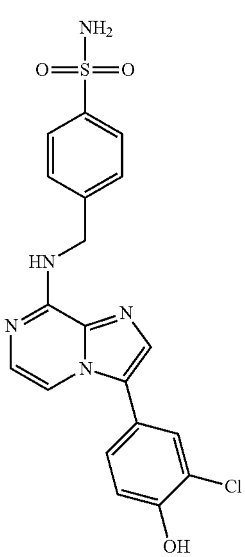 [SMILES: NS(=O)(=O)c1ccc(CNc2nccn3c(-c4ccc(O)c(Cl)c4)cnc23)cc1] |
| 171 | 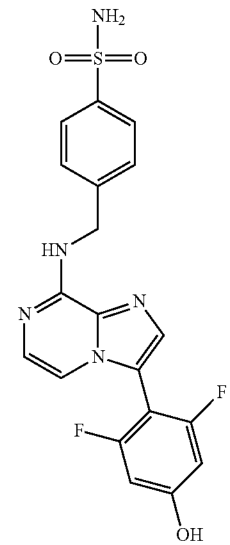 [SMILES: NS(=O)(=O)c1ccc(CNc2nccn3c(-c4c(F)cc(O)cc4F)cnc23)cc1] |
| 172 | 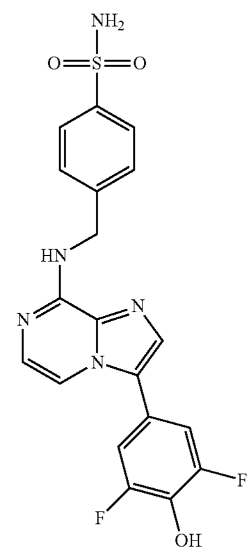 [SMILES: NS(=O)(=O)c1ccc(CNc2nccn3c(-c4cc(F)c(O)c(F)c4)cnc23)cc1] |
| 173 | 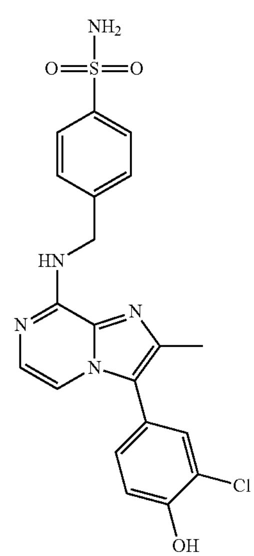 [SMILES: Cc1nc2c(NCc3ccc(S(N)(=O)=O)cc3)nccn2c1-c1ccc(O)c(Cl)c1] |

TABLE 12-continued

| Compound # | Structure |
|---|---|
| 174 | 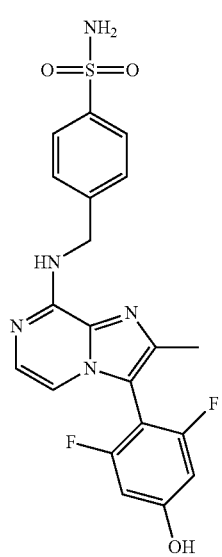 [SMILES: Cc1nc2c(NCc3ccc(S(N)(=O)=O)cc3)nccn2c1-c1c(F)cc(O)cc1F] |
| 175 | 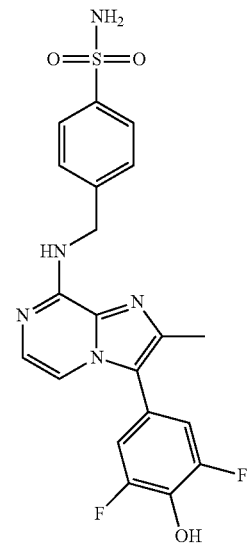 |

Biological Data

The biological activity of the compounds of the invention may be assessed using any appropriate assays known to a person of skill in the art.

It is also possible to obtain screening data on the compounds from companies and institutions that offer screening services e.g. via the NIAID division of Microbiology and Infectious diseases (DMID) Antiviral Evaluation Resources (http://niaid-aacf.org/index.html) which includes services provided by Georgetown State University The ability of a compound to inhibit HCV replication can be measured in vitro or using animal models using models and assays well known to those of skill in the art (e.g. Pietschmann et al, Clin Liver Dis. 7(1)c23-43, 2003). In vitro techniques for measuring the ability of a compound to inhibit HCV replication involve using HCV or an HCV replicon. Because HCV is difficult to grow in culture, particular in vitro techniques employ an HCV replicon.

An HCV replicon is an RNA molecule able to autonomously replicate in a cultured cell, such as Huh7. The HCV replicon expresses the HCV derived components of the replication machinery and contains cis-elements required for replication in a cultured cell.

The production and use of HCV replicons are described in different references (see for example, Lohmann et al., *Science*, 285:110-113, 1999; Blight et al., *Science*, 290:1972-1974, 2000; Lohmann et al, *Journal of Virology*, 75:1437-1449, 2001; Pietschmann et al, *Journal of Virology*, 75:1252-1264, 2001; Grobler et al, *J. Biol. Chem.*, 278:16741-16746, 2003; Murray et al., *J. Viol*, 77(5):2928-2935, 2003; Zuck et al, *Anal Briochem* 334(2):344-355, 2004; Ludmerer et al, *Antimicrob. Agents Chemother.* 49(5):2059-69, 2005; Rice et al, WO 01/89364; Bichko, WO 02/238793; Kukolj et al, WO 02/052015; De Francesco et al., WO 02/059321; Glober et al., WO 04/074507 and Bartenschlager U.S. Pat. No. 6,630,343).

The ability of a compound to inhibit HCV replication can be measured in naturally occurring or artificial animal models susceptible to HCV infection. Only a few animals such as humans and chimpanzees are susceptible to HCV infection. Chimpanzees have been used as animal models for determining the effect of a compound on HCV infection.

Artificial animal models susceptible to HCV infection have been produced by transplanting human liver cells into a mouse (Pietschmann et al., *Clin Liver Dis.*, 7(1):23-43, 2003). The use of transgenic mice with chimeric mouse-human livers provides for a small animal model.

It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular toxicity.

The following compounds have been or can be prepared according to the synthetic methods described herein. Table 13 below lists a number of compounds which exhibit activity in anti-viral assays ($EC_{50}$) together with their cytotoxicity measurement ($CC_{50}$).

Semi-quantitative scores:

| $EC_{50}$ | |
|---|---|
| +++ | <1 μM |
| ++ | 1-20 μM |
| + | >20 μM |
| $CC_{50}$ | |
| ** | <35 μM |
| * | >35 μM |

TABLE 13

| Compound # | $EC_{50}$ Activity | $CC_{50}$ Activity |
|---|---|---|
| 1 | +++ | * |
| 2 | ++ | ** |
| 3 | + | * |
| 4 | ++ | * |
| 5 | ++ | * |
| 6 | ++ | * |
| 7 | ++ | * |
| 8 | ++ | ** |
| 9 | +++ | * |
| 10 | ++ | * |

TABLE 13-continued

| Compound # | EC$_{50}$ Activity | CC$_{50}$ Activity |
|---|---|---|
| 11 | ++ | * |
| 12 | ++ | * |
| 13 | ++ | ** |
| 14 | ++ | * |
| 15 | + | * |
| 16 | ++ | * |
| 17 | ++ | ** |
| 18 | ++ | * |
| 19 | ++ | * |
| 20 | +++ | ** |
| 21 | ++ | ** |
| 22 | ++ | * |
| 23 | ++ | * |
| 24 | ++ | ** |
| 25 | +++ | * |
| 26 | ++ | * |
| 27 | ++ | * |
| 28 | + | * |
| 29 | ++ | ** |
| 30 | + | * |
| 31 | ++ | * |
| 32 | ++ | * |
| 33 | ++ | * |
| 34 | ++ | ** |
| 35 | ++ | ** |
| 36 | ++ | ** |
| 37 | ++ | * |
| 38 | ++ | * |
| 39 | ++ | ** |
| 40 | ++ | * |
| 41 | ++ | ** |
| 42 | ++ | ** |
| 43 | + | * |
| 44 | ++ | ** |
| 45 | ++ | * |
| 46 | ++ | * |
| 47 | ++ | ** |
| 48 | ++ | * |
| 49 | ++ | ** |
| 50 | ++ | * |
| 51 | + | * |
| 52 | + | * |
| 53 | ++ | ** |
| 54 | ++ | * |
| 55 | ++ | ** |
| 56 | +++ | ** |
| 57 | +++ | * |
| 58 | ++ | ** |
| 59 | ++ | ** |
| 60 | ++ | ** |
| 61 | ++ | ** |
| 62 | ++ | ** |
| 63 | ++ | ** |
| 64 | ++ | ** |
| 65 | ++ | ** |
| 66 | ++ | ** |
| 67 | ++ | ** |
| 68 | ++ | ** |
| 69 | ++ | ** |
| 70 | ++ | ** |
| 71 | ++ | ** |
| 72 | ++ | ** |
| 73 | ++ | ** |
| 74 | ++ | ** |
| 75 | ++ | ** |
| 76 | ++ | ** |
| 77 | ++ | ** |
| 78 | ++ | ** |
| 79 | ++ | ** |
| 80 | ++ | ** |
| 81 | ++ | ** |
| 82 | ++ | ** |
| 83 | ++ | ** |
| 84 | ++ | ** |
| 85 | ++ | ** |
| 86 | ++ | ** |
| 87 | ++ | ** |
| 88 | +++ | * |
| 89 | + | * |
| 90 | ++ | ** |
| 91 | +++ | * |
| 92 | ++ | * |
| 93 | ++ | * |
| 94 | ++ | * |
| 95 | ++ | ** |
| 96 | + | * |
| 97 | ++ | ** |
| 98 | ++ | ** |
| 99 | ++ | ** |
| 100 | ++ | * |
| 101 | ++ | * |
| 102 | ++ | * |
| 103 | ++ | * |
| 104 | ++ | * |
| 105 | +++ | * |
| 106 | +++ | * |
| 107 | ++ | * |
| 108 | +++ | ** |
| 109 | +++ | ** |
| 110 | +++ | ** |
| 111 | +++ | * |
| 112 | +++ | ** |
| 113 | + | * |
| 114 | +++ | ** |

Particular compounds have been profiled against a range of other viruses and show activity against other positive-strand RNA viruses—the picornaviruses; rhinoviruses (HRV), poliovirus (Sb) and coxsackie B virus (CVB).

The biological activity of the compounds of the invention may be assessed using any appropriate assays known to a person of skill in the art.

The compounds as disclosed herein may be tested for their activity (IC$_{50}$/other scores) against picornaviruses using methods known to those of skill in the art. Typical methods which may be used include: against rhinovirus, poliovirus and coxsackie virus (e.g. Sidwell and Huffman *Appl. Microbiol.* 22: 797-801, 1971).), against rhinovirus and coxsackie virus (Makarov et al *Journal of Antimicrobial Chemotherapy*, 55: 483-488, 2005) etc. However, any suitable assays may be used.

It is also possible to undertake screening of the compounds with companies and institutions that offer screening agreements e.g is the NIAID division of Microbiology and Infectious diseases (DMID) Antiviral Evaluation Resources (http://niaid-aacf.org/index.html) which includes services provided by Utah State University It will be appreciated that using different assay conditions may result in absolute numbers that differ from those reported herein

| EC$_{50}$ | |
|---|---|
| +++ | <1 µM |
| ++ | 1-20 µM |
| + | >20 µM |
| CC$_{50}$ | |
| ** | <35 µM |
| * | >35 µM |

TABLE 14

| Virus | HCV | CVB-2 | Sb-1 | YFV | Influenza | RSV | VSV | HSV-1 | HIV |
|---|---|---|---|---|---|---|---|---|---|
| Compound 1 EC$_{50}$(µM) | +++ | +++ | +++ | ++ | + | + | + | + | ++ |
| Compound 1 CC$_{50}$(µM) | * | * | * | ** | * | * | * | * | ** |
| Cells | Huh7 | Vero | Vero | BHK-21 | MDCK | Vero | Vero | Vero | MT-4 |

| EC$_{50}$ | |
|---|---|
| +++ | <1 µg/mL |
| ++ | 1-20 µg/mL |
| + | >20 µg/mL |
| CC$_{50}$ | |
| ** | <35 µg/mL |
| * | >35 µg/mL |

TABLE 15

| Compound # | Virus | HRV-2 (HeLa cells) | HRV-14 (HeLa cells) | HRV clinical isolate (HeLa cells) |
|---|---|---|---|---|
| 1 | EC$_{50}$(µg/mL) | +++ | +++ | +++ |
| 1 | CC$_{50}$(µg/mL) | * | * | * |
| 106 | EC$_{50}$(µg/mL) | +++ | +++ | +++ |
| 106 | CC$_{50}$(µg/mL) | * | * | * |

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS® /DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. The compound of Formula(VA) or Formula (VB) below:

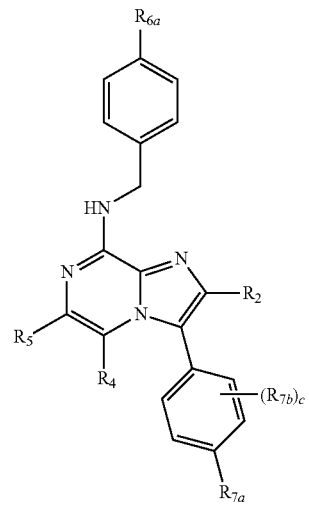

(VA)

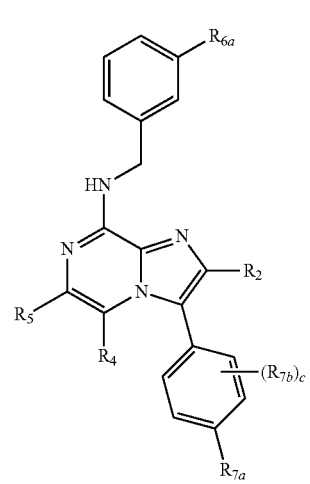

(VB)

wherein $R_2$, $R_4$ and $R_5$ are independently selected from H, methyl and ethyl;

$R_{6a}$ is SO$_2$R$_8$;

$R_{7a}$ is selected from OH, OCH$_3$, halogen, NH$_2$, CH$_2$—OH and NHCOR$_8$;

each $R_{7b}$ is selected from OH, halogen, CN, $NO_2$, $C_1$-$C_6$ alkyl, $C_1$-$C_6$ alkoxy, substituted $C_1$-$C_6$ alkoxy, $CF_3$, $OCF_3$, $C_1$-$C_6$ alkyl-OH, $NHSO_2R_9$, $NHCOR_8$, and $NR_9R_{10}$;

$R_8$ is selected from $C_1$-$C_6$ alkyl, or $NR_9R_{10}$;

$R_9$ and $R_{10}$ are each independently selected from H and $C_1$-$C_6$ alkyl; and c is 0 or 1;

or a pharmaceutically acceptable salt thereof;

wherein substituted $C_1$-$C_6$ alkoxy refers to $OCF_3$, $OCH_2CF_3$, $OCH_2Ph$, $OCH_2$-cyclopropyl, $OCH_2CH_2OH$, or $OCH_2CH_2NMe_2$.

2. The compound according to claim 1, wherein $R_{7a}$ is selected from OH, $NH_2$ and $OCH_3$.

3. The compound according to claim 1, wherein $R_{6a}$ is $SO_2R_8$, and $R_8$ is $C_1$-$C_6$ alkyl.

4. The compound according to claim 1, wherein $R_{7b}$ is selected from OH, halogen, $NO_2$, $NH_2$, $C_1$-$C_6$ alkyl, $C_1$-$C_6$ alkoxy, $C_1$-$C_6$ alkyl-OH, $NHSO_2R_9$ and $NHCOR_8$.

5. The compound according to claim 1, wherein $R_2$, $R_4$ and $R_5$ are selected from H and $CH_3$.

6. The compound according to claim 1, wherein $R_{6a}$ is $SO_2R_8$, and $R_8$ is $CH_3$.

7. A pharmaceutical composition comprising a pharmaceutically acceptable carrier and a pharmaceutically effective amount of a compound according to claim 1.

8. The pharmaceutical composition of claim 7, wherein the carrier is selected from a parenteral carrier, an oral carrier and a topical carrier.

9. A method of treatment of a viral infection, comprising administering to a subject, a therapeutically effective amount of a compound according to claim 1, wherein the viral infection is selected from hepatitis C virus (HCV), poliovirus (Sb-1) and coxsackie B virus (CVB-2).

10. A compound of Formula (VIA) or Formula (VIB) below:

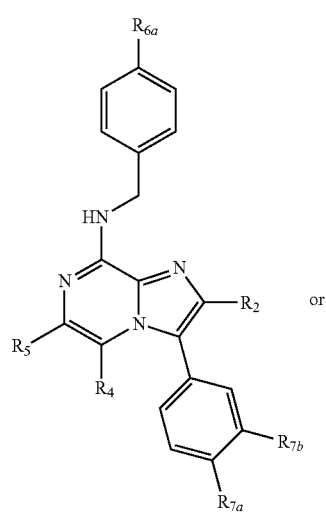

(VIA)

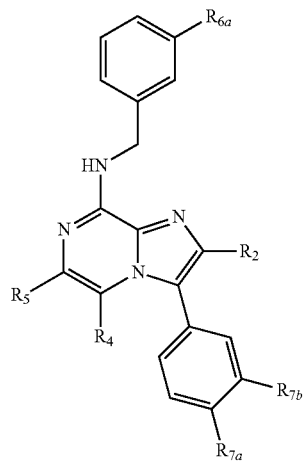

(VIB)

wherein
$R_2$, $R_4$ and $R_5$ are independently selected from H, methyl and ethyl;

$R_{6a}$ is $SO_2R_8$;

$R_8$ is selected from $C_1$-$C_6$ alkyl and $NR_9R_{10}$;

$R_9$ and $R_{10}$ may be the same or different and are selected from H and $C_1$-$C_6$ alkyl;

$R_{7b}$ is selected from H, OH, halogen, $OCH_3$, $CF_3$, $OCF_3$, $NO_2$, $CH_3$, $CH_2$—OH, and —$NHSO_2R_8$; and $R_{7a}$ is selected from OH, $OCH_3$, halogen, $NH_2$, —$C_{1-17}$—OH and —$NHCOR_8$.

11. A compound according to claim 10, wherein the compound is of Formula (VIIA) or Formula (VIIB) below:

(VIIA)

(VIIB)

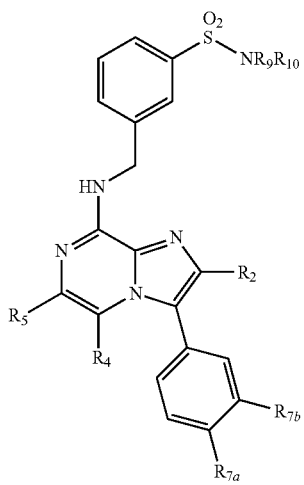

wherein:
$R_{7b}$ is selected from H, OH, halogen, $OCH_3$, $CF_3$, $OCF_3$, $NO_2$ and $CH_3$; and
$R_{7a}$ is selected from OH, $OCH_3$, halogen and $NH_2$.

12. The compound according to claim 11, wherein $R_{7b}$ is selected from H, OH, halogen, $OCH_3$, $NO_2$ and $CH_3$; and $R_{7a}$ is selected from OH, $OCH_3$, halogen and $NH_2$.

13. The compound according to claim 12, wherein $R_{7a}$ is selected from OH and $OCH_3$.

14. The compound according to claim 11, wherein $R_2$, $R_4$ and $R_5$ are selected from H and $CH_3$.

15. The compound according to claim 10, wherein $R_{7b}$ is selected from H, OH, halogen, $OCH_3$, $NO_2$ and $CH_3$; and $R_{7a}$ is selected from OH, $OCH_3$, halogen and $NH_2$.

16. The compound according to claim 15, wherein $R_{7a}$ is selected from OH and $OCH_3$.

17. The compound according to claim 10, wherein $R_2$, $R_4$ and $R_5$ are selected from H and $CH_3$.

* * * * *